US012649767B2

(12) United States Patent
Wu et al.

(10) Patent No.: US 12,649,767 B2
(45) Date of Patent: Jun. 9, 2026

(54) COMPOSITIONS COMPRISING ANNEXIN V AND HPV TUMOR ANTIGEN FUSION POLYPEPTIDES AND METHODS FOR MAKING AND USE

(71) Applicant: The Johns Hopkins University, Baltimore, MD (US)

(72) Inventors: Tzyy-Choou Wu, Stevenson, MD (US); Chien-Fu Hung, Timonium, MD (US); Tae Heung Kang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1071 days.

(21) Appl. No.: 17/265,498

(22) PCT Filed: Aug. 2, 2019

(86) PCT No.: PCT/US2019/044886
§ 371 (c)(1),
(2) Date: Feb. 2, 2021

(87) PCT Pub. No.: WO2020/028794
PCT Pub. Date: Feb. 6, 2020

(65) Prior Publication Data
US 2023/0203104 A1 Jun. 29, 2023

Related U.S. Application Data

(60) Provisional application No. 62/713,782, filed on Aug. 2, 2018.

(51) Int. Cl.
| | |
|---|---|
| *C07K 14/025* | (2006.01) |
| *A61K 39/00* | (2006.01) |
| *A61P 35/00* | (2006.01) |
| *C07K 14/005* | (2006.01) |
| *C07K 14/47* | (2006.01) |
| *C12N 15/85* | (2006.01) |

(52) U.S. Cl.
CPC ........ *C07K 14/025* (2013.01); *A61K 39/0011* (2013.01); *A61P 35/00* (2018.01); *C07K 14/005* (2013.01); *C07K 14/4705* (2013.01); *C12N 15/85* (2013.01); *C07K 2319/00* (2013.01)

(58) Field of Classification Search
CPC ...... A61P 31/16; A61P 35/00; A61K 2039/53; A61K 39/145; A61K 39/295; A61K 2039/70; A61K 2039/585; A61K 2039/6075; A61K 39/0011; C07K 14/005; C07K 14/025; C07K 14/4748; C07K 2319/00; C07K 2319/33
See application file for complete search history.

(56) References Cited

U.S. PATENT DOCUMENTS

| | | | |
|---|---|---|---|
| 7,833,775 B2 * | 11/2010 | Dubensky, Jr. | .............................. A61K 39/001158 424/193.1 |
| 10,799,579 B2 * | 10/2020 | Wu | ....................... A61K 47/643 |
| 11,766,478 B2 * | 9/2023 | Wu | ........................ A61K 39/39 424/192.1 |
| 2006/0204509 A1 | 9/2006 | Harty et al. | |
| 2018/0169221 A1 | 6/2018 | Wu et al. | |

FOREIGN PATENT DOCUMENTS

| | | | | |
|---|---|---|---|---|
| WO | WO2016115431 | * | 7/2016 | ............. A61K 38/17 |
| WO | WO2016141284 | * | 9/2016 | ........... C12N 5/0783 |

OTHER PUBLICATIONS

International Search Report and the Written Opinion from corresponding PCT Application No. PCT/US2019/044886 dated Nov. 21, 2019, 7 pages.

* cited by examiner

*Primary Examiner* — Bao Q Li
(74) *Attorney, Agent, or Firm* — Fox Rothschild LLP

(57) ABSTRACT

The present invention provides synthetic polypeptides comprising an annexin V protein, or a functional portion or fragment or variant thereof, conjugated to a tumor antigen, or a functional portion or fragment or variant thereof. The invention further provides methods for making said synthetic polypeptides and their use in the treatment of proliferative diseases such as cancer and tumors originating therefrom.

21 Claims, 46 Drawing Sheets
Specification includes a Sequence Listing.

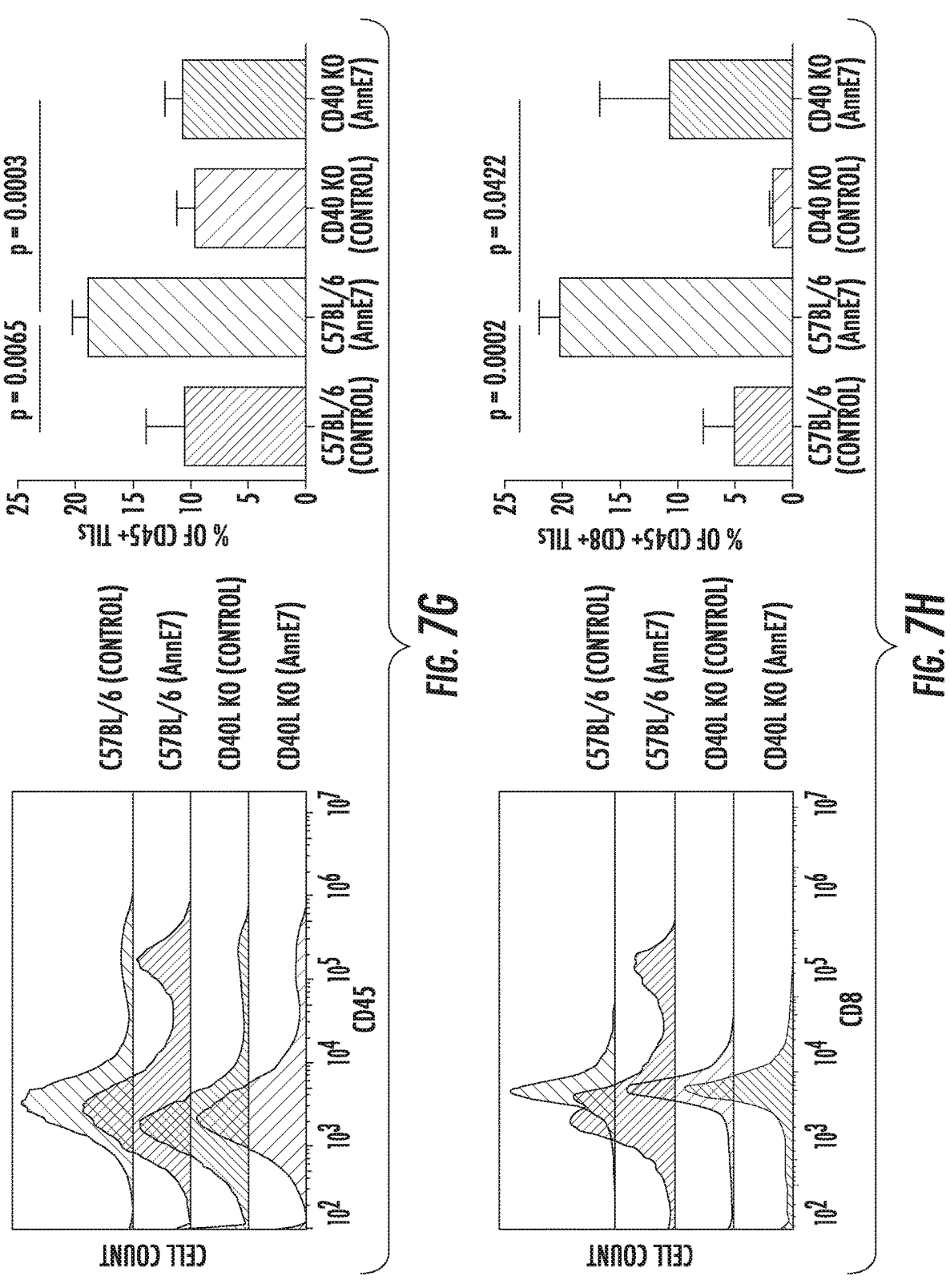

CD45-PD-L1+                    CD45+PD-L1+

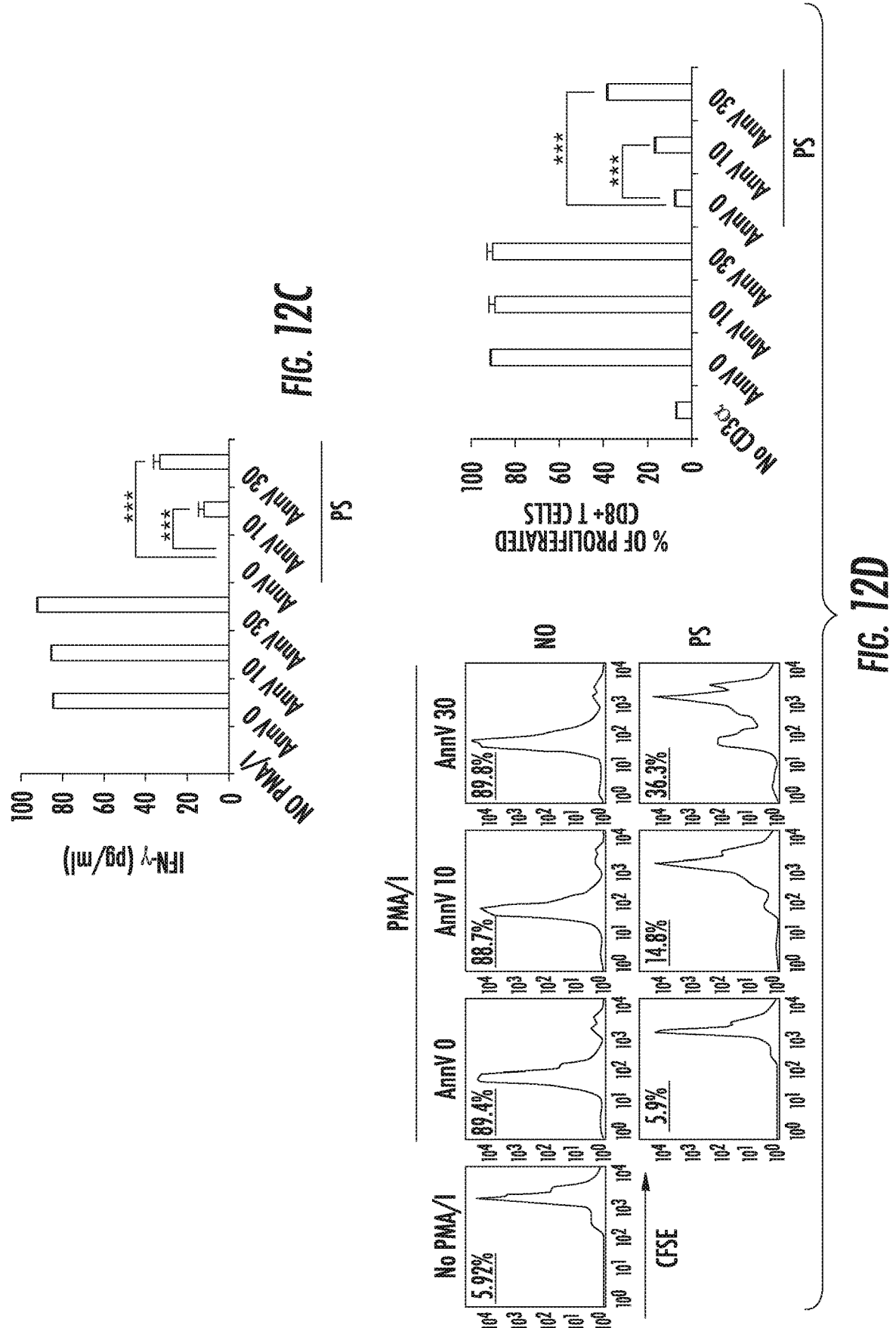

DAYS AFTER TC-1 TUMOR INJECTION

DAYS AFTER TC-1 TUMOR INJECTION

COMPOSITIONS COMPRISING ANNEXIN V AND HPV TUMOR ANTIGEN FUSION POLYPEPTIDES AND METHODS FOR MAKING AND USE

CROSS-REFERENCE TO RELATED APPLICATIONS

This application is a National Stage Application filed under 35 U.S.C. § 371, of International Patent Application No PCT/US2019/044886, filed on Aug. 2, 2019, which claims the benefit of and priority to U.S. Provisional Application No. 62/713,782, filed on Aug. 2, 2018. The entire contents of which are incorporated herein by reference in their entirety.

STATEMENT OF GOVERNMENTAL INTEREST

This invention was made with government support under grants CA098252 and CA114425 awarded by the National Institutes of Health. The government has certain rights in the invention.

INCORPORATION BY REFERENCE OF SEQUENCE LISTING

The instant application contains a Sequence Listing which has been submitted in ASCII format via EFS-Web and is hereby incorporated by reference in its entirety. Said ASCII copy, created on Mar. 3, 2021, is named 048317-607N01US_SL.txt and is 13,874 bytes in size.

BACKGROUND OF THE INVENTION

Platelets are small anucleate cell fragments that have long been known to function in hemostatic and coagulative processes. However, platelet inflammatory functions have also been well documented (for review, see (1)). Specifically, platelets are able to modulate local immune responses through the release of different cytokines and chemokines. More importantly, platelets are capable of inducing adaptive immunity through immunomodulatory ligands. Platelets are the major source of soluble, circulating cluster of differentiation 40 ligand (CD40L), which plays an important role in generating immune responses (2, 3). Through CD40L (or CD154), activated platelets induce the maturation of dendritic cells (DCs) while enhancing CD8+ T cell responses (4). Thus, CD40L is vital in eliciting potent platelet-associated adaptive immune responses, especially during viral infections.

Platelets are also known to be associated with cancer metastasis. Platelets aggregate with tumor cells to facilitate immune-evasion, support tumor cell adhesion and growth, and most importantly, enhance angiogenesis to promote the development of metastatic processes (5). Because human and animal tumor cells are capable of inducing the aggregation of platelets to further activate them (6), many cancer patients frequently present with signs of thrombosis (7). In fact, an increased circulating platelet count, or thrombocytosis, is associated with a poor prognosis of a plethora of cancers, including cervical cancer (5, 8), and is frequently observed in metastatic malignancies (9). Contrastingly, during thrombocytopenia, or the depletion of platelets, tumor cell proliferation is reduced, tumor necrosis is increased, and metastatic processes are attenuated (10, 11) (for review, see (12)).

Annexin V, a protein in the annexin superfamily, has a high affinity for phosphatidylserine (PS). Based on this property, annexin V has been commonly used to detect the apoptotic cells in vitro and as a prognostic marker for non-small cell lung cancer and non-Hodgkin's lymphoma (13). Moreover, annexin V and its homodimer, diannexin, has been used to reduce tumor growth and angiogenesis by blocking oncogene-containing tumor cell-derived microvesicles (14, 15). More recently, annexin V has been shown to be an effective inhibitor of blood coagulation in vitro by competing for PS binding sites with prothrombin, leading to the inhibition of coagulative processes (16, 17). Annexin V binds to collagen and thrombin-activated platelets through externalized PS (18, 19).

As cells undergo apoptosis, the phosphatidylserine (PS) that normally resides in the inner leaflet of the plasma membrane undergo relocalization to the outer plasma membrane and become exposed to the extracellular environment (42). Once externalized, PS interacts with PS receptors expressed on vast majority of phagocytes, serving as a "eat me" signal and promoting phagocytic uptake of apoptotic cells (43, 44). In addition, the interaction between PS and PS receptors induces the expression and release of immunosuppressive cytokines by phagocytes (45). Together, these effects help maintain the homeostasis of the healthy body and prevent the generation of undesirable inflammatory response during normal cell death by inducing the "immune suppressive clearance" of dying, apoptotic cells (46).

While the intended function of PS-mediated clearance of apoptotic cells is to prevent the development of autoimmune responses against self-antigens, the same pathways are hijacked by cancers to suppress the generation of antitumor immunity by tumor bearing host (for review see (47)). It is well recognized that a variety of conditions in the tumor microenvironment (TME), such as hypoxia, the presence of oxygen radicals, or exposure to anti-cancer treatments including irradiation and chemotherapy, can cause cellular stress and promote the externalization of PS by stressed tumor cells and apoptotic tumor bodies (47, 48). In turn, the elevated presence of exposed-PS help contributed to the formation of an immunosuppressive TME, inhibiting the functions of tumor-targeting immune cells and preventing the immune clearance of tumors(49-51). Due to the role of PS dysregulation in the formation of immunosuppressive TME, strategies inhibiting PS signaling have been explored as potentially attractive methods to enhance the potency of antitumor immunity (52-54).

It has been shown that cancer regression is highly correlated with an increase in the local CD8+ T cell response in the tumor microenvironment (TME) (54-57). Currently, anti-cancer immunotherapies are delivered through various vaccination routes, including intratumoral injections and localized mucosal delivery, such as intravaginal vaccinations (58-60). While these methods are efficacious, they are invasive in nature, leading to low patient participation in clinical settings (61-63). Thus, there is a need to develop alternative therapeutic methods to effectively control cancer progression that are more easily adopted in clinical settings.

SUMMARY OF THE INVENTION

Due to the nature of activated platelets, strategies that inhibit their tumorigenic properties while simultaneously enhancing immunogenicity could have profound effects on cancer treatment. As a result, the present inventors have developed an immunotherapeutic strategy for the human papillomavirus (HPV)-associated cancers by targeting tumor-activated platelets with annexin V linked to the HPV tumor antigens. HPV has been identified as the primary etiological factor leading to a variety of cancers, including the fourth most common female cancer worldwide: cervical cancer (20-22). This discovery has led to the development of various immunotherapies targeting HPV antigens in order to treat HPV infections and HPV-associated cancers. Because tumor-activated platelets induce thrombin activation upon externalization of PS, the present inventors developed a novel chimeric synthetic polypeptide comprising an annexin V protein, or a functional portion or fragment or variant thereof, conjugated to a HPV tumor antigen to selectively target tumor-activated platelets (AnnE7).

In accordance with one or more embodiments, the inventors now show that administration of AnnV alleviates the immunosuppressive properties of TME generated by chemotherapy and enhances the immunogenicity and antitumor efficacy of tumor antigen-specific immunization. The potency of AnnV for immune checkpoint blockade therapy is comparable to that of other reported immune checkpoint inhibitors, including anti-PD-1, anti-PD-L1, anti-TIM-3, and anti-TGF-β. Furthermore, the inventors have demonstrated that AnnV can also serve as a homing molecule to concentrate AnnV-linked tumor-antigens into PS-rich TME to enhance the magnitude of localized antitumor immunity. Furthermore, AnnV treatment can be combined with immune checkpoint inhibitors targeting other signaling pathways for the induction of elevated, synergistic antitumor immune response. Our inventive compositions and their use provide the data which supports the use of AnnV inventive compositions following chemotherapy as a promising immune checkpoint inhibitor for cancer treatment.

In accordance with one or more embodiments, the present inventors found that AnnE7 is able to target both thrombin-activated and tumor-activated platelets. The inventors now demonstrate that AnnE7 effectively targets HPV antigens to the tumor microenvironment of TC-1 tumor-bearing mice more so than the tumor antigens alone without annexin V. The compositions of the present invention then led to the potent activation of adaptive CD8+ T cell immunity by eliciting high levels of tumor antigen specific CD8+ T cells, inhibiting the growth of an E6/E7-expressing tumor cell, TC-1 tumor cells, and extending the survival of tumor bearing mice. Furthermore, the anti-tumor response elicited by the compositions of the present invention is abolished through platelet depletion and CD40L knockout, confirming the concept that tumor activated platelets play a role in AnnE7 therapeutic efficacy. The present inventors now show that a synthetic polypeptide comprising an annexin V protein, or a functional portion or fragment or variant thereof, conjugated to a HPV tumor antigen, or a functional portion or fragment or variant thereof enhances tumor antigen-specific CD8+ T cell response through platelet derived CD40L and targeting by tumor-activated platelets, and use the present inventions to further drive the development of antigen-specific cancer immunotherapies.

Therefore, in accordance with an embodiment, the present invention provides a synthetic polypeptide comprising an annexin V protein, or a functional portion or fragment or variant thereof.

In accordance with an embodiment, the present invention provides a synthetic polypeptide comprising an annexin V protein, or a functional portion or fragment or variant thereof, conjugated to an antigen, or a functional portion or fragment or variant thereof.

In accordance with an embodiment, the present invention provides a synthetic polypeptide comprising an annexin V protein, or a functional portion or fragment or variant thereof, conjugated to a tumor associated antigen, or a functional portion or fragment or variant thereof.

In accordance with another embodiment, the present invention provides a synthetic polypeptide comprising an annexin V protein, or a functional portion or fragment or variant thereof, conjugated to a HPV tumor antigen, or a functional portion or fragment or variant thereof.

In accordance with another embodiment, the present invention provides a synthetic polypeptide comprising an annexin V protein, or a functional portion or fragment or variant thereof, conjugated to a CT26 tumor antigen, or a functional portion or fragment or variant thereof.

In accordance with another embodiment, the present invention provides a synthetic polypeptide comprising at the N-terminus, an annexin V protein, or a functional portion or fragment or variant thereof, conjugated to an antigen, or a functional portion or fragment or variant thereof at the C-terminus.

In accordance with another embodiment, the present invention provides a synthetic polypeptide comprising at the C-terminus, an annexin V protein, or a functional portion or fragment or variant thereof, conjugated to an antigen, or a functional portion or fragment or variant thereof at the N-terminus.

In accordance with a further embodiment, the present invention provides a synthetic polypeptide comprising an annexin V protein, or a functional portion or fragment or variant thereof, further comprising a detectable moiety.

In accordance with an embodiment, the present invention provides a nucleic acid composition encoding a synthetic polypeptide comprising any or all of the above embodiments.

In accordance with another embodiment, the present invention provides a nucleic acid composition encoding a synthetic polypeptide, wherein the N-terminal portion of the polypeptide comprises an annexin V protein, or a functional portion or fragment or variant thereof, conjugated to an antigen, or a functional portion or fragment or variant thereof, at the C-terminal portion of the fusion protein.

In accordance with another embodiment, the present invention provides a nucleic acid composition encoding a synthetic polypeptide, wherein the C-terminal portion of the polypeptide comprises an annexin V protein, or a functional portion or fragment or variant thereof, conjugated to an antigen, or a functional portion or fragment or variant thereof, at the N-terminal portion of the fusion protein.

In accordance with a further embodiment, the present invention provides a nucleic acid composition encoding a synthetic polypeptide comprising an annexin V protein, or a functional portion or fragment or variant thereof, conjugated to an antigen, or a functional portion or fragment or variant thereof, and further comprising a detectable moiety.

In accordance with another embodiment, the present invention provides a method for treating a hyperproliferative disease in a subject comprising administering to the subject an effective amount of any one or more of the synthetic peptide compositions described above.

In accordance with an embodiment, the present invention provides a method for treating a tumor in a subject comprising administering to the subject an effective amount of any one or more of the synthetic peptide compositions described above.

In accordance with a further embodiment, the present invention provides a method for treating a tumor in a subject comprising administering to the subject an effective amount of any one or more of the synthetic peptide compositions
described above, and at least one additional biologically
active agent.

In accordance with another embodiment, the present
invention provides a method for treating a hyperproliferative
disease in a subject comprising administering to the subject
an effective amount of any one or more of the synthetic
peptide compositions described above after the subject is
treated with one or more doses of a chemotherapeutic agent.

6

FIG. 5 illustrates the AnnE7 fusion polypeptide generat-
ing anti-tumor immunity and prolonging survival of TC-1
tumor-bearing mice. (5A) Schematic illustration of the
experiment. Tumor-bearing mice (n=5) were treated with
E7, annexin V, or AnnE7 on days 5, 8, and 11 after TC-1
tumor inoculation. Control mice were treated with phos-
phate buffered saline (PBS). On day 14, peripheral blood
mononuclear cells (PBMCs) were collected for E7 tetramer
staining. (5B) Representative flow cytometry images of E7
tetramer staining. PBMCs were stained with the PE-conju-
gated HPV16 E7aa49-57 peptide-loaded H-2D$^b$ E7 tetramer
and FITC-conjugated anti-mouse CD8a antibodies, fol-
lowed by flow cytometry. (5C) Bar graph summary of flow
cytometric analyses. (5D) Tumor growth curve of TC-1
tumor-bearing mice. (5E) Kaplan-Meier survival curve of
TC-1 tumor-bearing mice.

Figures 4A, 4B:
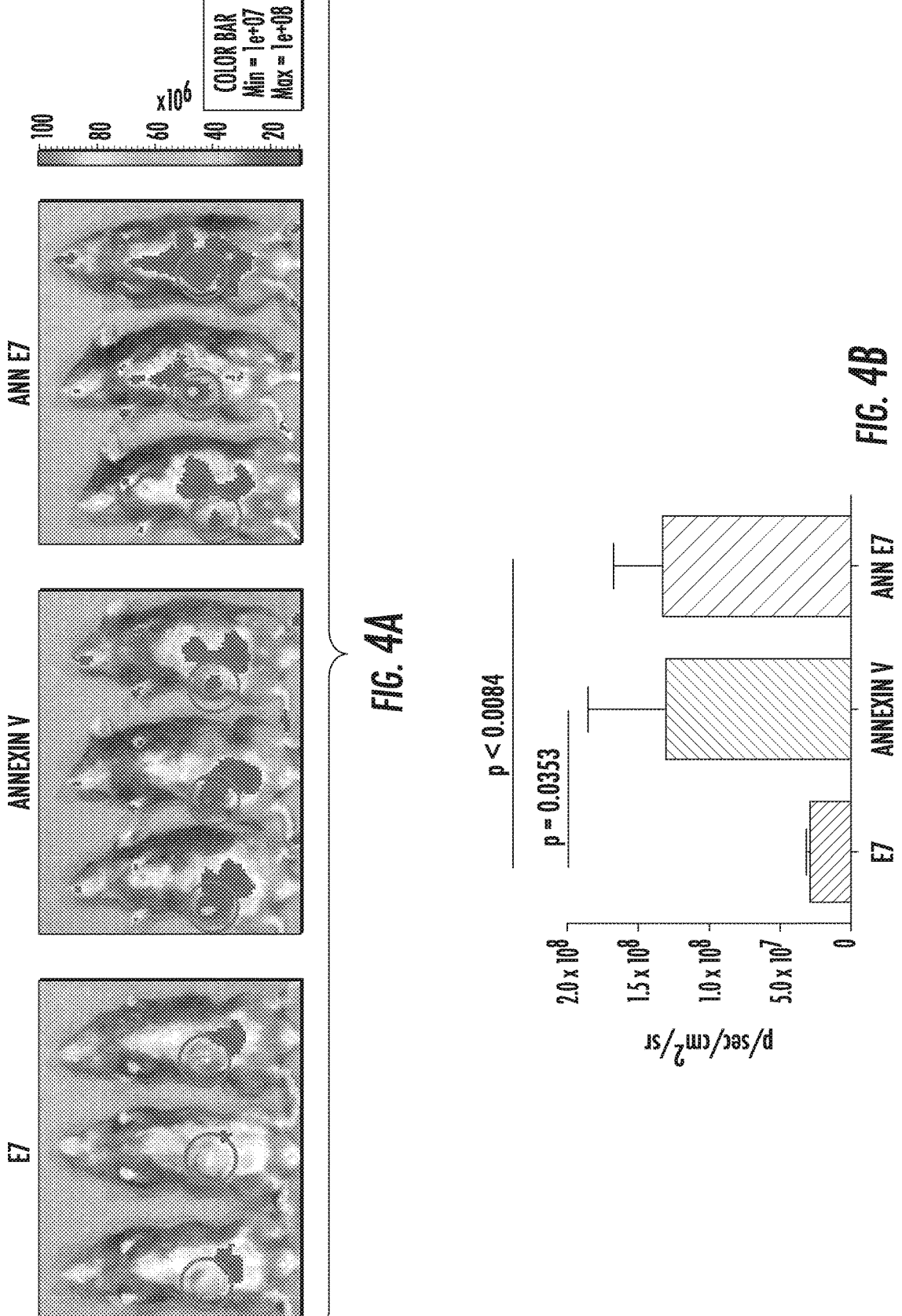
FIG. 4 shows that the AnnE7 fusion polypeptide and
annexin V have higher tumor targeting ability. Equimolar
amounts of Alexa647-labeled E7, annexin V, or AnnE7 were
injected into TC-1 tumor-bearing mice (n=3). (4A) Mice
were imaged by IVIS spectrum 24 hrs after injection.
Tumors are outlined in red circles. (4B) Quantification of the
fluorescence signals shown in (4A). (4C) Tumors were
excised and imaged. (4D) Quantification of the fluorescence
signals of excised tumors shown in (4C). The region of
interest from the displayed images was quantified as a total
photon count using the Living Image 2.50 software (Xeno-
gen). (4E) After imaging, tumor tissues were minced into 1-
to 2-mm pieces and filtered through a 70-μm nylon cell
strainer. Single cell suspensions were washed with a FACS
washing buffer and their Alexa647 intensities were analyzed
by flow cytometry. (4F) The mean fluorescence intensities of
Alexa647.
Figures 4C, 4D:
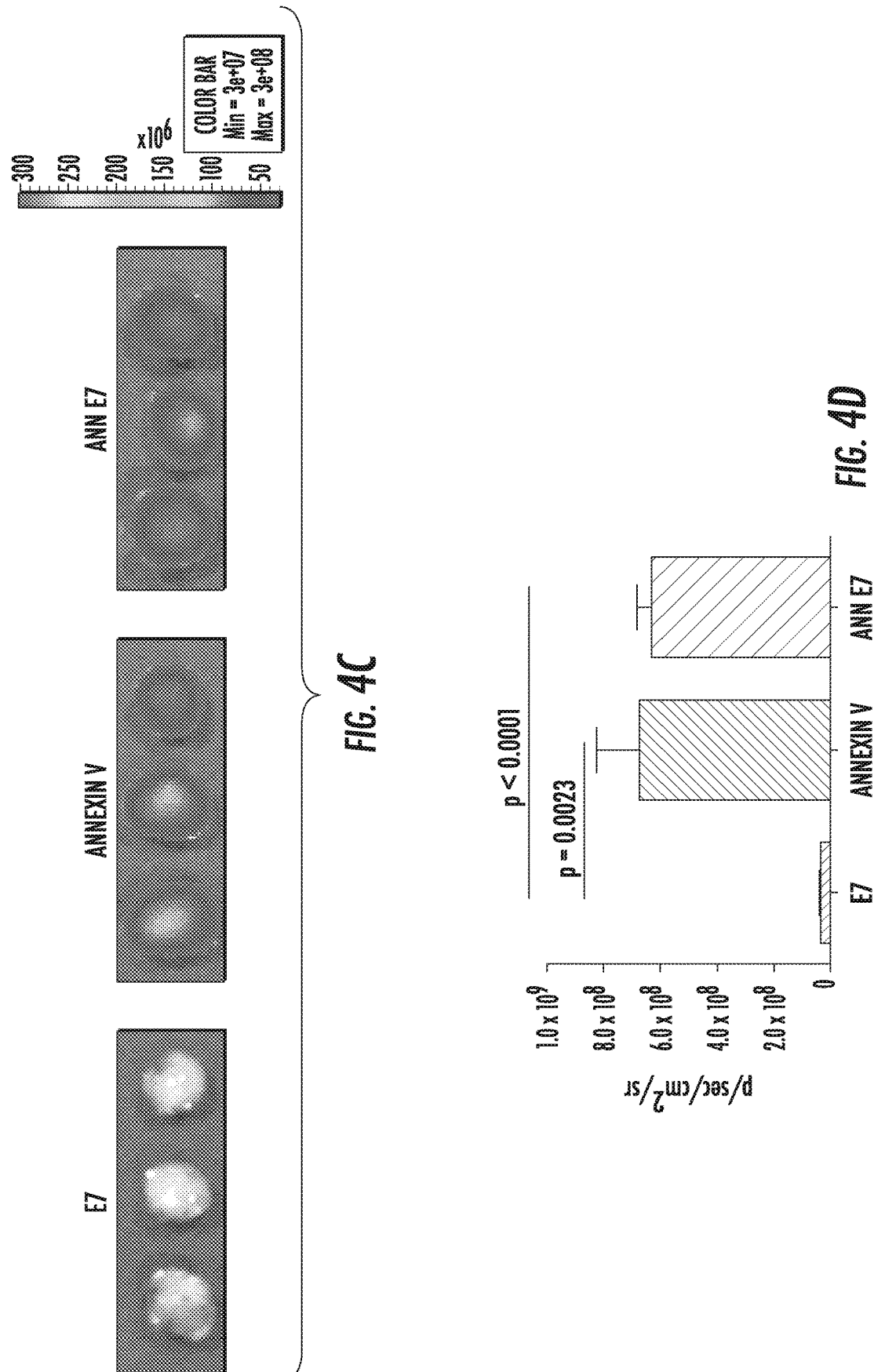

FIG. 6 shows the anti-tumor immunity of the AnnE7
fusion polypeptide is dependent on tumor-activated plate-
lets. (6A) The combination of AnnE7 with tumor-activated
platelets generates E7-specific CD8+ T cells in naive
C57BL/6 mice. Mice (n=3) were intravenously injected with
either 100 μg of AnnE7, a mixture of 100 μg of AnnE7 and
10$^8$ tumor-activated platelets, or a mixture of 100 μg of
annexin V and 10$^8$ tumor-activated platelets once a week for
a total of three weeks. Untreated naive mice served as
control. PBMCs were collected for E7 tetramer staining.
(6B) Summary of flow cytometric analyses. (6C) To deplete
platelets in tumor-bearing mice, mice received 1 mg/kg of
anti-mouse CD41 antibodies one day prior to AnnE7 treat-
ment. Control mice received the same dose of mouse IgG
isotype antibodies. AnnE7 treatment proceeded in the same
fashion as FIG. 4A. Shown here are representative flow
cytometric images of E7 tetramer staining. (6D) Bar graph
summary of flow cytometric analyses. (6E) Tumor growth
curve of platelet-depleted mice. (6F) Kaplan-Meier survival
of platelet-depleted mice.

FIG. 7 shows that platelet-derived CD40L is essential for
the AnnE7 fusion polypeptide derived anti-tumor immunity.
Naive C57BL/6 (n=5) and CD40L knockout (KO) (n=5)
tumor-bearing mice were treated with either AnnE7 or PBS
on day 5, 8, and 11 after initial tumor challenge with 2×10$^5$
TC-1 cells. On day 14, PBMCs were collected for E7
tetramer staining. (7A) Representative flow cytometric
images from the E7 tetramer staining. (7B) Bar graph
summary of flow cytometric analyses. (7C) Tumor growth
curve of tumor-bearing mice after treatment. (7D) 10$^8$
tumor-activated platelets were isolated from C57BL/6 or
CD40L KO tumor-bearing mice and mixed with 100 μg of
AnnE7. The mixture was intravenously injected into naive
C57BL/6 mice (n=3) once a week for a total of three weeks.
PBMCs were collected for E7 tetramer staining. Shown here
are representative flow cytometric images of E7 tetramer
staining. (7E) Bar graph summary of flow cytometric analy-
ses. (7F) Elevated soluble CD40L (sCD40L) in tumor
explant supernatants. sCD40L levels in tumor explant super-
natants (n=3) were compared to plasma form naive mice or
tumor-bearing mice by ELISA. (7G) Representative flow
cytometric images of tumor-infiltrating lymphocytes (TILs).
PBMCs were stained with PE-conjugated anti-mouse CD45
antibodies and FITC-conjugated anti-mouse CD8a antibod-
ies, followed by flow cytometry. Shown here are represen-
tative flow cytometric images of CD45+ TILs, including a
bar graph summary to the right. (7H) Shown here are
representative flow cytometric images of CD45+CD8+
TILs, including a bar graph summary to the right.

Figure 8:
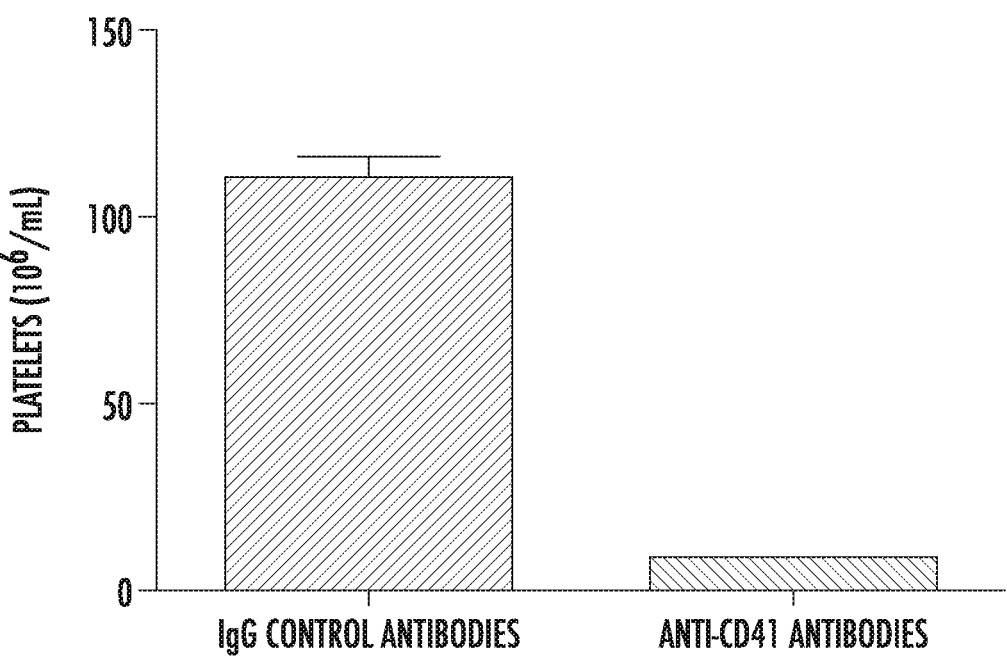

FIG. 8 shows that platelets were significantly depleted by
anti-mouse CD41 antibodies by administering anti-CD41 platelet antibodies to tumor-bearing mice. Mice IgG isotype antibodies administered to tumor-bearing mice served as controls. After 24 hrs, platelets were collected and counted by a hemocytometer.

FIGS. 9A-9E depict characterization of therapeutic anti-tumor effects and antigen-specific immune responses generated by concomitant administration of Annexin V protein and antigenic peptide following cisplatin treatment. C57BL/6 mice (ten per group) were injected with $2 \times 10^5$ TC-1 cells/mouse subcutaneously on day 0. Mice were then treated intraperitonealy with 5 mg/kg cisplatin on days 12 and 15, intravenously with 200 µg/mice of Annexin V proteins on days 13, 14, 16, and 17, and/or intratumorally with 20 µg/mice of E7 long peptide on days 13 and 16. PBS was used as control. (9A) Schematic diagram. (9B) Line graph depicting TC-1 tumor growth in different treatment groups over time. (9C) Kaplan-Meier survival analysis of TC-1 tumor-bearing mice in different treatment groups. (9D-9E) On days 18 and 23, tumor tissues and spleens of TC-1 tumor-bearing mice in different treatment groups were harvested and analyzed for CD8+IFN-γ+ T cells by flow cytometry analysis, respectively. (9D) Representative flow cytometry analysis and bar graph depicting the abundance of CD8+IFN-γ+ T cells in spleenocytes of TC-1 tumor bearing mice in different treatment groups. (9E) Representative flow cytometry analysis and bar graph depicting the abundance of CD8+IFN-γ+ tumor-infiltrating T cells in TC-1 tumor bearing mice in different treatment groups. Data represents mean±SD. *P<0.05, ***P<0.001.

FIGS. 10A-10E show the tumor immune microenvironment following cisplatin and Annexin V treatment. C57BL/6 mice (ten per group) were injected with $2 \times 10^5$ TC-1 cells/mouse subcutaneously on day 0. Mice were then treated intraperitonealy with 5 mg/kg cisplatin on days 12 and 15, and/or intravenously with 200 µg/mice of Annexin V proteins on days 13, 14, 16, and 17. PBS was used as control. On day 18, tumor tissues and serum of mice were harvested. (10A) Schematic diagram. (10B) Bar graphs depicting the abundance of CD11b+F4/80+ macrophages and their M1/M2 distributions in the tumor tissue following flow cytometry analysis. (10C) Bar graphs depicting the presence of CD8+ T cells, CD4+ T cells, Treg cells, and MDSCs in the tumor tissue following flow cytometry analysis. (10D) Bar graphs depicting the expression of PD-L1 by CD45+ immune cells and CD45−tumor cells following flow cytometry analysis. (10E) Bar graphs depicting the levels of TNF-α, IL-10 and TGF-β cytokines in the tumor tissue and serum of mice as measured by ELISA. Data represents mean±SD. *P<0.05, **P<0.01, N.S.=not significant.

Figure 11:
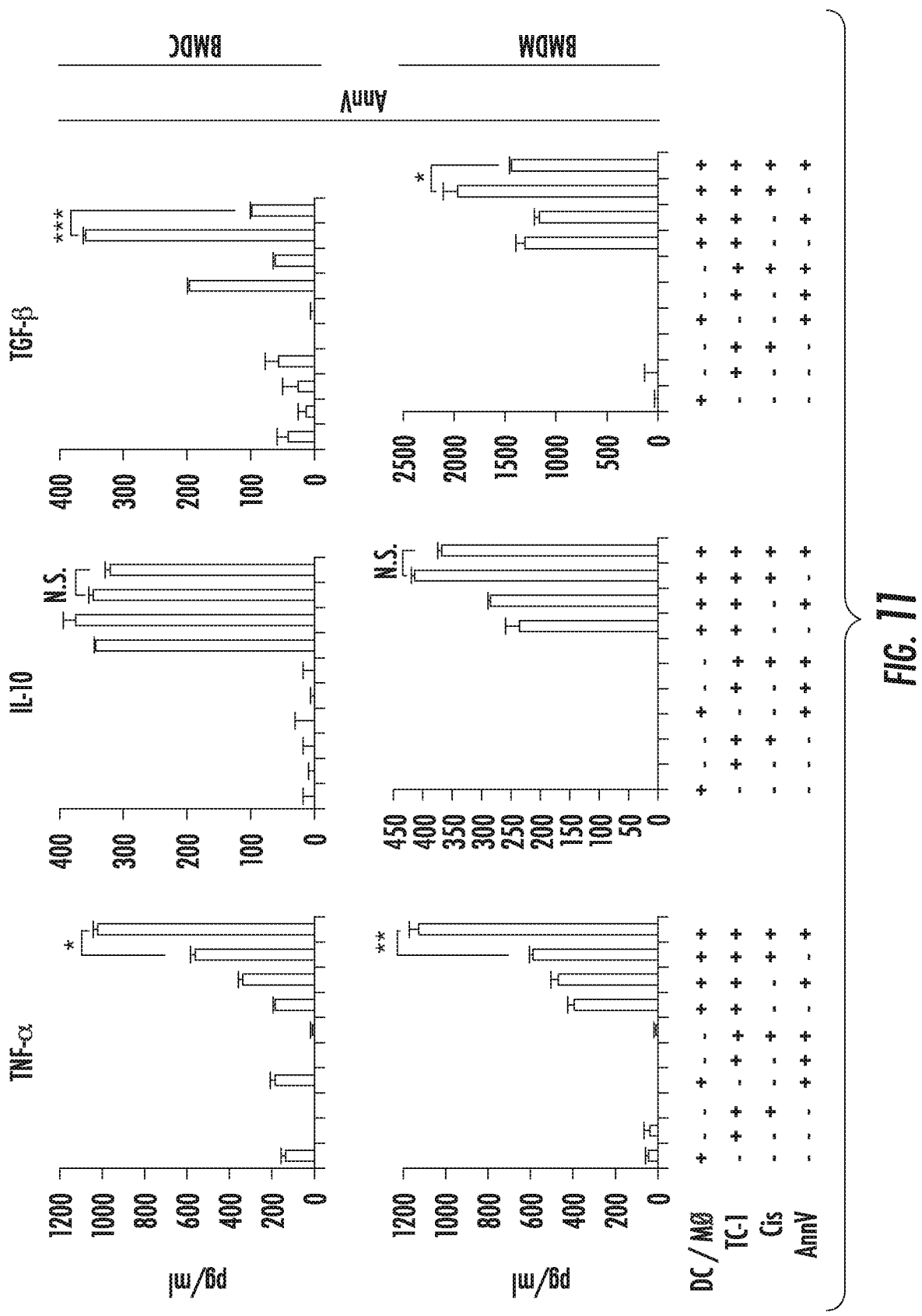

FIG. 11 depicts Annexin V treatment promotes the secretion of pro-inflammatory cytokines and suppresses the secretion of anti-inflammatory cytokines by innate immune cells exposed to cisplatin-induced apoptotic tumor cells. $1 \times 10^5$ of TC-1 tumor cells were treated with or without 20 µg/ml of cisplatin for 6 hours. The tumor cells were then washed twice with PBS and co-cultured with $1 \times 10^5$ of bone marrow derived dendritic cell or bone marrow derived macrophage with or without concomitant incubation with 20 µg/ml AnnexinV protein. 24 hours after co-culturing, supernatants were collected and assessed for TNF-α, TGF-β, and IL-10 cytokine levels by ELISA. Bar graph depicting the levels of cytokines in various treatment group. Data represents mean±SD. *P<0.05, P<0.01, *P<0.001, N.S.=not significant.

FIGS. 12A-12F show Annexin V treatment inhibits T cell suppressive effects of phosphatidyl-serine and apoptotic tumor cells. CFSE-labeled splenic naive T cells were stimulated for 18 h with anti-CD3α mAb (10 µg/ml) (12A-12B) or PMA (50 ng/ml) plus Ionomycin (500 ng/ml) (12C-12D) in the presence of Phosphatidyl-serine (5 µg/ml) with or without co-treatment of annexinV protein (10 µg/ml or 30 µg/ml). (12E-12F) $1 \times 10^6$ CFSE labelled OVA specific CD8+ T cells were co-cultured with OVA expressing TC-1 cells pre-treated with or without cisplatin and/or 20 µg/ml of AnnexinV protein. (12A, 12C and 12E) 24 hrs after incubation, the supernatants were collected and measured for IFN-γ levels using ELISA. Figure displaying histograms of supernatant IFN-γ levels. (12B, 12D, and 12F) Division of splenic T cells were assessed by flow cytometry analysis of CFSE dilution at 3 days after incubation. Figure displays representative flow cytometry image and histograms of CD8+ CFSE+ T cell proliferation. Data represents mean±SD. ***P<0.001.

FIGS. 13A-13E show generation of antigen-specific therapeutic anti-tumor effects and CD8+ T cell responses in tumor-bearing mice treated with cisplatin, antigenic peptide, and/or TGF-β or TNF-α neutralizing antibody. C57BL/6 mice (6 per group) were injected with $2 \times 10^5$ TC-1 cells/mice subcutaneously on day 0. Mice were then treated intraperitoneally with 200 µg/mice TGF-β or TNF-α neutralizing antibody on day 10, 12, 14, 16, and 18, intraperitoneally with 5 mg/kg cisplatin on days 12 and 15, and/or intratumorally with 20 µg/mice of E7 long peptide on days 13 and 16. PBS was used as control. (13A) Schematic diagram. (13B) Line graph depicts TC-1 tumor growth in different treatment groups over time. (13C) Kaplan-Meier survival analysis of TC-1 tumor-bearing mice in different treatment groups. (13D-13E) On days 19 and 23, tumor tissues and spleens of TC-1 tumor-bearing mice in different treatment groups were harvested and analyzed for CD8+IFN-γ+ T cells by flow cytometry analysis, respectively. (13D) Representative flow cytometry analysis and bar graph depicting the abundance of CD8+IFN-γ+ T cells in splenocytes of TC-1 tumor bearing mice in different treatment groups. (13E) Representative flow cytometry analysis and bar graph depicting the abundance of CD8+IFN-γ+ tumor-infiltrating T cells in TC-1 tumor bearing mice in different treatment groups. Data represents mean±SD. *P<0.05, ***P<0.001.

FIGS. 14A-14E show generation of antigen-specific therapeutic anti-tumor effects and immune response in tumor-bearing mice treated with cisplatin, antigenic peptide, and/or various immune checkpoint inhibitors. C57BL/6 mice (ten per group) were injected with $2 \times 10^5$ TC-1 cells/mouse subcutaneously on day 0. Mice were then treated intraperitoneally with 200 µg/mice α-TGF-β on day 10, 12, 14, 16, and 18, intraperitoneally with 5 mg/kg cisplatin on days 12 and 15, intravenously with 200 µg/mice of Annexin V proteins on days 13, 14, 16, and 17, intraperitoneally with 200 µg/mice of α-PD-1, α-PD-L1, or α-TIM-3 on days 13, 14, 16, and 17, intraperitoneally with 200 µg/mice TGF-β neutralizing antibody on day 10, 12, 14, 16, and 18, and/or intratumorally with 20 µg/mice of E7 long peptide on days 13 and 16. PBS and irrelevant IgG were used as controls. (14A) Schematic diagram. (14B) Line graph depicts TC-1 tumor growth in different treatment groups over time. (14C) Kaplan-Meier survival analysis of TC-1 tumor-bearing mice in different treatment groups. (14D-14E) On day 19, spleens and tumor tissues of TC-1 tumor-bearing mice in different treatment groups were harvested and analyzed for CD8+IFN-γ+ T cells by flow cytometry analysis. (14D) Representative flow cytometry analysis and bar graph depicting the abundance of CD8+IFN-γ+ T cells in spleenocytes of TC-1 tumor bearing mice in different treatment groups. (14E) Representative flow cytometry analysis and bar graph depicting the abundance of CD8+IFN-γ+ tumor-infiltrating T cells in TC-1 tumor bearing mice in different treatment groups. Data represents mean±SD. *P<0.05, ***P<0.001.

Figures 15A, 15B:
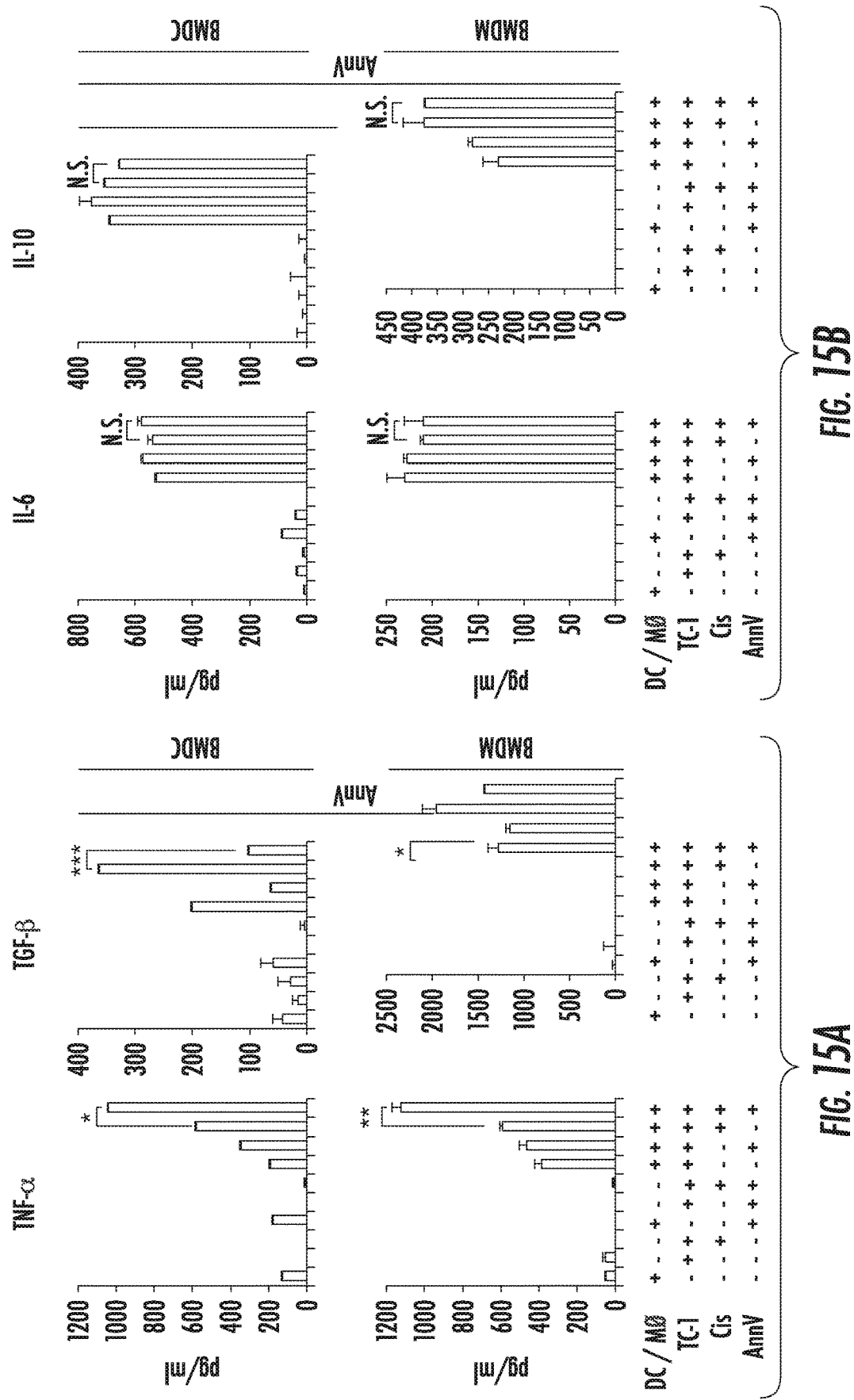

FIG. 15 depicts the preferential homing of AnnexinV protein to tumor loci following cisplatin treatment. C57BL/6 mice (3 per group) were injected with $2\times10^5$ TC-1 cells/mouse subcutaneously. 12 days later, tumor-bearing mice were treated with or without 5 mg/kg of cisplatin intraperitoneally. After 2 days, 200 μg/mice of PBS, Annexin V only, or Annexin V-Gluc proteins were injected intravenously into the lateral tail vein and the bioluminescence was imaged one day later. (15A) Representative bioluminescence imaging used to characterize the accumulation of Annexin V containing protein into tumor loci in tumor-bearing mice after cisplatin treatment. (15B) Bar graph depicting the fluorescence intensity in tumor-bearing mice treated with the various groups. Data represents mean±SD. ***P<0.001.

FIGS. 16A-16E show therapeutic antitumor effects and antigen-specific immune response generated by recombinant AnnV-E7 fusion protein following cisplatin treatment in vivo. C57BL/6 mice (ten per group) were injected with $2\times10^5$ TC-1 cells/mouse subcutaneously on day 0. Mice were then treated intraperitonealy with 5 mg/kg Cisplatin on days 12 and 15, intravenously with 200 μg/mice of Annexin V-E7 fusion protein, 200 μg/mice of Annexin V proteins, and/or 3.5 μg/mice of E7 long peptide on days 13, 14, 16, and 17. PBS was used as control. (16A) Schematic diagram. (16B) Line graph depicting TC-1 tumor growth in different treatment groups over time. (16C) Kaplan-Meier survival analysis of TC-1 tumor-bearing mice in different treatment groups. (16D-16E) On days 18 and 23, tumor tissues and spleens of TC-1 tumor-bearing mice in different treatment groups were harvested and analyzed for CD8+IFN-γ+ or CD8+E7tatramer+ T cells by flow cytometry analysis, respectively. (16D) Representative flow cytometry analysis and bar graph depicting the abundance of CD8+E7tetramer+ T cells in spleenocytes of TC-1 tumor bearing mice in different treatment groups. (16E) Representative flow cytometry analysis and bar graph depicting the abundance of CD8+IFN-γ+ tumor-infiltrating T cells in TC-1 tumor bearing mice in different treatment groups. Data represents mean±SD. *P<0.05, ***P<0.001.

Figures 16A, 16B, 16C, 16D:
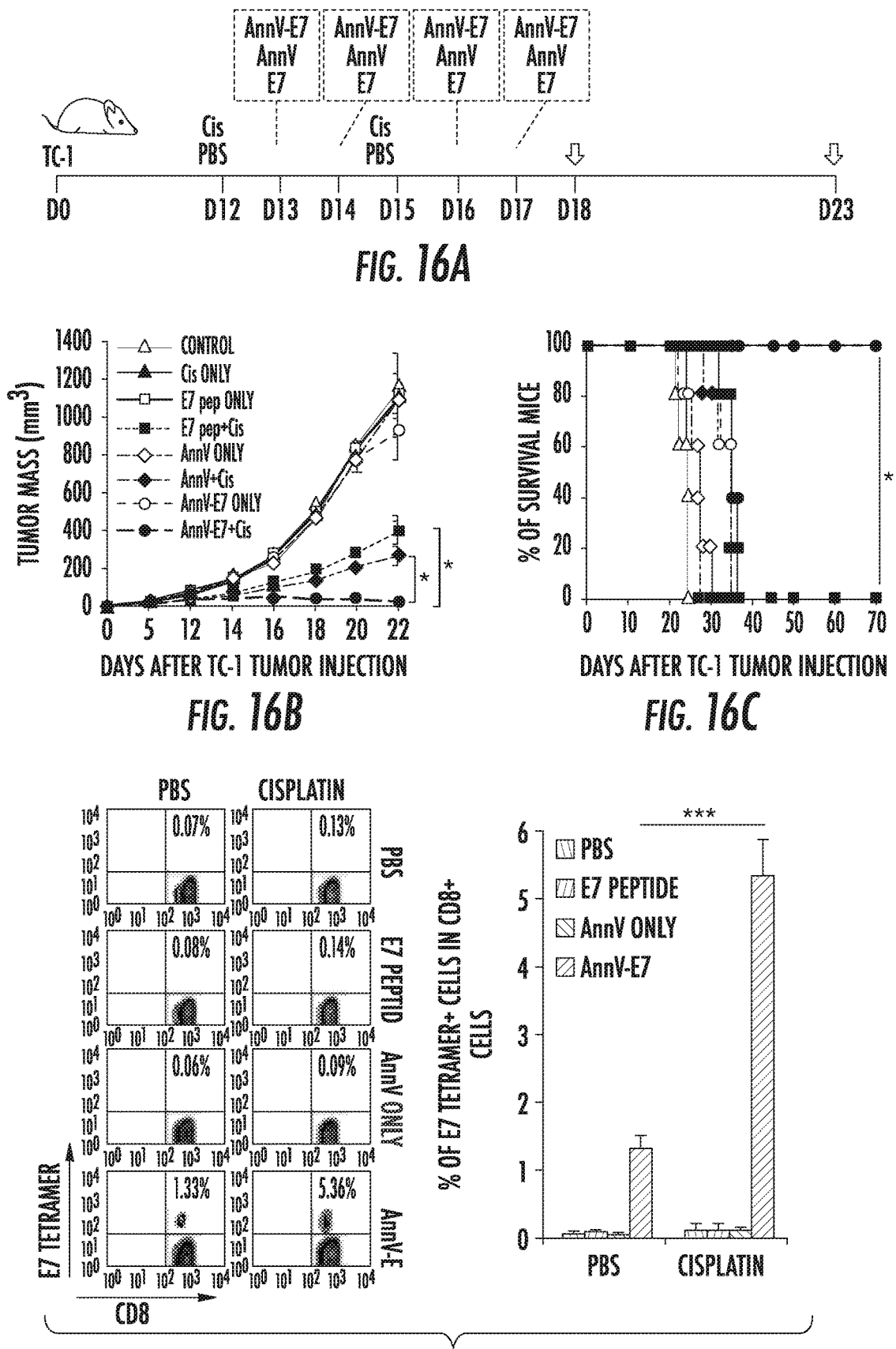
Figure 16E:
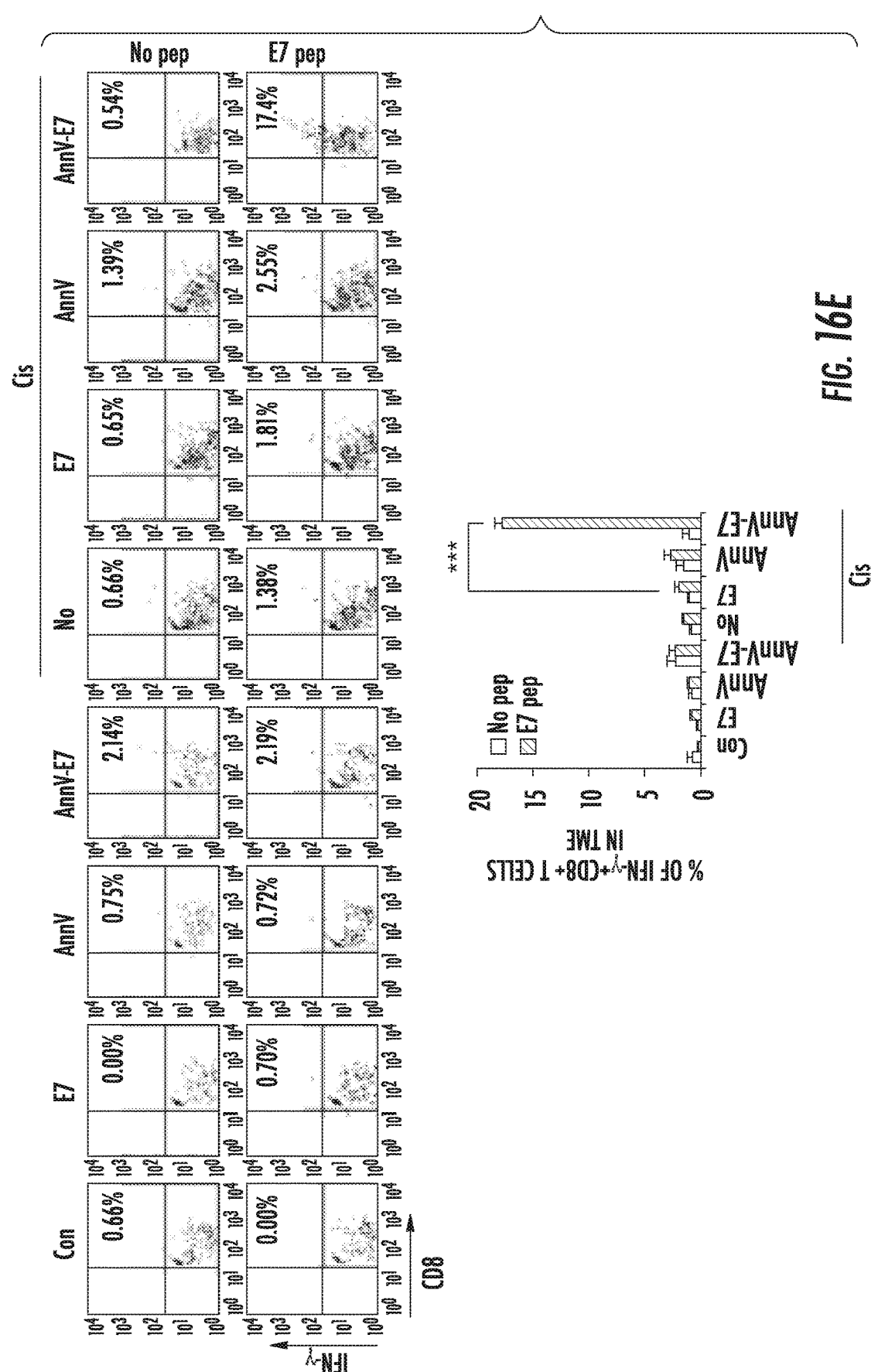
Figures 17A, 17B:
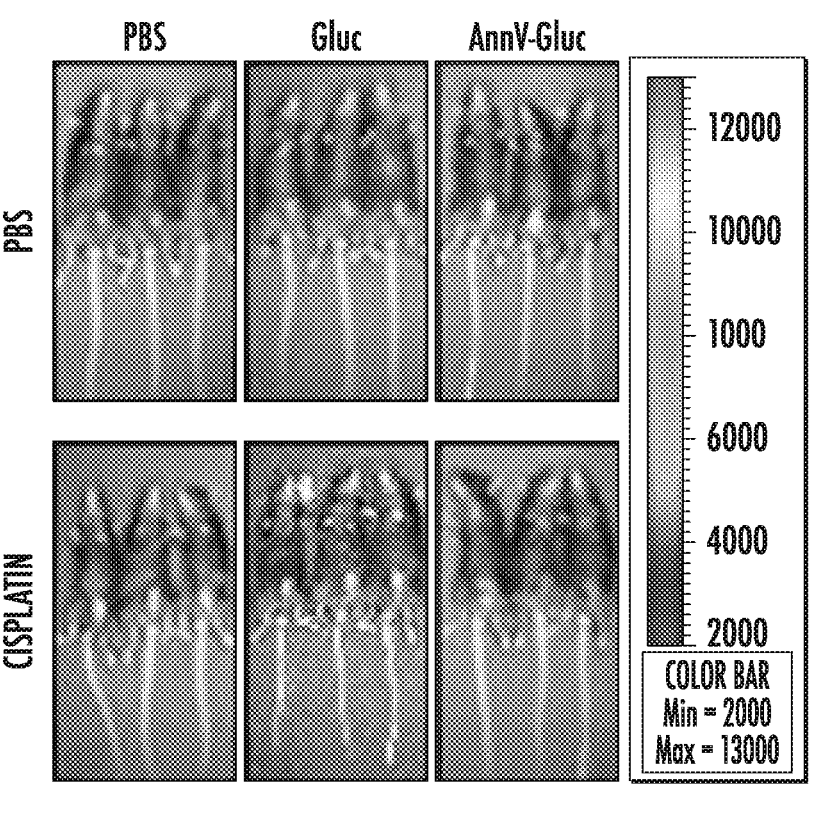

FIGS. 17A-17B depict the therapeutic antitumor effect generated by AnnexinV-E7 administration following cisplatin treatment is mediated by CD8+ T cells. (17A) C57BL/6 mice (5 per group) were challenged with TC-1 tumor cells and treated with cisplatin and AnnV-E7 using the same dosages and schedules as described in FIG. 16. 200 μg/mice of anti-CD8 depleting antibodies or control IgG antibodies were administered intraperitoneally daily from day 12 to day 20. (17B) Line graph depicts TC-1 tumor growth in control group and CD8 depleted group over time.

FIGS. 18A-18F show generation of antigen-specific immune response and therapeutic antitumor effects by concomitant treatment with chemotherapy and Annexin V-antigenic peptide fusion protein against different tumor models. (18A-18C) C57BL/6 mice (ten per group) were injected with $2\times10^5$ TC-1 cells/mouse subcutaneously on day 0. Mice were then treated intraperitoneally with 10 mg/kg doxorubicin on days 12 and 15 and intravenously with 200 μg/mice of AnnV, 200 μg/mice of AnnV-E7, or 3.5 μg/mice of E7 peptide on days 13, 14, 16, and 17. PBS was used as control. (18A) One week after the last vaccination, spleens of TC-1 tumor-bearing mice in different treatment groups were harvested and analyzed for CD8+IFN-γ+ T cells by flow cytometry analysis. Figure showing the representative flow cytometry analysis and bar graph depicting the abundance of CD8+IFN-γ+ T cells in splenocytes of TC-1 tumor bearing mice in different treatment groups. (18B) Line graph depicts TC-1 tumor growth in different treatment groups over time. (18C) Kaplan-Meier survival analysis of TC-1 tumor-bearing mice in different treatment groups. (18D-18F) BALB/c mice (ten per group) were injected with $5\times10^5$ CT-26 cells/mouse subcutaneously on day 0. Mice were then treated intraperitoneally with 5 mg/kg cisplatin on days 12 and 15 and intravenously with 200 μg/mice of AnnV, 200 μg/mice of AnnV-AH5, or 3.5 μg/mice of AH5 peptide on days 13, 14, 16, and 17. PBS was used as control. (18D) One week after the last vaccination, spleens of CT-26 tumor-bearing mice in different treatment groups were harvested and analyzed for CD8+IFN-γ+ T cells by flow cytometry analysis. Figure showing the representative flow cytometry analysis and bar graph depicting the abundance of CD8+IFN-γ+ T cells in spleenocytes of CT-26 tumor bearing mice in different treatment groups. (18E) Line graph depicts CT-26 tumor growth in different treatment groups over time. (18F) Kaplan-Meier survival analysis of CT-26 tumor-bearing mice in different treatment groups. Data represents mean±SD. *P<0.05, ***P<0.001.

FIGS. 19A-19D depict therapeutic antitumor effect of combination treatment with AnnexinV-E7 fusion protein and various immune checkpoint inhibitors following cisplatin administration in vivo. C57BL/6 mice (10 per group) were injected with $2\times10^5$ TC-1 cells/mouse subcutaneously on day 0. Mice were then treated intraperitonealy with 5 mg/kg cisplatin on days 15 and 18, intravenously with 200 μg/mice of AnnexinV-E7 proteins on days 16, 17, 19, and 20, and/or intraperitoneally with 200 μg/mice of anti-PD-1, anti-PD-L1, or anti-TIM-3 antibodies on days 21, 23, and 25. PBS was used as control. (19A) Schematic diagram. (19B) Line graph depicting TC-1 tumor growth in different treatment groups over time. (19C) Kaplan-Meier survival analysis of TC-1 tumor-bearing mice in different treatment groups. (19D) One week after the last AnnV-E7 vaccination, spleens of TC-1 tumor-bearing mice in different treatment groups were harvested and analyzed for CD8+IFN-γ+ T cells by flow cytometry analysis. Figure showing representative flow cytometry analysis and bar graph depicting the abundance of CD8+IFN-γ+ T cells in spleenocytes of TC-1 tumor bearing mice in different treatment groups. Data represents mean±SD. *P<0.05, ***P<0.001.

DETAILED DESCRIPTION OF THE INVENTION

In accordance with one or more embodiments, the present invention provides novel chimeric synthetic polypeptides comprising one or more HPV tumor antigens linked with annexin V. The present invention also comprises the use of annexin V and annexin V fused in novel chimeric synthetic polypeptides as checkpoint inhibitors in conjunction with chemotherapeutic treatment of various cancers. The synthetic fusion polypeptides of the present invention are able to generate HPV tumor antigen-specific CD8+ T cell-mediated anti-tumor immune responses while simultaneously prolonging the survival of TC-1 tumor-bearing mice.

The human papillomavirus is a DNA tumor virus that causes epithelial proliferation at cutaneous and mucosal surfaces. More than 100 different types of the virus exist, including approximately 30 to 40 strains that infect the human genital tract. Of these, there are oncogenic or high-risk types (16, 18, 31, 33, 35, 39, 45, 51, 52, and 58) that are associated with cervical, vulvar, vaginal, penile, oral, throat and anal cancers, and non-oncogenic or low-risk types (6, 11, 40, 42, 43, 44, and 54) that are associated with anogenital condyloma or genital warts. HPV 16 is the most oncogenic, accounting for almost half of all cervical cancers, and HPV 16 and 18 together account for approximately 70% of cervical cancers. HPV 6 and 11 are the most common strains associated with genital warts and are responsible for approximately 90% of these lesions.

Thus, in accordance with some embodiments, the present invention provides HPV tumor associated antigens from oncogenic or high-risk HPV types, including, for example, types 16, 18, 31, 33, 35, 39, 45, 51, 52, and 58. In some embodiments, the tumor-associated antigens are from HPV 16 or 18.

As used herein, the term "antigen" or "antigenic peptide" as used herein refers to a compound or composition comprising one or more peptides, polypeptides or proteins which is "antigenic" or "immunogenic" when administered (in an appropriate amount (an "immunogenically effective amount"), i.e., is capable of eliciting, augmenting or boosting a cellular and/or humoral immune response either alone or in combination or linked or fused to another substance (which can be administered at once or over several intervals). Examples of such antigens include, but are not limited to the following: 4-1BB Ligand, 3C (HRV), 4-1BB, 2B4, Apolipoprotein A-II, Activin RIIA, Angiopoietin-like 4, Axl ALCAM Adalimumab ALK-1 Azurocidin Angiopoietin-2 Arginase 1 APRIL Activin A ADAM12 Apo-A1 Activin RIB Adiponectin APCS AIMP1 Annexin A5 ADAM17 Akt1 Angiopoietin-like 3 ANGPTL7 Activin RIIB ADAM8 Alpha-endosulfine BAFFR B7-H4 B7-H3 (4Ig) BAFF Beta-cellulin BMPR-IA BTLA B7-H6 B7-1 BTN3A2 B7-H2 BLAME Bevacizumab BCMA BTN3A1 BTNL3 BTNL9 B3GAT3 Bcl-x B18R BACE-1 BenzNuclease BMP-2 BTN1A1 B7-H5 BTN3A3 B7-H3 B7-H7 B7-2 beta 2-Microglobulin CD3 epsilon CD44 CD55 CD30 ligand CEACAM-8 CD69 CD74 CD99 Cystatin SN Coagulation Factor II Cathepsin B CXADR CADM3 CD27 CD300a CD48 CD72 CD84 CD39 CD98 Chitinase 3-like 1 CNTF R alpha Cystatin SA CTXB Cystatin F Cathepsin S Carboxypeptidase E Coagulation factor XI CD155 CD30 CD3 delta CD3E & CD3G CD4 Carbonic Anhydrase III CD47 CD160 CEACAM-6 CD23 CD200 RI CD300c Chitotriosidase CBLB CLEC10A CD229 CLIC4 C-Reactive Protein Cystatin S CXCR4 Carbonic Anhydrase IX CCL6 CD200 CD37 CD52 CD40 Ligand CD46 CD58 CEACAM-1 CD28H CD68 CA125 CD27 Ligand CD9 Clusterin COMP CTLA-4 Cathepsin L CD2F-10 Choline Kinase beta CD177 CD28 CD300LG CRABP2 CD73 CD83 C1q RI CD31 Cadherin-6 CD163 CNDP1 Cetuximab Carboxypeptidase A4 CD94 Cystatin D CRTAM Complement C5 Cathepsin D Complement Component C5a CD14 CX3CL1 CD133 CD19 CD36 CD3E & CD3D Carbonic Anhydrase XIV CD40 CD117 CD5 CD79B CD96 CG alpha CEACAM-5 CLEC3B Contactin-2 Carboxypeptidase M Cathepsin E CTGF Carbonic Anhydrase II CD20 Full Length CADM1 Complement Factor D CD2 CD34 CD38 DR6 Dinitrophenyl (DNP) DPPII DLL3 DLL1 DR3/TNFRSF25 Dkk-1 DLL4 DPPIV DcR3 Decorin DNAM-1 DDR2 Dkk-3 E-Selectin EGFRvIII EphA7 ErbB4 Ephrin-A1 ENPP-2 Ephrin-A3 EGF R EpCAM Erythropoietin Erythropoietin R E-Cadherin Ephrin-B1 EMMPRIN Ephrin-A4 EGF EphB4 ErbB3 FOLR1 Fc gamma RIIB/CD32b Fetuin A FABP8 FGL1 Fc gamma RI/CD64 Fc gamma RIIIB/CD16b (NA1) Fc gamma RIV/CD16-2 FABP2 FABP6 Fc epsilon RI alpha FGF R5 Frizzled-2 Frizzled-7 FABP3 FKBP12 Frizzled-4 FAM171B Fas Ligand FGF acidic FGF R1 Flt-3 Ligand FOLR2 FcRn (FCGRT & B2M) Furin Fc gamma RIIA/

CD32a Flt-3 Fc gamma RIIIB/CD16b (NA2) FKBP4 FABP1 FABP5 FABP7 Fetuin B Follistatin-like 1 Frizzled-5 Fc gamma RIII/CD16 FAM3B Fumarase Fc gamma RIIIA/CD16a Fas FGF-9 FGF basic FGF R4 G-CSF R GM-CSF GP120 gp130 GFR alpha-like Galactowaldenase G-CSF GFR alpha-2 GPA33 GPD1 Glypican 2 Growth Hormone R Galectin-9 GITR GP120 (HIV) GM-CSF R alpha Gremlin GAPDH GFR alpha-1 GITR Ligand Glypican 3 Growth Hormone Glypican 1 Galectin-4 Galectin-3 Glycoprotein G/G Glycophorin A Glycoprotein/GP (virus) Glycoprotein Glutaredoxin 1 HGF R HSA HABP1 HSP90AAI Hemagglutinin (HA) HE4 Her2 HVEM HMGB1 HAO-1 HGF IL-17A Integrin alpha 2b beta 3 Integrin alpha V beta 6 ICAM-1 IGFBP-3 IL-3 R alpha IgG1 Fc IL-13 R alpha 1 IL-18BP IL-2 R alpha IL-6 IL-8 Integrin alpha 4 beta 7 IL-21 IgG4 Fc IL-12 R beta 1 Integrin alpha V beta 5 Integrin isoform alpha-7X2B beta 1 IFN-gamma IL-17 RC IL-10 IL-12 R beta 1 & IL-12 R beta 2 Integrin alpha V beta 3 IL-17F IL-5 IL-18 R1 IGFBP-7 IL-17E IL-2 R beta IL23A & IL12B IL-4 Integrin alpha 10 beta 1 IL-5 R alpha Integrin alpha V beta 8 IgG3 Fc IL-12B & IL-12A Integrin alpha E beta 7 Integrin alpha 5 beta 1 IL-1 RAcP IL-21 R IL-7 R alpha Integrin alpha D beta 2 IFN-alpha/beta R1 IGF-I R IL-12A IL-1RL1 IL-37 Integrin alpha V beta 1 IL-1 Rrp2 Integrin alpha 4 beta 1 IFN-alpha/beta R2 Integrin alpha 8 beta 1 IGF-II Integrin alpha 9 beta 1 IL-1 beta IL-13 R alpha 2 IL-29 IL-33 IL-6 R alpha IgG2b Fc IGFBP-4 IL-13 Integrin alpha 2 beta 1 IgG2a Fc IgG2 Fc IL-23R IL-17C IDH1 IL-15 R alpha IGF-I IL-31 RA IL-12B IgG4 H Chain IL-17 RA IL-1 RII IL-17 RE IL-2 R gamma IL-4 R alpha IL-7 Integrin alpha 6 beta 1 IL-17A & IL-17F ICAM-2 IFN-gamma R1 IL-20 R beta Integrin alpha L beta 2 IL-27 Ra Insulin R Integrin alpha 11 beta 1 IL-12 R beta 2 ID12 IGFBP-1 IL-22 IL-15 IL-2 Integrin beta 8 ICOS Jagged 1 Jagged 2 Kininogen 1 Kallikrein 6 KIR2DL3 Kallikrein 11 Kallikrein 3 Kallikrein 7 Kallikrein 1 Kallikrein 22 Kallikrein 4 Kallikrein 13 Kallikrein 8 LILRA3 LYPD3 LOXL2 Lipocalin-2 Leptin R LIF R Lipopolysaccharide-binding Latent TGF-beta 1 LRP-5 LRP-6 LILRB2 LTA4H LILRB3 LRRC32 LAIR-1 LAIR-2 LILRB1 LILRA1 LILRA6 Latexin LRP-10 LIGHT LAG-3 LILRA5 LDL R LILRA2 LIF Lumican LILRB4 LTBR LILRB5 LSECtin LAP (TGF-beta 1) LAMP1 LRRC4 MAG/Siglec-4a M-CSF MIS RII MCAM MMP-1 MSR1 Mussel Adhesive Protein MBL MICA MIF MAD2L1 MMP-9 MERTK MIS MMP-2 Mucin-1 M-CSF R Mesothelin Myocilin Neuroligin 3 Nectin-4 NTB-A NCALD Neprilysin Noggin Nectin-3 NKG2D NS1 NKp46 Neuroligin-4, X-linked Neuropilin-1 Nectin-1 Niemann-Pick Type C2 Neuregulin-4 Nectin-2 NKG2A Neuroligin-4, Y-linked NKp30 Neuraminidase (NA) NME1 Osteoprotegerin Osteopontin Oncostatin M OX40 Ligand Olfactory marker protein Osteoactivin OX40 OMgp PTH1R PLA2G1B PSME3 PCSK9 Properdin PD-L1 PPIB Protein L PD-1 & PD-L1 PD-1 PLGF pIgR Prolactin PTP4A2 PDGF R alpha PROCR PSME2 Prolactin R PVRIG PDGF R beta PSCA Protein G P-Selectin PTPRD PD-L2 PH20 PLAU PDGF-BB PSMA Reg4 ROR1 RAGE ROR2 Rituximab RENIN R-Spondin 1 RANK ROBO4 R-Spondin 3 SCARB1 SECTM1 SLC1A5 Serpin A3 S100B Serpin F1 SBDS Sonic Hedgehog SOD1 SIRP gamma Stathmin 1 SUMO1 Siglec-10 SIRP beta SULT1B1 S100A6 SCF Semaphorin 4D Siglec-9 S100A10 Serpin A1 SLAMF7 SULT2B1 SIRP alpha Siglec-3 SLAMF1 S100A1 SCARB2 Semaphorin 4A S100A13 Serpin D1 S100P Serpin H1 Siglec-5 Siglec-6 SOD2 SLITRK6 Syndecan-1 Secretagogin Siglec-15 S100A8 SOST Serpin E2 Siglec-8 Siglec-2 SMAC S100A14 Serpin A8 TSLP R TPBG TrkA Transthyretin Thrombospondin-2 Tau-441 TDGF1 TIM-3 TNF-alpha Transferrin TrkB TFPI THSD1 TIMP-2 TPK1 TRAIL R2 TSLP TGF-beta RII TNFR1 TRAIL R4 TWEAK R TYRO3 Transferrin R TNFSF11 Transferrin R2 TGF-beta 1 TIMP-1 TACI Testican 1 Trastuzumab TROP-2 TFPI-2 TIGIT TNFR2 TRAIL RI Thioredoxin-2 TRAIL UbcH2 UCH-L3 UBE2F uPAR UCH-L1 VAP-B VEGF-B VEGF-D VSIG4 VEGF164 VEGF110 VEGF-C VSIG8 VEGF121 VSIG3 VEGF RI VEGF120 Vasorin VEGF R2 VSIG2 VEGF R3 VLDL R VEGF165 Vitronectin VCAM-1 and YWHAB.

In some embodiments, the compositions can comprise tumor associated antigens, or portions or fragments thereof. In accordance with an embodiment, the present invention provides a synthetic polypeptide comprising an annexin V protein, or a functional portion or fragment or variant thereof, conjugated to an antigen, or a functional portion or fragment or variant thereof.

In accordance with an embodiment, the present invention provides a synthetic polypeptide comprising an annexin V protein, or a functional portion or fragment or variant thereof, conjugated to a tumor associated antigen, or a functional portion or fragment or variant thereof.

In accordance with another embodiment, the present invention provides a synthetic polypeptide comprising an annexin V protein, or a functional portion or fragment or variant thereof, conjugated to a HPV tumor antigen, or a functional portion or fragment or variant thereof.

In accordance with another embodiment, the present invention provides a synthetic polypeptide comprising an annexin V protein, or a functional portion or fragment or variant thereof, conjugated to a CT26 tumor antigen, or a functional portion or fragment or variant thereof.

In accordance with another embodiment, the present invention provides a synthetic polypeptide comprising at the N-terminus, an annexin V protein, or a functional portion or fragment or variant thereof, conjugated to an antigen, or a functional portion or fragment or variant thereof at the C-terminus.

In accordance with another embodiment, the present invention provides a synthetic polypeptide comprising at the C-terminus, an annexin V protein, or a functional portion or fragment or variant thereof, conjugated to an antigen, or a functional portion or fragment or variant thereof at the N-terminus.

In accordance with a further embodiment, the present invention provides a synthetic polypeptide comprising an annexin V protein, or a functional portion or fragment or variant thereof, further comprising a detectable moiety.

In accordance with an embodiment, the present invention provides a nucleic acid composition encoding a synthetic polypeptide comprising any or all of the above embodiments.

In accordance with another embodiment, the present invention provides a nucleic acid composition encoding a synthetic polypeptide, wherein the N-terminal portion of the polypeptide comprises an annexin V protein, or a functional portion or fragment or variant thereof, conjugated to an antigen, or a functional portion or fragment or variant thereof, at the C-terminal portion of the fusion protein.

In accordance with another embodiment, the present invention provides a nucleic acid composition encoding a synthetic polypeptide, wherein the C-terminal portion of the polypeptide comprises an annexin V protein, or a functional portion or fragment or variant thereof, conjugated to an antigen, or a functional portion or fragment or variant thereof, at the N-terminal portion of the fusion protein.

In accordance with a further embodiment, the present invention provides a nucleic acid composition encoding a synthetic polypeptide comprising an annexin V protein, or a functional portion or fragment or variant thereof, conjugated to an antigen, or a functional portion or fragment or variant thereof, and further comprising a detectable moiety.

In accordance with some embodiments, the present invention provides tumor associated antigens that can enhance a cellular immune response, particularly, tumor-destructive CTL reactivity, induced by an epitope of a human pathogen. For example, the tumor antigen, HPV-16 E7 was used as a model antigen for development because human papillomaviruses, particularly HPV-16, are associated with most human cervical cancers. The oncogenic HPV proteins E7 and E6 are important in the induction and maintenance of cellular transformation and co-expressed in most HPV-containing cervical cancers and their precursor lesions. As such, in some of the fusion polypeptide embodiments of the invention, E7 and/or E6 antigens can be used. In a preferred embodiment, the HPV-16 E6 or E7 polypeptide used as an immunogen is substantially non-oncogenic, i.e., it has been mutated and does not bind retinoblastoma polypeptide (pRB) or binds pRB with such low affinity that the HPV-16 E7 polypeptide is effectively non-oncogenic when delivered in vivo, which is accomplished as described herein.

The terms "polypeptide," "protein," and "peptide" include compositions of the invention that also include "analogues," or "conservative variants" and "mimetics" or "peptidomimetics" with structures and activity that substantially correspond to the polypeptide from which the variant was derived.

As used herein, the term "annexin V" means a protein in the annexin superfamily, which has a high affinity for phosphatidylserine (PS). In flow cytometry, annexin V is commonly used to detect apoptotic cells by its ability to bind to phosphatidylserine, a marker of apoptosis when it is on the outer leaflet of the plasma membrane. The function of the protein is unknown; however, annexin V (A5) has been proposed to play a role in the inhibition of blood coagulation by competing for phosphatidylserine binding sites with prothrombin and also to inhibit the activity of phospholipase A1. The gene for Annexin V (ANXV) is located on human chromosome 4q26-q28 and spans a region of DNA 28 kb in length containing 13 exons and 12 introns. The Annexin V mature molecule is a 320 amino-acid residue, 35-36 kDa protein. The protein is folded into a planar cyclic arrangement of four repeats with each repeat composed of 5 alpha-helical segments.

In an embodiment, an Annexin V component of the composition of the present invention comprises the amino acid sequence:

```
                                        (SEQ ID NO: 1)
MAQVLRGTVTDFPGFDERADAETLRKAMKGLGTDEESILTLLTSRSNAQ

RQEISAAFKTLFGRDLLDDLKSELTGKFEKLIVALMKPSRLYDAYELKH

ALKGAGTNEKVLTEIIASRTPEELRAIKQVYEEEYGSSLEDDVVGDTSG

YYQRMLVVLLQANRDPDAGIDEAQVEQDAQALFQAGELKWGTDEEKFIT

IFGTRSVSHLRKVFDKYMTISGFQIEETIDRETSGNLEQLLLAVVKSIR

SIPAYLAETLYYAMKGAGTDDHTLIRVMVSRSEIDLFNIRKEFRKNFAT

SLYSMIKGDTSGDYKKALLLLCGEDD,
``` or a polypeptide having at least 80%, 85%, 90%, 95%, 99% identity with SEQ ID NO: 1.

In accordance with one or more embodiments, the present invention provides a composition comprising a synthetic polypeptide comprising an annexin V protein, or a functional portion or fragment or variant thereof, conjugated to a HPV E6 and/or E7 antigen, or a functional portion or fragment or variant thereof.

As used herein, the term "HPV E6 or E7 tumor antigen" means the HPV oncoprotein E6 or E7, or a functional portion, or fragment or variant thereof, which is required for the induction and maintenance of cellular transformation, and are consistently co-expressed in all HPV-infected, but not normal cells.

In an embodiment, a HPV 16 E6 tumor antigen comprises the amino acid sequence:

(SEQ ID NO: 2)

MHQKRTAMFQDPQERPRKLPQLCTELQTTIHDIILECVYCKQQLLRREV

YDFAFRDLCIVYRDGNPYAVCDKCLKFYSKISEYRHYCYSLYGTTLEQQ

YNKPLCDLLIRCINCQKPLCPEEKQRHLDKKQRFHNIRGRWTGRCMSCC

RSSRTRRETQL, or a polypeptide having at least 80%, 85%, 90%, 95%, 99% identity with SEQ ID NO: 2.

In an embodiment, a HPV 18 E6 tumor antigen comprises the amino acid sequence:

(SEQ ID NO: 3)

MARFEDPTRRPYKLPDLCTELNTSLQDIEITCVYCKTVLELTEVFEFAF

KDLFVVYRDSIPHAACHKCIDFYSRIRELRHYSDSVYGDTLEKLINTGL

YNLLIRCLRCQKPLNPAEKLRHLNEKRRFHNIAGHYRGQCHSCCNRARQ

ERLQRRRETQV, or a polypeptide having at least 80%, 85%, 90%, 95%, 99% identity with SEQ ID NO: 3.

In an embodiment, a HPV 16 E7 tumor antigen comprises the amino acid sequence:

(SEQ ID NO: 4)

MHGDTPTLHEYMLDLQPETTDLYCYEQLNDSSEEEDEIDGPAGQAEPDR

AHYNIVTFCCKCDSTLRLCVQSTHVDIRTLEDLLMGTLGIVCPICSQKP, or a polypeptide having at least 80%, 85%, 90%, 95%, 99% identity with SEQ ID NO: 4.

In an embodiment, a HPV 18 E7 tumor antigen comprises the amino acid sequence:

(SEQ ID NO: 5)

MHGPKATLQDIVLHLEPQNEIPVDLLCHEQLSDSEEENDEIDGVNHQHL

PARRAEPQRHTMLCMCCKCEARIELVVESSADDLRAFQQLFLNTLSFVC

PWCASQQ, or a polypeptide having at least 80%, 85%, 90%, 95%, 99% identity with SEQ ID NO: 5.

The term "functional portion" when used in reference to a antigenic epitope refers to any part or fragment, which part or fragment retains the biological activity of which it is a part (the parent molecule, antibody, or antigen). Functional portions encompass, for example, those parts that retain the ability to specifically bind to the antigen (e.g., in an MHC-independent manner), or detect, treat, or prevent the disease, to a similar extent, the same extent, or to a higher extent, as the parent molecule. In reference to the parent molecule, the functional portion can comprise, for instance, about 10%, 25%, 30%, 50%, 68%, 80%, 90%, 95%, or more, of the parent molecule.

The functional portion can comprise additional amino acids at the amino or carboxy terminus of the portion, or at both termini, which additional amino acids are not found in the amino acid sequence of the parent molecule. Desirably, the additional amino acids do not interfere with the biological function of the functional portion, e.g., specifically binding to a cancer antigen, having the ability to detect cancer, treat or prevent cancer, etc. More desirably, the additional amino acids enhance the biological activity, as compared to the biological activity of the parent molecule.

By "protein" is meant a molecule comprising one or more polypeptide chains.

In this regard, the invention also provides a synthetic polyprotein molecule comprising at least one of the polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof. Suitable methods of making fusion proteins are known in the art, and include, for example, recombinant methods. See, for instance, Choi et al., *Mol. Biotechnol.* 31: 193-202 (2005).

Included in the scope of the invention are functional variants or fragments of the inventive fusion proteins, and polypeptides, and proteins described herein. The term "functional variant" as used herein refers to fusion proteins, polypeptides, or proteins having substantial or significant sequence identity or similarity to a parent fusion proteins, polypeptides, or proteins, which functional variant retains the biological activity of the fusion proteins, polypeptides, or proteins of which it is a variant. In reference to the parent fusion proteins, polypeptides, or proteins, the functional variant can, for instance, be at least about 30%, 50%, 75%, 80%, 90%, 98% or more identical in amino acid sequence to the parent fusion proteins, polypeptide, or protein.

The functional variant or fragment can, for example, comprise the amino acid sequence of the parent fusion proteins, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc Alternatively or additionally, the functional variants or fragments can comprise the amino acid sequence of the parent fusion proteins, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent fusion proteins, polypeptide, or protein.

In accordance with another embodiment, the present invention provides a synthetic polypeptide comprising an annexin V protein, or a functional portion or fragment or variant thereof, conjugated to a HPV 16 E7 tumor antigen, or a functional portion or fragment or variant thereof, at the C-terminal portion of the fusion protein.

In accordance with one or more embodiments, the synthetic polypeptide comprises the amino acid sequence:

(SEQ ID NO: 6)

MAQVLRGTVTDFPGFDERADAETLRKAMKGLGTDEESILTLLTSRSNAQ

RQEISAAFKTLFGRDLLDDLKSELTGKFEKLIVALMKPSRLYDAYELKH

ALKGAGTNEKVLTEIIASRTPEELRAIKQVYEEEYGSSLEDDVVGDTSG

YYQRMLVVLLQANRDPDAGIDEAQVEQDAQALFQAGELKWGTDEEKFIT

IFGTRSVSHLRKVFDKYMTISGFQIEETIDRETSGNLEQLLLAVVKSIR

SIPAYLAETLYYAMKGAGTDDHTLIRVMVSRSEIDLFNIRKEFRKNFAT

SLYSMIKGDTSGDYKKALLLLCGEDDEFMHGDTPTLHEYMLDLQPETTD

LYCYEQLNDSSEEEDEIDGPAGQAEPDRAHYNIVTFCCKCDSTLRLCVQ

STHVDIRTLEDLLMGTLGIVCPICSQKP, or a polypeptide having at least 80%, 85%, 90%, 95%, 99% identity with SEQ ID NO: 6.

It will be understood by those of ordinary skill in the art, that the fusion protein or polypeptide of the present invention can have more than one arrangement of the annexin V peptide and the E7 peptide, including, for example, having the E7 peptide at the N-terminal portion of the fusion polypeptide.

It will be understood by those of ordinary skill in the art, that the fusion protein or polypeptide of the present invention can incorporate a linker between the annexin V peptide and the E7 peptide.

In some embodiments, the linker comprises one or more amino acids, including, for example, 1 to 5 amino acids in length. In an embodiment, the linker is a dipeptide. In another embodiment, the linker is the dipeptide Glu-Phe.

In accordance with a further embodiment, the present invention provides a composition comprising a synthetic polypeptide comprising an annexin V protein, or a functional portion or fragment or variant thereof, conjugated to a HPV 16 E7 tumor antigen, or a functional portion or fragment or variant thereof, and further comprising a detectable moiety.

By "detectable label(s) or moieties" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens. Specific radioactive labels include most common commercially available isotopes including, for example, $^3$H, $^{11}$C, $^{13}$C, $^{15}$N, $^{18}$F, $^{19}$F, $^{123}$I, $^{124}$I, $^{125}$I, $^{131}$I, $^{86}$Y, $^{89}$Zr, $^{111}$In, $^{94m}$Tc $^{99m}$Tc, $^{64}$Cu and $^{68}$Ga. Suitable dyes include any commercially available dyes such as, for example, 5(6)-carboxyfluorescein, IRDye 680RD maleimide or IRDye 800CW, ruthenium polypyridyl dyes, and the like. In some embodiments, the dye is a fluorescent dye, including for example, Alex-Fluor NHS dyes which are conjugated to the synthetic polypeptide via covalent bonding of the ester of the dye to a primary amine of the synthetic polypeptide.

In some embodiments, the present invention comprises the AnnE7 fusion polypeptide covalently linked to a detectable moiety.

In accordance with yet another embodiment, the present invention provides a composition comprising a synthetic polypeptide comprising an annexin V protein, or a functional portion or fragment or variant thereof, conjugated to a HPV 16 E7 tumor antigen, or a functional portion or fragment or variant thereof, and further comprising a biologically active agent.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc.

Specific examples of useful biologically active agents include: anti-neoplastics, such as androgen inhibitors, anti-metabolites, cytotoxic agents, and immunomodulators; biologicals, such as peptides, polypeptides, proteins and amino acids, hormones, interferons or cytokines and other bioactive peptidic compounds.

In accordance with an embodiment, the present invention provides a nucleic acid composition encoding synthetic polypeptide comprised of an annexin V protein, or a functional portion or fragment or variant thereof, conjugated to a HPV 16 E7 tumor antigen, or a functional portion or fragment or variant thereof.

The fusion polypeptides, and/or proteins of the invention (including functional portions and functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, NY 2001; and Ausubel et al., Current Protocols in Molecular Biology, Greene Publishing Associates and John Wiley & Sons, NY, 1994. Further, some of the fusion proteins, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the fusion proteins, polypeptides, and/or proteins described herein (including functional portions and functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive fusion proteins, polypeptides, and proteins can be synthetic, recombinant, isolated, and/or purified.

In some embodiments, the synthetic polypeptides can comprise one or more histidine residues on either N or C terminal ends, or both. Histidine residues are known to be useful for purification of expressed proteins. Examples of such residues or his-tags include nucleic acids which encode six histidine residues in a row (SEQ ID NO: 16) or a poly-his, or 6×his tag (SEQ ID NO: 16).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a bacterial vector, e.g., a pET plasmid vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the fusion proteins, polypeptide, or protein (including functional portions and functional variants thereof), or to the nucleotide sequence which is complementary to or which hybridizes to the nucleotide sequence encoding the fusion proteins, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

In accordance with another embodiment, the present invention provides a nucleic acid composition encoding a synthetic polypeptide comprising an annexin V protein, or a functional portion or fragment or variant thereof, conjugated to a HPV 16 E7 tumor antigen, or a functional portion or fragment or variant thereof, at the C-terminal portion of the fusion protein.

In accordance with a further embodiment, the present invention provides a nucleic acid composition encoding a synthetic polypeptide comprising an annexin V protein, or a functional portion or fragment or variant thereof, conjugated to a HPV 16 E7 tumor antigen, or a functional portion or fragment or variant thereof, and further comprising a detectable moiety.

In accordance with an embodiment, the present invention provides a method for treating a tumor in a subject comprising administering to the subject an effective amount of a composition comprising a synthetic polypeptide comprising an annexin V protein, or a functional portion or fragment or variant thereof, conjugated to a HPV 16 E7 tumor antigen, or a functional portion or fragment or variant thereof.

The fusion proteins of the present invention can be formulated into a composition, such as a pharmaceutical composition. In this regard, the invention provides a pharmaceutical composition comprising any of the fusion proteins, polypeptides, proteins, functional portions, functional variants, nucleic acids, expression vectors, and a pharmaceutically acceptable carrier. The inventive pharmaceutical compositions containing any of the inventive fusion proteins can comprise more than one fusion protein.

In accordance with still another embodiment, the present invention provides a method for treating cancer in a subject, comprising administering to the subject, a therapeutically effective amount of the synthetic polypeptides described above, at least one or more therapeutic agents, and a pharmaceutically acceptable carrier.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound (s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular fusion proteins, as well as by the particular method used to administer the fusion proteins. Accordingly, there are a variety of suitable formulations of the pharmaceutical composition of the invention. The following formulations for aerosol, parenteral, subcutaneous, intraperitoneal, vaginal and rectal, administration are exemplary and are in no way limiting. More than one route can be used to administer the fusion proteins, and in certain instances, a particular route can provide a more immediate and more effective response than another route.

It will be appreciated by one of skill in the art that, in addition to the above-described pharmaceutical compositions, the synthetic polypeptides of the invention can be formulated as inclusion complexes, such as cyclodextrin inclusion complexes, or liposomes.

The pharmaceutical compositions of this invention including biologically active fragments, variants, or analogs thereof, can be administered by any suitable routes including intracranial, intracerebral, intraventricular, intrathecal, intraspinal, oral, topical, rectal, transdermal, subcutaneous, intravenous, intramuscular, intranasal, and the like. In one embodiment, the compositions are added to a retained physiological fluid, such as cerebrospinal fluid, blood, or synovial fluid. The compositions of the invention can be amenable to direct injection or infusion at a site of disease or injury.

As noted above, compositions of the invention can be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, cited herein.

For example, pharmaceutical compositions according to the invention may be in the form suitable for sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

Suitable dosage forms can be formulated for, but are not limited to, oral, rectal, sublingual, mucosal, nasal, ophthalmic, subcutaneous, intramuscular, intravenous, transdermal, spinal, intrathecal, intra-articular, intra-arterial, sub-arach-noid, bronchial, lymphatic, and intra-uterille administration, and other dosage forms for systemic delivery of active ingredients. In a preferred embodiment, the dosage form is suitable for injection or intravenous administration.

To prepare such pharmaceutical dosage forms, one or more of the aforementioned compounds are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

Compositions for parenteral use may be provided in unit dosage forms (e.g., in single-dose ampules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. The composition may include suitable parenterally acceptable carriers and/or excipients.

In one approach, a therapeutic of the invention is provided within an implant, such as an osmotic pump, or in a graft comprising appropriately transformed cells. Methods of introduction may also be provided by rechargeable or biodegradable devices. Various slow release polymeric devices have been developed and tested for the controlled delivery of drugs, including proteinacious biopharmaceuticals. A variety of biocompatible polymers (including hydrogels), including both biodegradable and non-degradable polymers, can be used to form an implant for the sustained release of a bioactive factor at a particular target site.

Generally, the amount of administered agent of the invention (dosage) will be empirically determined in accordance with information and protocols known in the art.

Compositions of the invention can comprise various pharmaceutically acceptable salts, ether derivatives, ester derivatives, acid derivatives, and aqueous solubility altering derivatives of the active compound. The present invention can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

In some embodiments, the pharmaceutically acceptable carrier comprises more than 90%, more than 80%, more than 70%, more than 60%, more than 50%, more than 40%, more than 30%, more than 20%, more than 10%, more than 9%, more than 8%, more than 6%, more than 5%, more than 4%, more than 3%, more than 2%, more than 1%, more than 0.5%, more than 0.4%, more than 0.3%, more than 0.2%, more than 0.1%, more than 0.09%, more than 0.08%, more than 0.07%, more than 0.06%, more than 0.05%, more than 0.04%, more than 0.03%, more than 0.02%, more than 0.01%, more than 0.009%, more than 0.008%, more than 0.007%, more than 0.006%, more than 0.005%, more than 0.004%, more than 0.003%, more than 0.002%, more than 0.001%, more than 0.0009%, more than 0.0008%, more than 0.0007%, more than 0.0006%, more than 0.0005%, more than 0.0004%, more than 0.0003%, more than 0.0002%, or more than 0.0001% of the pharmaceutical composition by w/w, w/v or v/v.

In some embodiments, the concentration of the compound in the composition comprises less than 100%, less than 90%, less than 80%, less than 70%, less than 60%, less than 50%, less than 40%, less than 30%, less than 20%, less than 10%, less than 9%, less than 8%, less than 6%, less than 5%, less than 4%, less than 3%, less than 2%, less than 1%, less than 0.5%, less than 0.4%, less than 0.3%, less than 0.2%, less than 0.1%, less than 0.09%, less than 0.08%, less than 0.07%, less than 0.06%, less than 0.05%, less than 0.04%, less than 0.03%, less than 0.02%, less than 0.01%, less than 0.009%, less than 0.008%, less than 0.007%, less than 0.006%, less than 0.005%, less than 0.004%, less than 0.003%, less than 0.002%, less than 0.001%, less than 0.0009%, less than 0.0008%, less than 0.0007%, less than 0.0006%, less than 0.0005%, less than 0.0004%, less than 0.0003%, less than 0.0002%, or less than 0.00010% of the pharmaceutical composition by w/w, w/v or v/v.

In some embodiments, the concentration of the compound is in the range of about 0.0001% to about 50%, about 0.001% to about 40%, about 0.01% to about 20%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 210%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12%, about 1% to about 10% of the pharmaceutical composition by w/w, w/v or v/v.

In some embodiments, the concentration of the compound is in the range of about 0.0001% to about 5%, about 0.001% to about 4%, about 0.01% to about 2%, about 0.02% to about 1%, or about 0.05% to about 0.5% of the pharmaceutical composition by w/w, w/v or v/v.

In some embodiments, the amount of the compound in the pharmaceutical composition is about 0.00001 mg, 0.0001 mg, 0.001 mg, 0.005 mg, 0.01 mg, 0.05 mg, 0.1 mg, 0.25 mg, 0.5 mg, 1 mg, 2 mg, 4 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 1.1 g, 1.2 g, 1.3 g, 1.4 g, 1.5 g, 1.6 g, 1.7 g, 1.8 g, 1.9 g, 2 g, 2.5 g, 3 g, 3.5 g, 4 g, 4.5 g, 5 g, 6 g, 7 g, 8 g, 9 g, or 10 g.

For purposes of the invention, the amount or dose of the synthetic polypeptides administered should be sufficient to effect, e.g., a therapeutic or prophylactic response, in the subject or animal over a reasonable time frame. For example, the dose of the synthetic polypeptides should be sufficient to bind to a target antigen, or detect, treat or prevent an infection in a period of from about 2 hours or longer, e.g., 12 to 24 or more hours, from the time of administration. In certain embodiments, the time period could be even longer. The dose will be determined by the efficacy of the particular polypeptides and the condition of the animal (e.g., human), as well as the body weight of the animal (e.g., human) to be treated. In some embodiments, the amount of the synthetic polypeptide of the present invention administered to a subject is in the range of about 1 µg to 1 mg, including, for example, 10, 20, 50, 100, 200 300, and 500 µg as a dose.

In accordance with one or more embodiments, the present invention provides a treatment regimen for treating a hyperproliferative disease in a subject suffering from such a disease comprising treating the subject with one or more of the synthetic polypeptides including the AnnV peptide, the HPV16/18 E7 long peptide and/or the AnnV-E7 fusion peptide after the subject has previously been treated with a chemotherapeutic agent.

In accordance with a further embodiment, the present invention provides a synthetic polypeptide as described above or pharmaceutical compositions comprising the same, for treating a hyperproliferative disease in a subject, characterized in that a therapeutically effective amount of the synthetic polypeptide as described above or the pharmaceutical compositions comprising the same is administered to the subject in one or more doses after the subject receives one or more doses of a chemotherapeutic agent.

As used herein, the term "therapeutic agent" or "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids, including, for example, alkylating antineoplastic agents, such as carboplatin and cisplatin; nitrosourea alkylating antineoplastic agents, such as carmustine (BCNU); antimetabolite antineoplastic agents, such as methotrexate; pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; *vinca* alkaloid natural antineoplastics, such as vinblastine and vincristine.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a proliferative disease. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

In accordance with a further embodiment, the inventive methods further comprises administering to the subject a pharmaceutical composition comprising an effective amount of one or more additional checkpoint inhibitors.

In some embodiments, the checkpoint inhibitor is a composition the blocks the checkpoint protein, programmed cell death protein 1 (PD-1). Examples of such inhibitors include, pembrolizumab, nivolumab, MPDL3280A, MED14736, AMP-514, MSB0010718C, anti-TGF-0, anti-PD-1, anti-PD-L1, or anti-TIM-3, a depleting anti-CTLA-4 antibody or monoclonal antibody which binds the protein CTLA-4, which is expressed on the surface of activated T lymphocytes and blocks the binding of the antigen-presenting cell blocks the binding of the antigen-presenting cell ligands B7.1 and B7.2 to CTLA-4, resulting in inhibition of B7-CTLA-4-mediated downregulation of T-cell activation, and which has a depleting effect on $T_{reg}$ cells..

In some embodiments, the one or more checkpoint inhibitors are administered with the comprises an annexin V protein, or a functional portion or fragment or variant thereof, conjugated to an antigen, or a functional portion or fragment or variant thereof, concurrently or serially.

For example, in accordance with some embodiments, the inventive compositions can be used to treat hyperproliferative diseases, including cancer.

In some embodiments, the treatment comprises treating a subject suffering from a hyperproliferative disease, wherein said subject was previously treated with a biologically active agent for 1 to 10 days, with an annexin V protein, or a functional portion or fragment or variant thereof, conjugated to an antigen, or a functional portion or fragment or variant thereof.

In some embodiments, the antigen is a tumor antigen. In some other embodiments, the antigen is a tumor antigen derived from the patients' tumor.

In some embodiments, the subject suffering from a hyperproliferative disease is treated with one or more biologically active agents, such as chemotherapeutic agents, for example, cisplatin, doxorubicin, and/or cyclophosphamide.

In some embodiments the one or more biologically active agents, or chemotherapeutic agents are given intratumorally or intravenously to the subject, 1 to 10 days prior to treating the subject with an annexin V protein, or a functional portion or fragment or variant thereof, conjugated to an antigen, or a functional portion or fragment or variant thereof.

With reference to the time period between the subject receiving one or more biologically active agents, such as chemotherapeutic agents and the subject receiving an annexin V protein, or a functional portion or fragment or variant thereof, conjugated to an antigen, or a functional portion or fragment or variant thereof, the period of time can be 1 day, 2, 3, 4, 5, 6, 7, 8, 9, up to 10 days.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with another embodiment, the present invention provides a method for treating a proliferative disease in a subject comprising administering to the subject an effective amount of a composition comprising a synthetic polypeptide comprising an annexin V protein, or a functional portion or fragment or variant thereof, conjugated to a HPV tumor antigen, or a functional portion or fragment or variant thereof.

As stated herein, the subtype of HPV used in the inventive methods can be selected from HPV types 16, 18, 31, 33, 35, 39, 45, 51, 52, and 58. In some embodiments, the HPV subtype is 16 and/or 18.

In some embodiments, the composition administered comprises a synthetic polypeptide comprising an annexin V protein, or a functional portion or fragment or variant thereof, conjugated to a HPV 16 or 18 tumor antigen, or a functional portion or fragment or variant thereof.

In addition, as stated herein, the tumor antigens from HPV used in the inventive methods include oncoproteins E6 and E7.

In some embodiments, the composition administered comprises a synthetic polypeptide comprising an annexin V protein, or a functional portion or fragment or variant thereof, conjugated to a HPV 16 or 18 E6 and/or E7 antigen, or a functional portion or fragment or variant thereof.

As used herein, the term "proliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis. In accordance with one or more embodiments, the term cancer can include, for example cancers of the lung, liver, pancreas, prostate, breast and central nervous system, including glioblastomas and related tumors; cervical, vulvar, vaginal, penile, oral, throat, oropharyngeal, and anal cancers.

As used herein, the term "proliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis. In accordance with one or more embodiments, the term cancer can include, for example cancers of the lung, liver, pancreas, prostate, breast and central nervous system, including glioblastomas and related tumors.

In accordance with a further embodiment, the present invention provides a method for treating a tumor in a subject comprising administering to the subject an effective amount of a composition comprising a synthetic polypeptide comprising an annexin V protein, or a functional portion or fragment or variant thereof, conjugated to a HPV 16 E7 tumor antigen, or a functional portion or fragment or variant thereof, and at least one additional biologically active agent.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se, as well as pharmaceutically acceptable, pharmacologically active salts, esters, amides, prodrugs, metabolites, analogs etc.

In a further embodiment, the compositions and methods of the present invention can be used in combination with one or more additional therapeutically active agents which are known to be capable of treating conditions or diseases discussed above. For example, the compositions of the present invention could be used in combination with one or more known therapeutically active agents, to treat a proliferative disease such as a tumor or cancer. Non-limiting examples of other therapeutically active agents that can be readily combined in a pharmaceutical composition with the compositions and methods of the present invention are enzymatic nucleic acid molecules, allosteric nucleic acid molecules, antisense, decoy, or aptamer nucleic acid molecules, antibodies such as monoclonal antibodies, small molecules, and other organic and/or inorganic compounds including metals, salts and ions.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated. By way of example, and not intending to limit the invention, the dose of the pharmaceutical compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In some embodiments, the dosage of the inventive compositions is between about 1 mg to about 500 mg.

The dose of the compositions of the present invention also will be determined by the existence, nature and extent of any adverse side effects that might accompany the administration of a particular composition. Typically, an attending physician will decide the dosage of the pharmaceutical composition with which to treat each individual subject, taking into consideration a variety of factors, such as age, body weight, general health, diet, sex, compound to be administered, route of administration, and the severity of the condition being treated.

As used herein, the terms "effective amount" or "sufficient amount" are equivalent phrases which refer to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease, such as a neoplastic disease or tumor In accordance with one or more embodiments, it was shown that the inventive fusion polypeptides have the ability to target thrombin-activated (FIG. 1) and tumor-activated platelets (FIG. 3) both ex vivo and in vivo. Additionally, the inventive fusion polypeptides are able to target the tumor antigen for its delivery to cancer and, in some embodiments, tumors, such as TC-1 tumors (FIG. 4) in a platelet-dependent fashion. Without being held to any particular theory, it was shown that the targeting of cancers using the inventive fusion polypeptides (FIG. 5) induces high levels of tumor antigen (E7)-specific T cells, inhibiting tumor growth, and extending the survival of tumor-bearing mice (FIG. 6). The inventors used platelet depletion and CD40L KO experiments that abolished the fusion polypeptides' anti-tumor responses (FIG. 7), to show that the fusion polypeptides of the present invention enhance CD8+ T cell-mediated anti-tumor immunity through platelet-derived CD40L expression on tumor-activated platelets.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, +100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

"At least" a certain value is understood as that value or more. For example, "at least 10," is understood as "10 or more"; "at least 20" is understood as "20 or more." As used herein, "less than" a specific value is understood to mean that value and less. For example "less than 10" is understood to mean "10 or less."

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

EXAMPLES

Exemplary Plasmid DNA constructs and preparation.

The plasmid pET28a-annexinV was constructed by PCR using template annexinV (from Addgene, Cambridge, MA) and primers (TTTGGATC-CATGGCACAGGTTCTCAGAGG (SEQ ID NO: 7) and AAAgaattcGTCATCTTCTCCACAGAGCA (SEQ ID NO: 8)). The PCR fragment was cloned into BamHI and EcoRI sites of pET28a vector. The pET28a-annexinV-E7 plasmid was constructed by PCR using template pcDNA3-E7 and primers (AAAGAATTCATGCATGGAGATACACCTACA (SEQ ID NO: 9) and TTTCTCGAGTGGTTTCT-GAGAACAGATGGGGC (SEQ ID NO: 10)). The PCR fragment was cloned into EcoRI and XhoI sites of pET28a-annexinV. pET28-AnnV, pET28-AnnV-E7, pET28-AnnV-AH5, and pET28-AnnV-Gluc DNA plasmids were generated, confirmed by sequencing, and transformed into *Escherichia coli* (BL21(DE3)). Expression of the fusion protein was induced with 1 mM isopropyl-b-D-thiogalacto-pyranoside (IPTG) at 37° C. for 5 hours. Recombinant protein was purified by Ni+ affinity chromatography (Ni-NTA agarose, Qiagen) according to the manufacturer's protocol. Briefly, cell supernatant was loaded in 2 ml of Ni+ affinity chromatography that is equilibrated with washing buffer (50 mM $NaH_2PO_4$, 300 mM NaCl, and 20 mM imidazole, pH 8.0) and then washed with 20 ml washing buffer. For the elution of binding protein, 10 ml of elution buffer (50 mM $NaH_2PO_4$, 300 mM NaCl, and 250 mM imidazole, pH 8.0) was used. The eluted protein was collected and analyzed using 10-15% gradient SDS-PAGE and Coomassie brilliant blue staining. The purity of proteins was characterized by limulus amoebocyte lysate (LAL) (Lonza) and Picogreen assays (Invitrogen). The endotoxin level of each protein was less than 0.01 EU/mg, and the bacterial DNA level was 0.1 ng/mg of protein in independent preparations.

Cells.

As previously described, TC-1 cells express the HPV16 E6 and E7 proteins, as well as the activated RAS oncogene (23). CT 26 murine colon carcinoma cells were purchased from ATCC. The generation of E7(aa49-57)-specific and OVA-specific CD8+ T cells have been previously described (40). Cells were grown in RPMI 1640, supplemented with 10% (v/v) fetal bovine serum, 50 units/mL of penicillin/streptomycin, 2 mM L-glutamine, 1 mM sodium pyruvate, 2 mM non-essential amino acids, and 0.1% (v/v) 2-mercaptoethanol at 37° C. with 5% $CO_2$.

BMDCs or BMDM were obtained by culturing monocytes harvested from the bone marrow of C57BL/6 mice in RPMI10 medium supplemented with 2 mM Granulocyte-macrophage colony-stimulating factor (GM-CSF) or DMEM/F12 medium (Biowest) supplemented with 10% fetal bovine serum, 50 units/ml of penicillin/streptomycin, 15Mm Hepes and 50 ng/ml macrophage colony-stimulating factor (M-CSF)), respectively, at 37° C. with 5% $CO_2$. The monocytes were incubated for 6 days before experimentation.

Mice.

Female C57BL/6 mice were purchased from Charles Rivers Laboratories (Frederick, MD) or Orient Bio Inc., and female CD40L knockout mice (B6.129S2-Cd40lgtm1lmx/J) were purchased from the Jackson Laboratory (Bar Harbor, ME). All mice were maintained under specific pathogen-free conditions at the Johns Hopkins University School of Medicine Animal Facility (Baltimore, MD). All animal procedures were performed according to protocols approved by the Johns Hopkins or Konkuk University Institutional Animal Care and Use Committee. $2 \times 10^5$ TC-1 cells in 50 µL of PBS were subcutaneously injected into 6- to 8-week old female C57BL/6 mice or CD40L knockout mice. Equimolar amounts of AnnE7 (100 µg/injection), annexin V protein (70 µg/injection), and E7 protein (30 µg/injection) in PBS were intravenously injected into mice on days 5, 8 and, 11 after TC-1 tumor inoculation. For platelet depletion experiments, the mice received 1 mg/kg anti-CD41 antibodies on days 5, 8 and, 11 and AnnE7 on days 6, 9 and, 12 after TC-1 tumor inoculation.

Platelet Isolation and Treatment.

Mouse peripheral blood were collected into 500 µL of citrate-dextrose solution (ACD) from the ventral arteries of mice tails while platelet-rich plasma was collected by centrifugation at 200 g for 10 min. Platelet-rich plasma was centrifuged at 2000 g for 10 min, and the pellet was suspended in a modified Tyrode's solution (134 mM NaCl, 2.9 mM KCl, 0.34 mM $Na_2PO_4$, 12 mM $NaHCO_3$, 20 mM HEPES, 1 mM $MgCl_2$, 5 mM glucose, and 2.5 mM $CaCl_2$)). $1 \times 10^8$ platelets/mL were activated with 5 units/mL of thrombin for 15 min at 37° C. Tumor-activated platelets were isolated form TC-1 tumor-bearing mice, and tumors were harvested when their diameters reached 10 cm. Tumors were then minced into 1- to 2-mm pieces, and filtered through a 70-µm nylon cell strainer. The filtered tumor mixture was centrifuged at 200 g for 10 min to remove tumor cells and tumor-infiltrating lymphocytes. Platelet-rich supernatant was centrifuged at 2000 g for 10 min, and pellets were suspended in modified Tyrode's solution. For platelets and TC-1 cell-binding experiments, $1 \times 10^7$ platelets were co-cultured with $1 \times 10^5$ TC-1 cells for 15 min at 37° C., then analyzed by fluorescence-activated cell sorting (FACS).

In Vivo Fluorescence Imaging.

For the fluorescence imaging, E7, annexin V, and AnnE7 proteins were labeled with an Alexa Fluor® 647 dye according to the manufacturer's instruction (Thermo Fisher Scientific). Equimolar amounts of Alexa 647 labeled E7, annexin V, and AnnE7 proteins were intravenously injected into mice through tail vein as previously described. After 24 hours, mice were euthanized, and imaged by the IVIS® Spectrum in vivo imaging system series 2000 (PerkinElmer). The excitation maximum of Alexa fluor 647 occurs at 650 nm and the emission maximum occurs at 665 nm. After imaging, tumors were immediately harvested, washed with PBS, and imaged by the IVIS® Spectrum machine.

Flow Cytometry Analysis.

For the platelet staining, platelets were washed with modified Tyrode's solution. The platelets were initially stained with purified anti-mouse CD16/32 (Fc block, BioLegend), followed by staining with FITC-conjugated anti-mouse CD61, PE-conjugated anti-mouse CD62p, PE-conjugated anti-mouse CD40L, or APC-conjugated annexin V in the modified Tyrode solution. For peripheral blood mononuclear cell (PBMC) and tumor-infiltrating lymphocyte (TIL) staining, cells were washed with a FACS washing buffer containing phosphate-buffered saline (PBS) with 0.5% bovine serum albumin (BSA). Following Fc blocking, cells were stained with FITC-conjugated anti-mouse CD8a, PE-conjugated anti-mouse CD45, PE-conjugated HPV16 E7aa49-57 peptide loaded H-2Db E7 tetramer or APC-conjugated anti-mouse CD8a antibody. After washing with modified Tyrode solution or FACS wash buffer, platelets or PBMCs were acquired with a FACSCalibur flow cytometer (BD Biosciences) and analyzed using the FlowJo software (TreeStar Inc.).

Tumor-Infiltrating Lymphocytes Isolation.

Tumor-bearing mice were euthanized and their tumor tissues were surgically removed. Tumors were minced into 1 to 2 mm pieces and washed with complete RPMI-1640 medium. Tumor pellet was digested with serum-free RPMI-1640 medium containing 0.05 mg/mL collagenase I, 0.05 mg/mL collagenase IV, 0.025 mg/mL hyaluronidase IV, 0.25 mg/mL DNase I, 100 U/mL penicillin, and 100 µg/mL streptomycin and incubated at 37° C. with periodic agitation. The tumor digest was then filtered through a 70-µm nylon filter mesh to remove undigested tissue fragments. The resultant single tumor cell suspensions and TILs were washed with PBS containing 0.5% BSA.

Detection of CD40L by ELISA.

Peripheral blood samples were collected into 100 µL PBS containing 0.5 mM EDTA from naive or TC-1 tumor-bearing mice. The plasma was collected by centrifugation at 2000 g for 20 min. Tumor explant supernatants were prepared from primary TC-1 tumors. The tumor tissues were minced into 1- to 2-mm pieces and suspended with 500 µL PBS. The tumor suspension was centrifuged at 2000 g for 20 min, the cell free supernatants were collected and kept at –80° C. CD40L ELISA was performed using the CD40L (soluble) Mouse ELISA Kit (Thermo Fisher Scientific) according to manufacturer's instructions. Briefly, 50 µL of plasma or tumor explant supernatants were mixed with 50 µL sample diluent, the sample mixtures were added to anti-mouse CD40L antibody pre-coated plate. Biotin-conjugated CD40L capture antibodies were subsequently added to the plate, and incubated for 2 hrs at room temperature. After washing the plates with PBS containing 0.05% Tween-20, they were further incubated with Streptavidin-HRP for 1 hr at room temperature. After washing, the plates were developed with TMB Substrate Solution and stopped by Stop Solution containing 1 M Phosphoric acid.

In Vivo Tumor Treatment Experiments

For in vivo tumor treatment experiment, $2 \times 10^5$ TC-1 cells or $5 \times 10^5$ CT 26 cells were injected subcutaneously into C57BL/6 or BALB/c mice (10 per group), respectively. 5 mg/kg Cisplatin (Sigma-Aldrich, Germany) or 10 mg/kg doxorubicin was administered via intraperitoneal injection on days 12 and 15. 20 µg/mice of E7 long peptide (AGQAE-PDRAHYNIVTFCCKCDS) (SEQ ID NO: 11) were injected intratumorally on days 13 and 16. 3.5ug/mice of E7 49-57 peptide (RAHYNIVTF) (SEQ ID NO: 12) or AH5 peptide (SPSYAYHQF) (SEQ ID NO: 13) were injected intravenously into the lateral tail vein on days 13, 14, 16, and 17. 200 µg/mice of Annexin V, Annexin V-E7, or Annexin V-AH5 were injected intravenously into the lateral tail vein on days 13, 14, 16, and 17. 200 µg/mice of anti-TGF-β (clone 1D11.16.8) or anti-TNF-α (clone XT3.118) antibodies (BioXcell, USA) were injected intraperitoneally on days 10, 12, 14, 16, and 18. 200 µg/mice of anti-PD-1 (clone RMP1-14), anti-PD-L1 (clone 10F.9G2), or anti-TIM-3 (clone RMT3-23) antibodies (BioXcell, USA) were injected intraperitoneally on days 13, 14, 16, and 17.

For in vivo CD8 depletion experiment, C57BL/6 mice (5 per group) were injected subcutaneously with $2\times10^5$ TC-1 cells on day 0.5 mg/kg Cisplatin was administered via intraperitoneal injection on days 12 and 15. 200 μg/mice of Annexin V-E7 was injected intravenously into the lateral tail vein on days 13, 14, 16, and 17. 100 μg/mice of anti-CD8 (clone 2.43) or control IgG (Rat IgG2b, clone LTF-2) antibodies (BioXcell, USA) were injected intraperitoneally daily from day 12 to day 20.

For late combination treatment experiment, $2\times10^5$ TC-1 cells were injected subcutaneously into C57BL/6 mice (10 per group). 5 mg/kg cisplatin (Sigma-Aldrich, Germany) was injected intraperitoneally on days 15 and 18. 200 μg of AnnV-E7 protein was injected intravenously on days 16, 17, 19, and 20. 200 μg/mice anti-PD-1, anti-PD-L1, or anti-TIM3 antibodies were injected intraperitoneally on days 21, 23, and 25.

Following tumor challenge, mice were monitored for evidence of tumor growth by palpation and inspection twice a week until they were died.

In Vitro T Cell Activation and Proliferation Assay

Splenocytes of C57BL/6 mice were harvested and labeled via incubation with 5 μM CFSE solution (Thermo Fisher, USA) for 15 minutes at 37° C. $2\times10^6$ CFSE labelled splenocytes were then incubated with anti-CD3α mAb (Invitrogen, USA) or PMA (Sigma-Aldrich, Germany) plus Ionomycin (Sigma-Aldrich, Germany) in the presence of Phosphatidyl-serine and/or annexinV protein. 24 hours after incubation, the supernatants were harvested and assessed for IFN-γ cytokine level using ELISA. 3 days after incubation, the number of CFSE+ cells was analyzed using flow cytometry.

For OVA specific T cell activation experiment, splenocytes from OT-1 mouse were harvested and stimulated 1 μg/ml OVA peptide (SIINFEKL) (SEQ ID NO: 14) for 7 days. CD8+ T cells were isolated from splenocytes using CD8+ T cell MicreBeads (MACS Miltenyi Biotec, Germany), incubated with 5 μM CFSE solution (Thermo Fisher, USA) for 15 minutes at 37° C. $1\times10^6$ CFSE labelled CD8+ T cells were then co-cultured with OVA expressing TC-1 cells treated with or without cisplatin, with or without concurrently 20 μg/ml AnnexinV protein treatment. 24 hours after incubation, the supernatants were harvested and assessed for IFN-γ cytokine level using ELISA. 3 days after incubation, the number of CFSE+ cells was analyzed using flow cytometry.

Analysis of Systemic Antigen-Specific CD8+ T Cell Response

For tetramer staining, PBMCs (peripheral blood mononuclear cells) were harvested 1 week after the last protein injection and prepared as described (Cancer Res 71, 5601-5605 (2011)). After RBC lysis, single cells were stained with Phycoerythrin-labeled H-2Db HPV16 E7 (RAHYNIVTF) (SEQ ID NO: 12) tetramer (Beckman Coulter, Hialeah, FL) and anti-CD8 antibody, and analyzed by flow cytometry.

For intracellular cytokine staining, splenocytes from each vaccination group were harvested 1 day or 1 week after the last protein injection. $5\times106$ pooled splenocytes from each vaccination group were incubated with 1 μg/ml E7 49-57 peptide (RAHYNIVTF) (SEQ ID NO: 12) or AH5 423-431 peptide (SPSYVYHQF) (SEQ ID NO: 15) and 1 μl/ml GolgiPlug (BD Cytofix/Cytoperm Kit) for 16 hours. Cells were then harvested, stained for CD8 and IFN-7 using a previously described standard protocol. Samples were analyzed on a FACSCalibur flow cytometer, using CellQuest software (Becton Dickinson, San Jose, CA). All of the analyses shown were carried out with gated lymphocyte populations.

Tumor Microenvironment Cell Analysis

Tumors were surgically, dissected, washed twice with PBS, and digested using gentleMACS dissociator (Miltenyi Biotec, Germany) and MACS tumor dissociation kits (Miltenyi Biotec, Germany) with standard protocol. The digested tumor was filtered through a 100 um cell strainer, followed by centrifugation. The cells were then washed twice using PBS. Remaining red blood cells were lysed using ACK solution.

To assess the presence of T cell population, cells were stained with PE-conjugated anti-CD8 (53-6.7/biolegend) or CD4 antibodies(GK1.5/invitrogen). To assess the MDSCs population, cells stained with PE-conjugated anti-CD11b (M1/70/invitrogen) and FITC-conjugated anti-Gr1 antibodies(RB6-8C5/invitrogen). To assess M1 and M2 macrophage population, cell were stained with APC-conjugated F4/80(BM8/invitrogen) and FITC-conjugated CD206 antibodies(C068C2/biolegend). To assess the presence of regulatory T cells, cells were stained with PE-cy7-conjugated anti-CD4(RM4-5/invitrogen) and APC-conjugated anti-CD25 antibodies(PC61.5/invitrogen) at 4° C. for 30 minutes, washed with PBS, incubated in Fixation/Permeabilization working solution at 4° C. for 20 minutes, and stained for PE-conjugated anti-Foxp3 antibodies(FJK-16S/invitrogen). To assess the expression of PD-L1 by immune cells and tumor cells, cells were stained with FITC-conjugated anti-CD45 antibodies(30-F11/invitrogen) and PE-conjugated anti-PD-L1 antibodies(10F.9G2/invitrogen). To assess the tumor-infiltrating antigen-specific CD8+ T cell population, cells were incubated with 1 ug/ml E7 49-57 peptide (RAHYNIVTF) (SEQ ID NO: 12) and 1 μl/ml GolgiPlug (BD Cytofix/Cytoperm Kit) for 16 hours followed by surface CD8 and intracellular IFN-γ via previously described standard protocol. All samples were analyzed using FACSCalibur flow cytometer.

ELISA

For in vivo cytokine analyze, harvested tumor tissues were chopped and resuspended on ice in RIPA protein extraction solution (50 nmol/L Tris-Cl [pH 8.0], 150 nmol/L NaCl, 1 mmol/L phenylmethylsulphonyl fluoride [PMSF], 0.1% sodium dodecyl sulphate [SDS], 1% Nonidet P-40 [NP-40] and 0.5 mmol/L EDTA) for 2 hours and centrifuged at 13000 rpm for 15 min. Supernatant protein concentrations were determined by Bradford protein assay. The levels of TNF-α and IL-10 cytokines in 1 mg of proteins from each treatment groups were quantified using a mouse Ready-Set-Go ELISA kit (Invitrogen, USA) following manufacturer's recommendations. The TGF-β cytokine levels were measured used a Mouse TGF-beta ELISA kit (R&D system, USA). All results were measured with a plate reader.

For in vitro cytokine analysis, $1\times10^5$ of TC-1 tumor cells were treated with or without 20 μg/ml of cisplatin for 6 hours, and all tumor cells were harvested and washed twice with PBS. Apoptotic tumor cells were treated with $1\times10^5$ of bone-marrow derived dendritic cell or bone marrow derived macrophage with or without 20 μg/ml AnnexinV protein for 24 hours. After co-culture, acquired supernatant were quantitated as mentioned above.

In Vitro Recombinant Protein Functional Test $2\times10^5$ of TC-1 tumor cells were treated with 5 μg/ml of cisplatin for 18 hours and washed to remove residual cisplatin. The cells were then treated with 0.5 μg/ml of FITC-labeled recombinant AnnexinV or AnnexinV-E7 protein, or commercially available FITC-AnnexinV (BD, USA), and analyzed by flow cytometry analysis.

Luciferase-Based Bioluminescence Imaging

*Gaussia* luciferase (Gluc) and the substrate coelenterazine (Sigma-Aldrich, Germany) were used to test for Gluc activity in vivo. For the in vivo bioluminesence experiment, mice were injected with $1 \times 10^5$ TC-1 cells. 10 days after tumor challenge, mice were treated with 5 μg/ml of cisplatin via intraperitoneal injection. 2 days after cisplatin treatment, 200 μg of Gluc or AnnV-Gluc protein was injected intravenously. 1 day after Gluc or AnnV-Gluc injection, luciferin substrate was injected intraperitoneally and the bioluminescence of the cells was detected via IVIS Spectrum Imaging System Series 2000. The region of interest from displayed images was designated and quantified as total photon counts using Living Image 2.50 software (Xenogen).

Statistical Analysis.

The statistical analyses were performed with GraphPad Prism V.6 software (La Jolla, CA). All data values and error bars are mean±SD and are representative of at least two separate experiments. Kaplan-Meier survival plots were constructed to estimate survival percentage. Results for intracellular cytokine staining with flow cytometry analysis and tumor treatment experiments were evaluated by analysis of variance (one-way ANOVA) and the Turkey-Kramer multiple comparison test. Comparisons between individual data points were made using Student's t-tests. Survival distributions for mice in different groups were compared through Kaplan-Meier survival curves, and by use of the log-rank tests. All P values <0.05 were considered significant. Of note, *,  and * indicate P values less than 0.05, 0.01, and 0.001, respectively; N.S., not significant.

Example 1

The exemplary synthetic fusion polypeptide AnnE7 specifically binds to thrombin-activated platelets.

Figure 1A:
FIG. 1 illustrates thrombin-activated platelets increase
annexin V and AnnE7 binding. (1A) Schematic diagram of
one embodiment of the present invention comprising HPV
16 E7 tumor antigen-linked annexin V fusion protein
(AnnE7). (1B) SDS-PAGE analysis for purified E7, annexin
V (Ann) and AnnE7. (M: molecular weight markers given in
kD). (1C) Flow cytometric analyses of platelet activation
through AnnE7 binding on either unstimulated platelets or
thrombin-activated platelets. Platelets were treated with 10
μg/mL of Alexa647-labeled AnnE7, 7 μg/mL of Alexa647-
labeled Ann, or E7 protein in combination with 5 units/mL
of thrombin for 30 minutes. Untreated (thrombin) platelets
served as control groups. (1D) Flow cytometric analyses of
Alexa647-labeled protein binding. Following a wash, plate-
lets were stained with PE-conjugated anti-His and FITC-
conjugated anti-mouse CD61 antibodies.
Figure 1B:
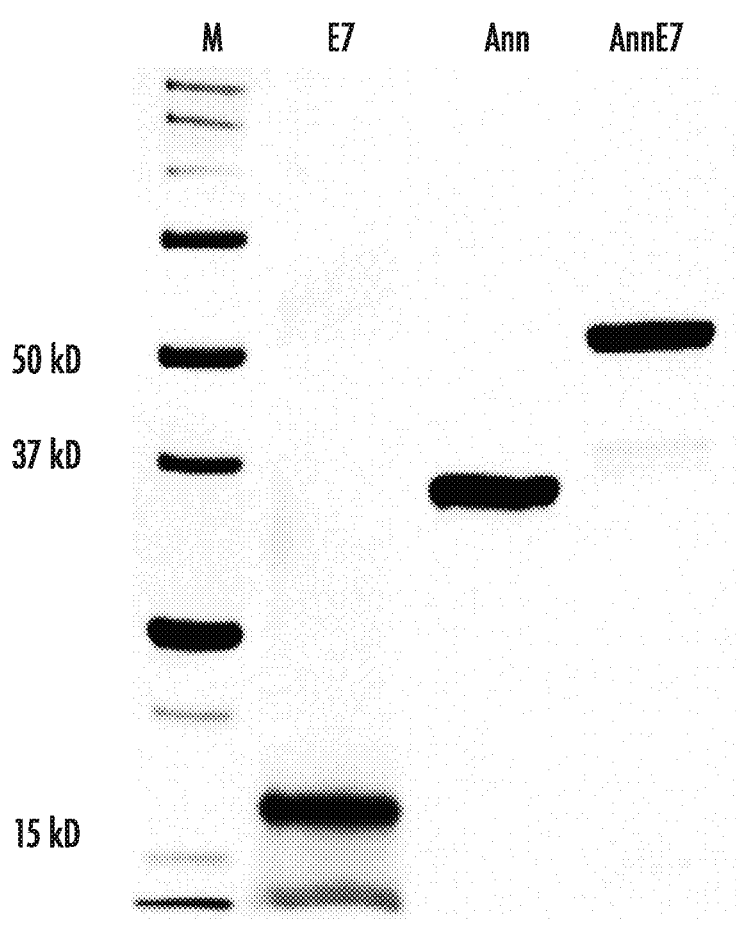
Figure 1C:
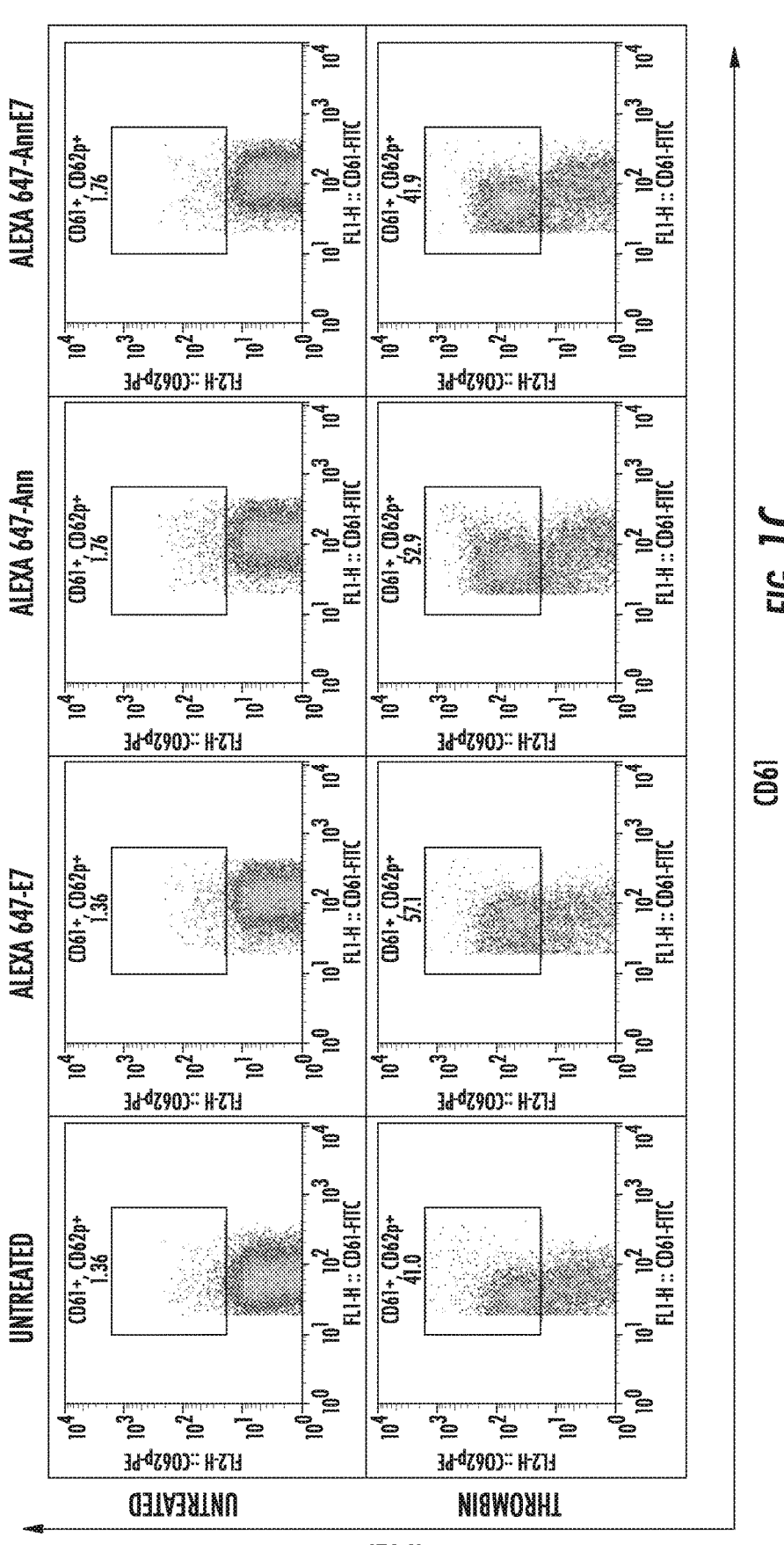
Figure 1D:
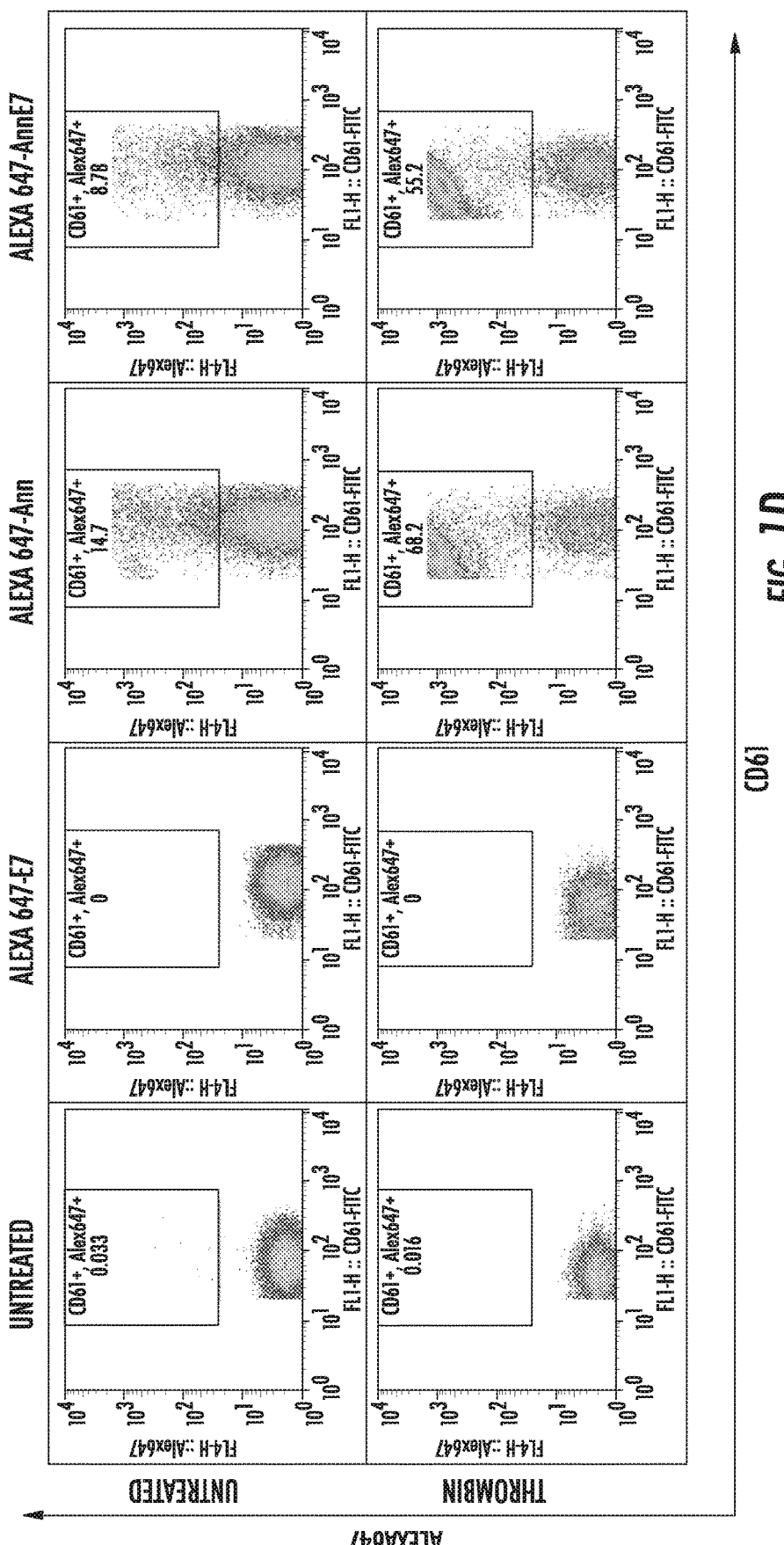

Platelet activation induces phosphatidylserine (PS) exposure, which is targeted by annexin V. Consistent with previous studies ((18); for review see (24)), we have shown that thrombin-activated platelets increase annexin V binding (data not shown). Specifically, we observed an increased expression of CD62P, a marker of platelet aggregation, and CD40L, expressed on activated platelets, in thrombin-activated platelets, in addition to a noticeable increase in annexin V binding to thrombin-activated platelets (data not shown). Using these results, we developed a novel chimeric protein consisting of the HPV16 E7 tumor antigen fused with annexin V (AnnE7) (FIGS. 1A-B). To test whether AnnE7 specific target activated platelets, we treated thrombin-activated platelets or untreated platelets with Alexa 647-labeled E7, annexin V, or AnnE7. Under thrombin-activated conditions, both AnnE7 and annexin V increase the binding of platelets (FIG. 1C). In contrast, the E7 protein did not bind to activated platelets (FIG. 1D). We verified that under thrombin-activated conditions, AnnE7 expression increased (data not shown). These results show that the AnnE7 fusion protein exhibited specific targeting abilities to activated platelets by linking the E7 antigen with annexin V in vitro.

Example 2

Annexin V binds to tumor-activated platelets with high affinity.

Figure 2A:
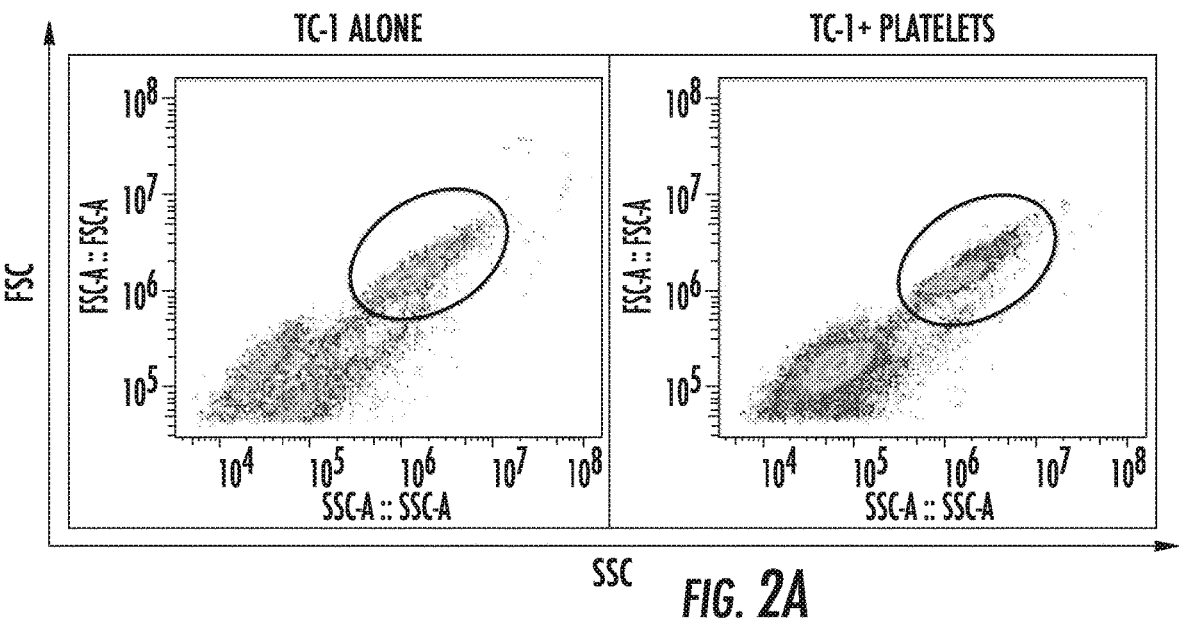
FIG. 2 illustrates that TC-1 cells induce platelet activation
and increase annexin V binding to platelets. TC-1 cells were
mixed with platelets for 15 min. Following a wash, cells
were stained with CD61, CD62P, and annexin V. (2A)
Representative flow cytometric images of TC-1 or TC-1-
platelet aggregates, indicated by black circles indicate TC-1
or TC-1-platelets aggregates. (2B) Representative flow cyto-
metric images of CD62P and CD61 expressions on TC-1 or
TC-1-platelet aggregates. (2C) Histogram of CD61 expres-
sion on TC-1 cells. (2D) Histogram of CD62P expression on
TC-1. (2E) Representative flow cytometric images of
annexin V and CD61 expression on TC-1 or TC-1-platelet
aggregates. (F) Histogram of annexin V expression on TC-1.
Figure 2B:
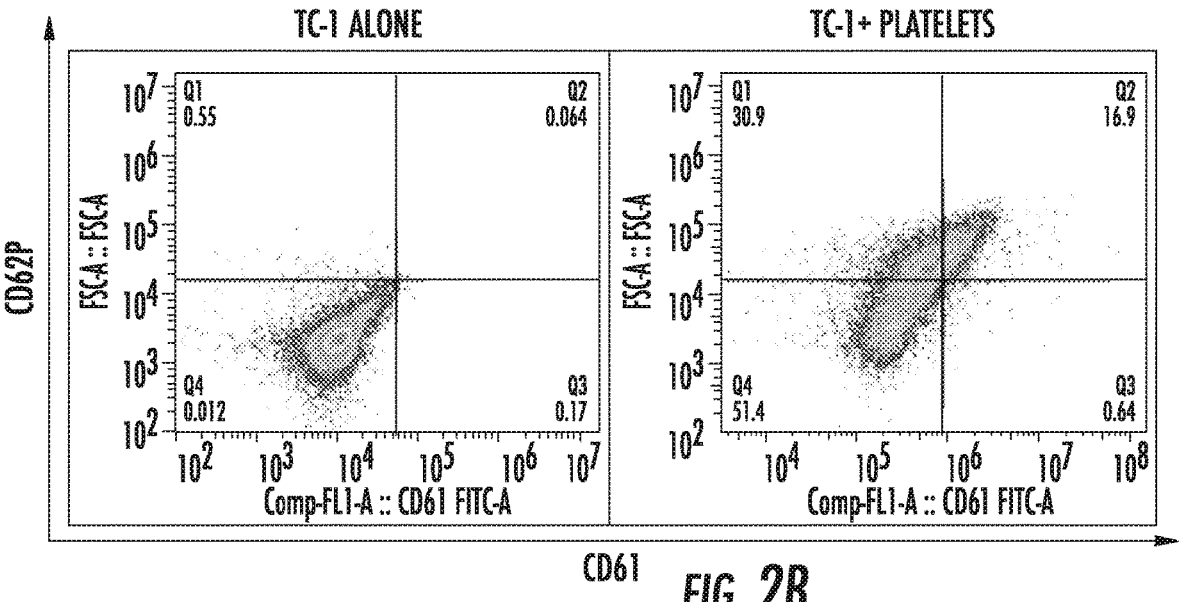
Figures 2C, 2D, 2E, 2F:
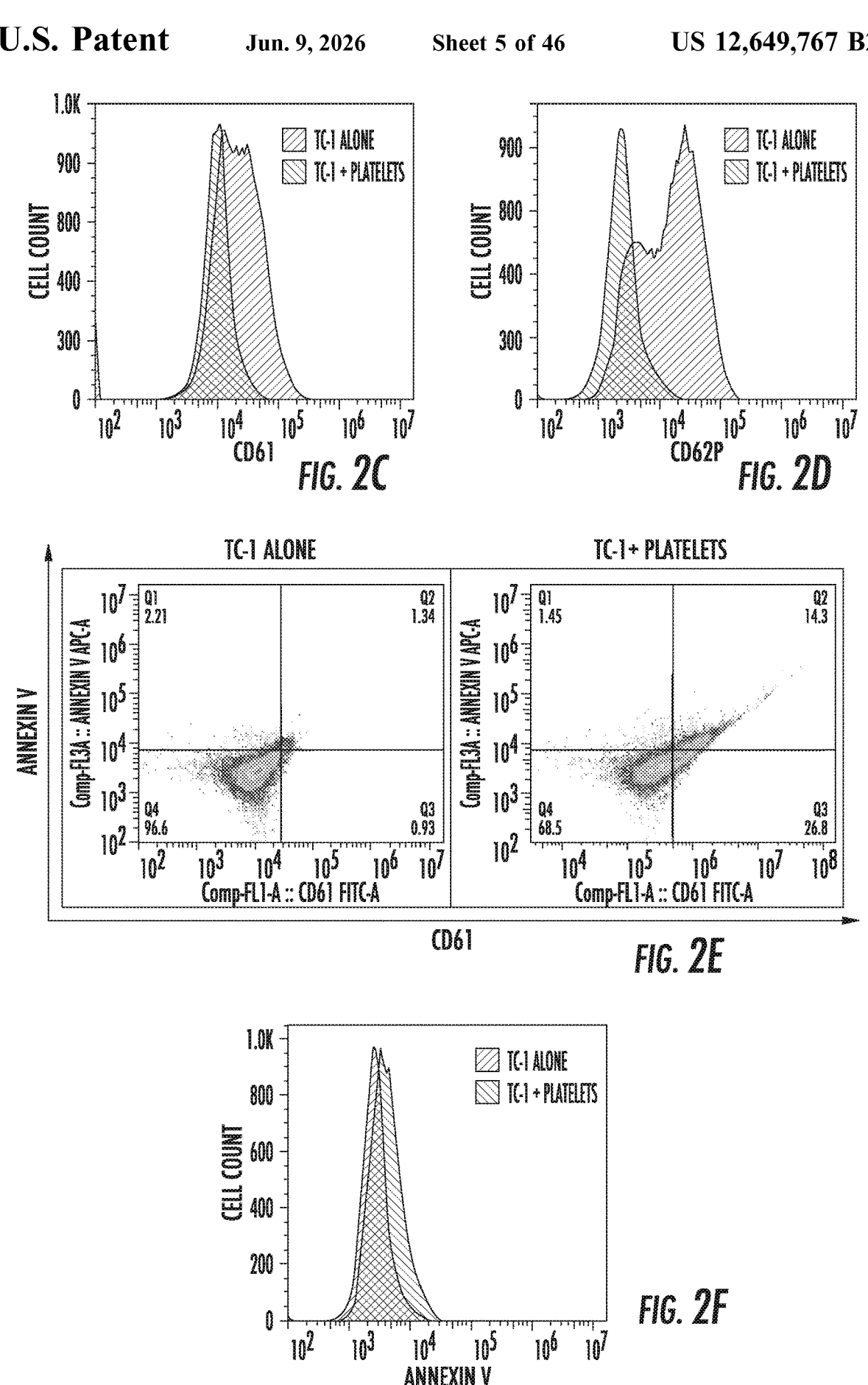
Figures 3A, 3B:
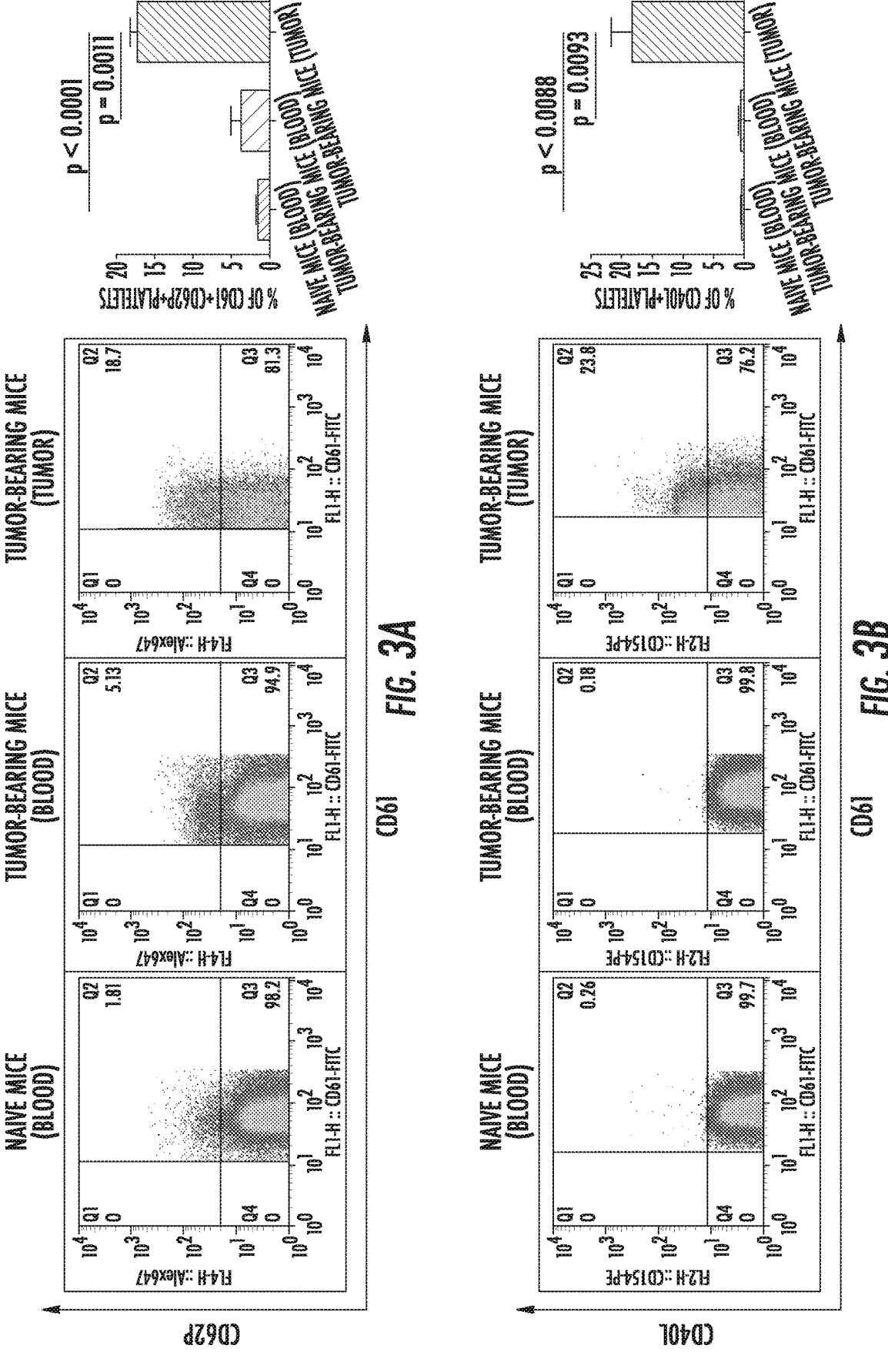
FIG. 3 shows that annexin V has a higher affinity for
tumor-activated platelets. Platelets were collected form
naive C57BL/6 mice or tumor-bearing mice (n=3). Tumor-
activated platelets were collected form tumor tissues. Plate-
lets and tumor-associated platelets were stained with (3A)
CD62P, (3B) CD40L, or (3C) annexin V. Shown here are
representative flow cytometry images and bar graph sum-
mary of flow cytometric analyses.
Figure 3C:
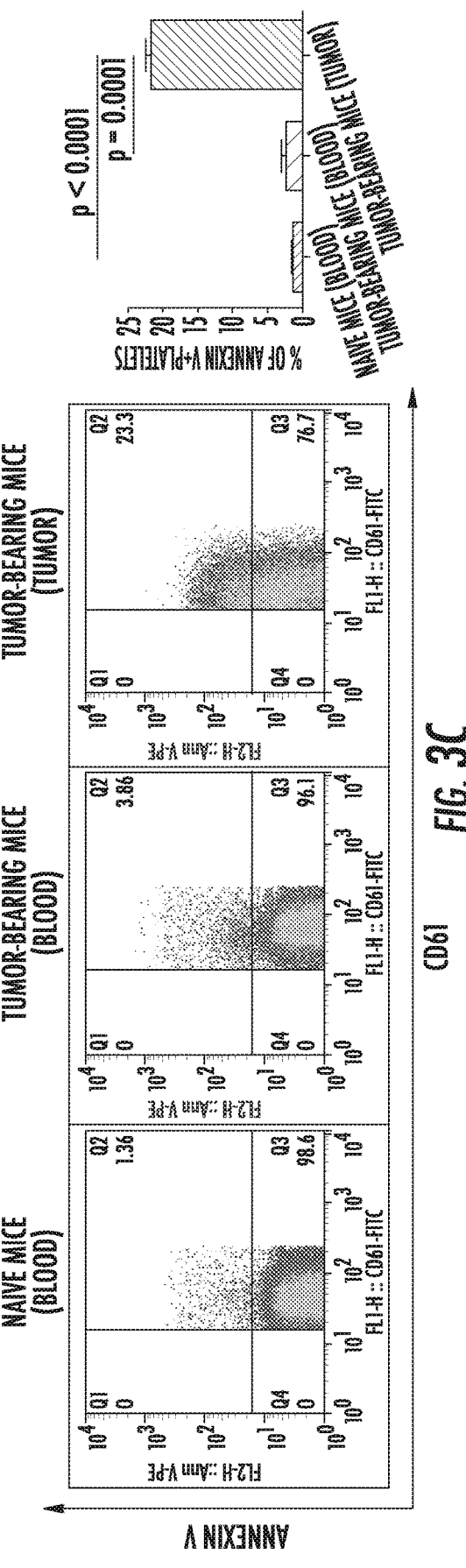

Tumor cells aggregate with platelets and induce platelet activation. The aggregation of platelets and tumor cells protects tumors from immune detection and provides cancer cells with an immune escape mechanism. Here, we show that TC-1 cells bind to platelets and induce platelet activation (FIGS. 2A-D). In addition, tumor cells are coated with more annexin V after TC-1 cells are mixed with platelets (FIGS. 2E-F). As we have demonstrated that thrombin-activated platelets increase the binding of annexin V, we then determined whether this binding is affected by the presence of tumor cells. Platelets isolated from blood or tumors extracted from tumor-bearing mice were compared to platelets of naive mice (FIG. 3). Tumor-activated platelets isolated from tumors exhibited significantly higher levels of CD62P and CD40L compared to the platelets from the peripheral blood of naive or tumor-bearing mice (FIG. 3A-B). Tumor-activated platelets also exhibited significantly higher levels of annexin V binding (FIG. 3C). These results suggest that tumor-activated platelets are more active and have a higher affinity for annexin V. Therefore, tumor-activated platelets are a potent target for the AnnE7 and coating the E7 antigen on the TC-1 tumor cells.

Example 3

The synthetic fusion polypeptide AnnE7 has the ability to target tumors through annexin V in vivo.

Figure 4E:
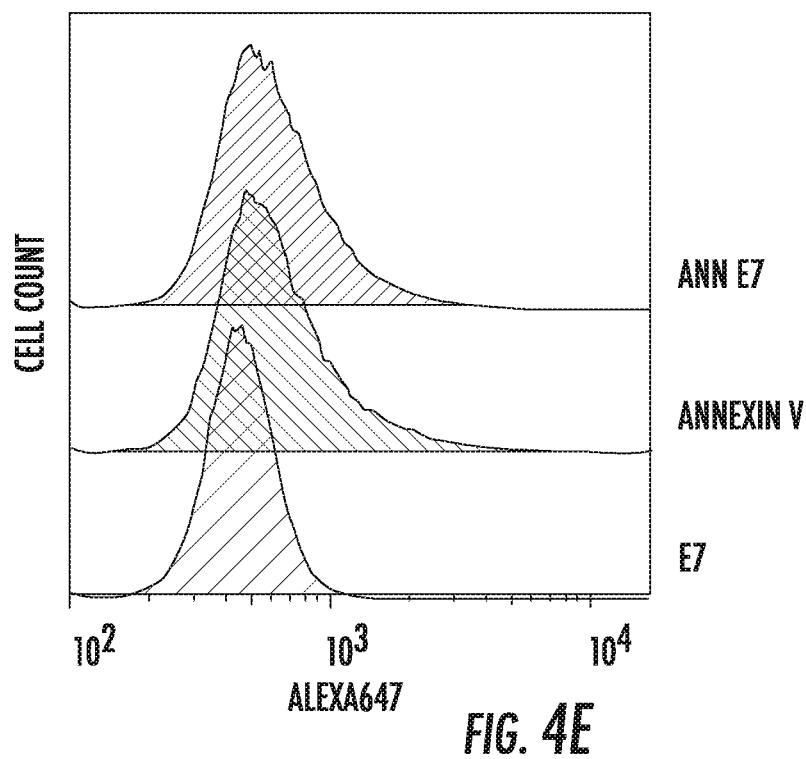
Figure 4F:
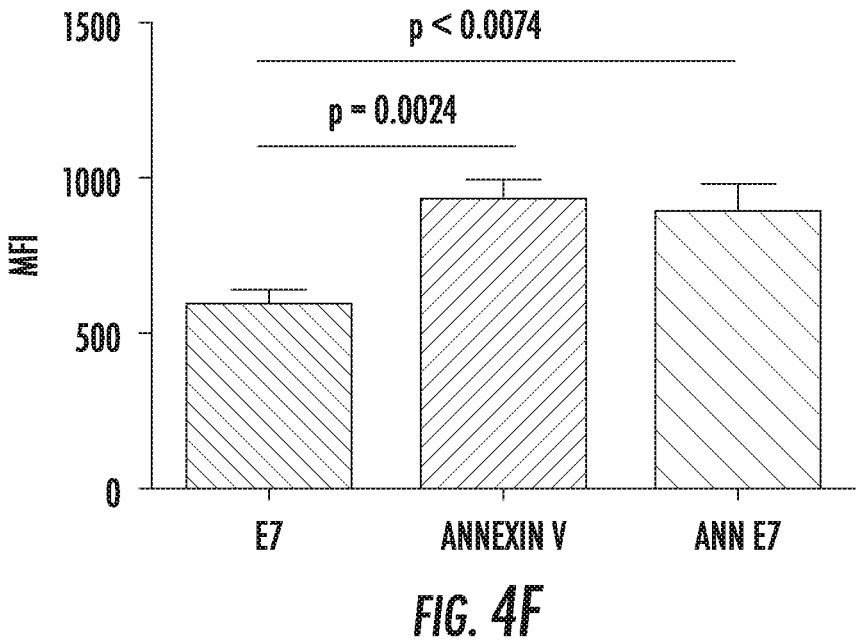

It was previously shown that platelets facilitate tumor cell evasion from immune surveillance by aggregating with tumor cells and modulating major histone compatibility complex (MHC) class I expressions on them (25, 26). Therefore, coating the antigens on the tumor cells though tumor-associated platelets can help immune cells more efficiently recognize and kill them. For this purpose, we determined whether AnnE7 would be able to target tumors and coat the E7 antigen on TC-1 tumor cells (FIG. 4). TC-1 tumor-bearing mice were injected with either Alex-647 labeled E7, annexin V, or AnnE7. In vivo fluorescence imaging indicates that both of AnnE7 and annexin V more efficiently accumulate in the tumors, but the E7 protein alone did not (FIGS. 4A-D). This finding is further supported by flow cytometric data of the minced tumors, in which AnnE7 and annexin V both revealed higher levels of binding on tumor cells than the E7 protein alone (FIGS. 4E-F). These data suggest that the ability for AnnE7 to targets tumor cells is dependent on annexin V.

Example 4

AnnE7 is able to generate tumor-activated platelet-dependent anti-tumor immunity and prolong survival.

Figure 5A:
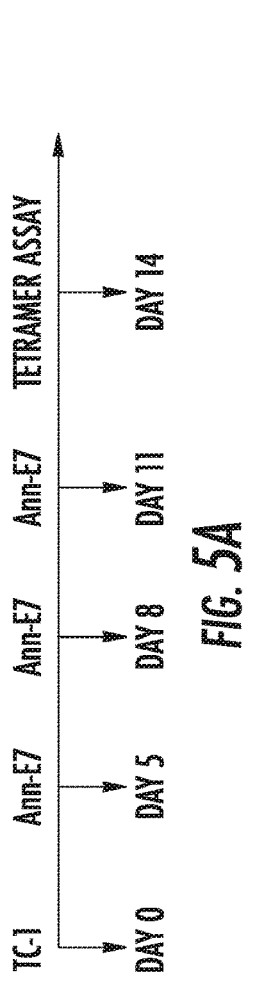
Figure 5B:
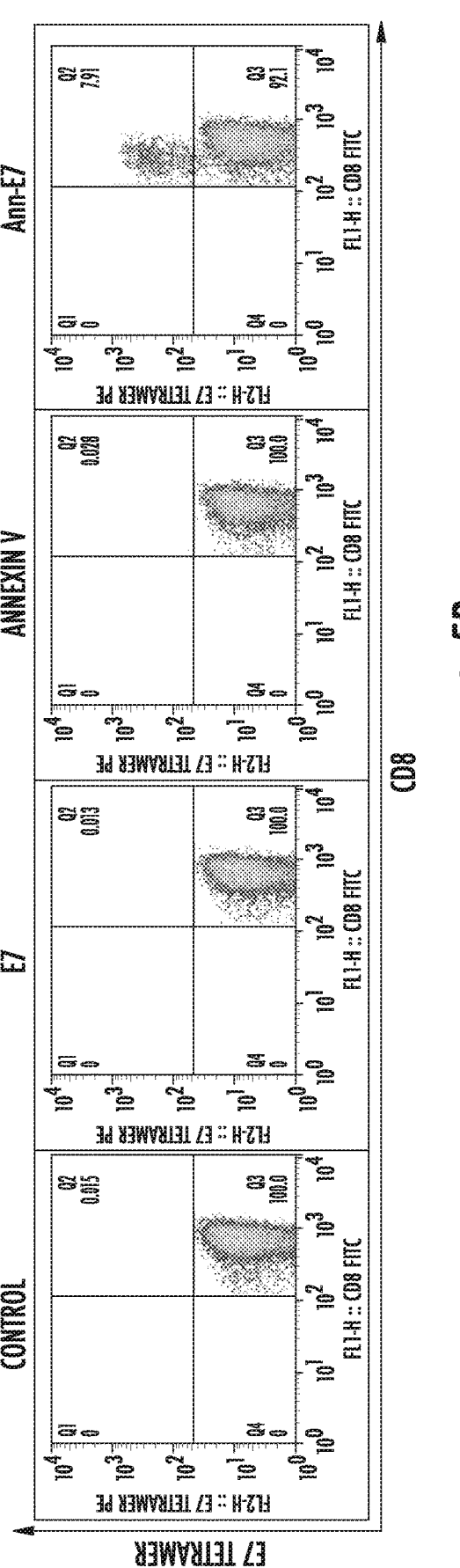
Figure 5C:
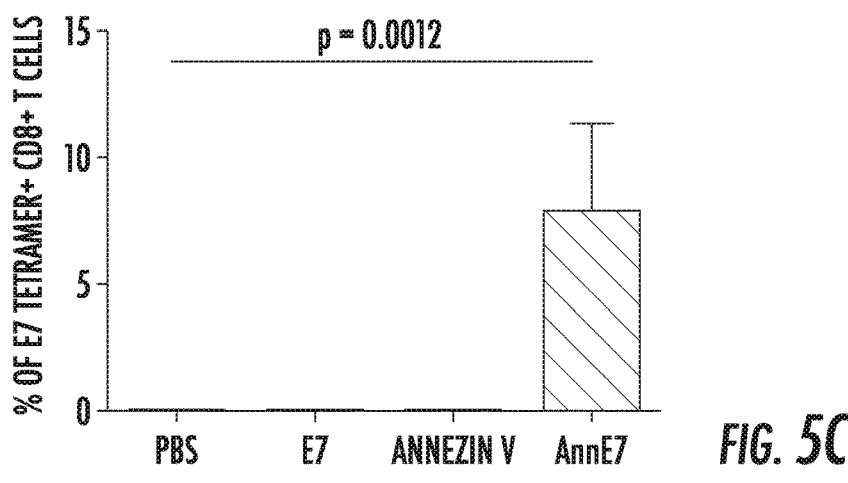
Figure 5D:
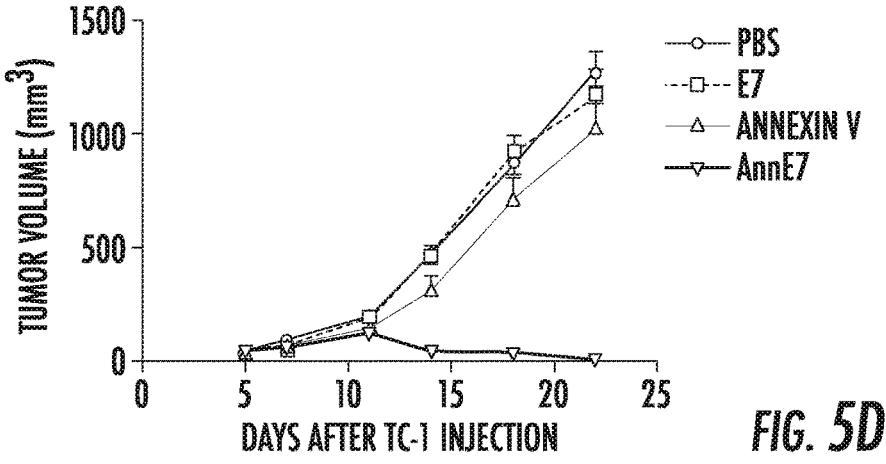
Figure 5E:
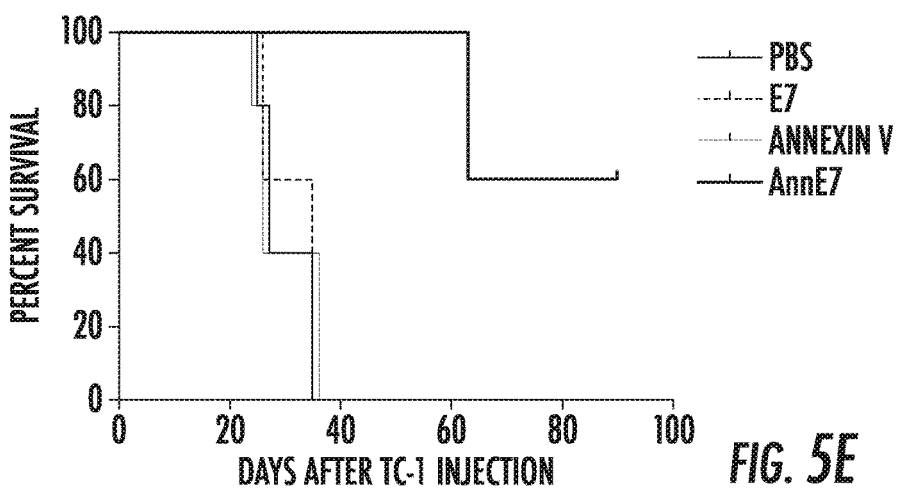
Figure 6A:
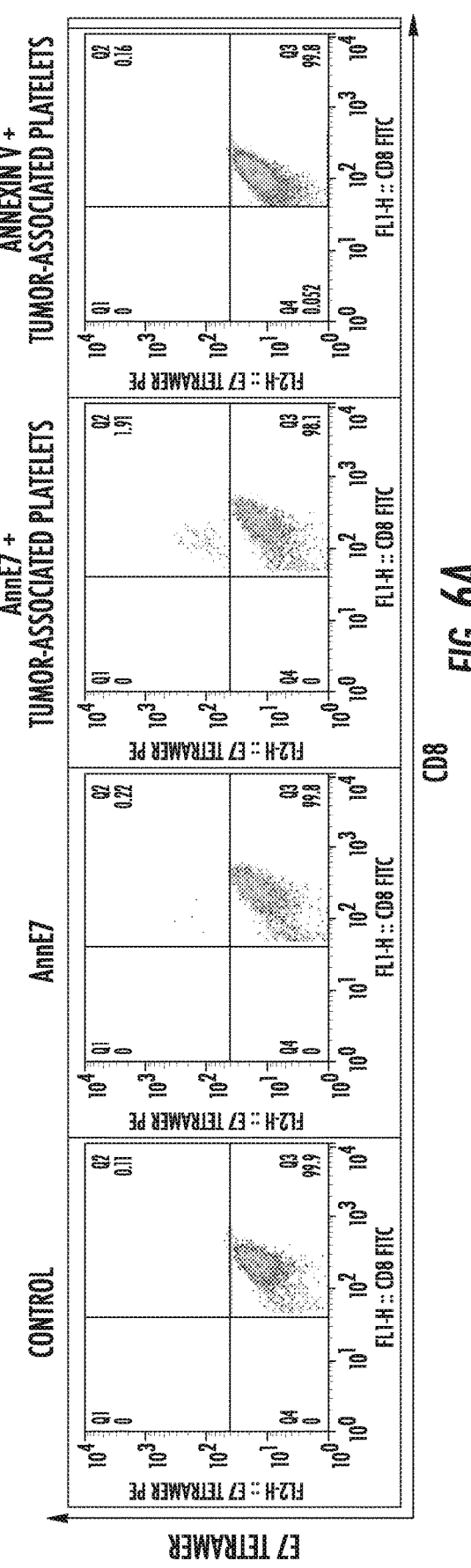
Figure 6B:
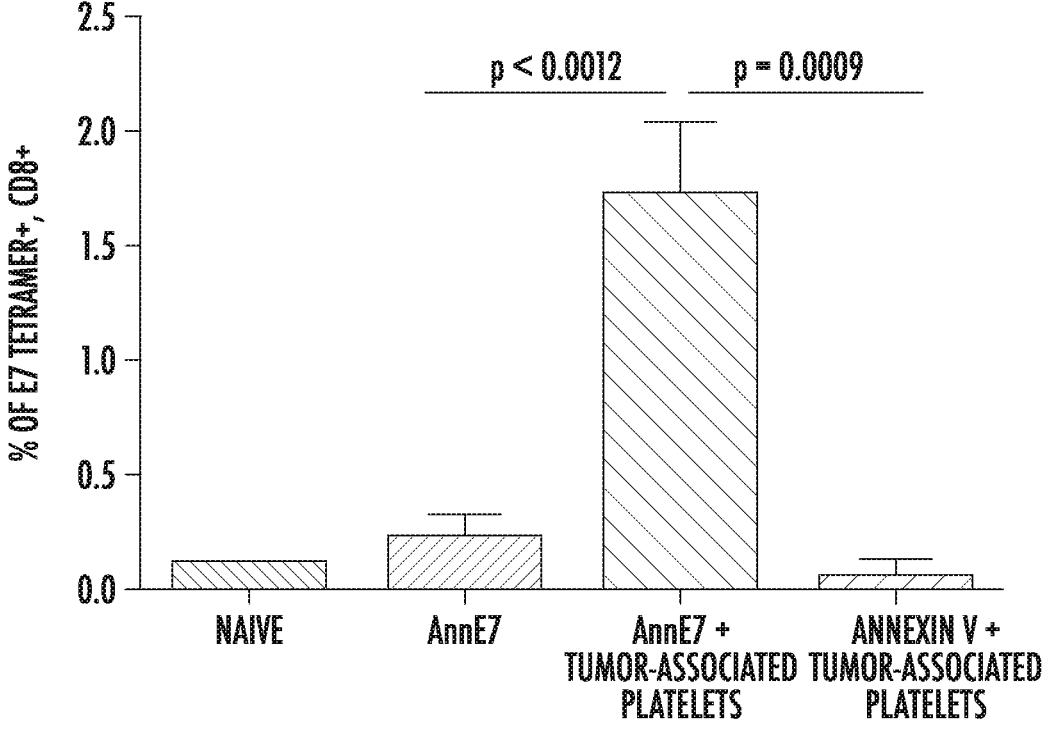
Figure 6C:
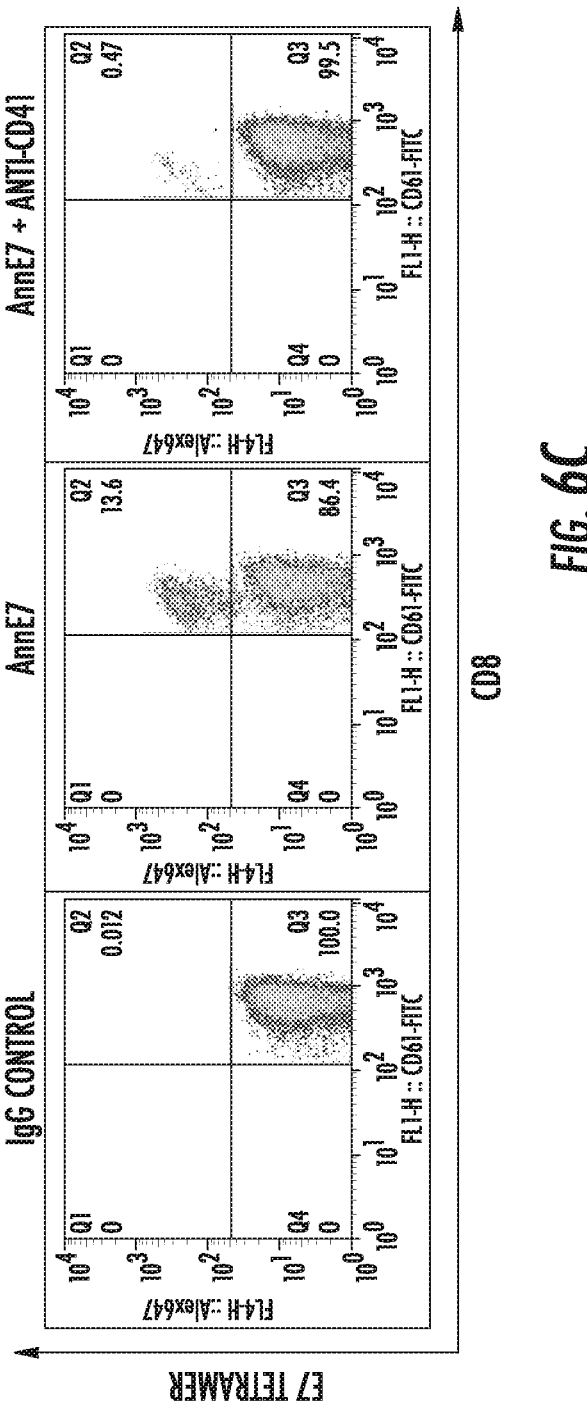
Figure 6D:
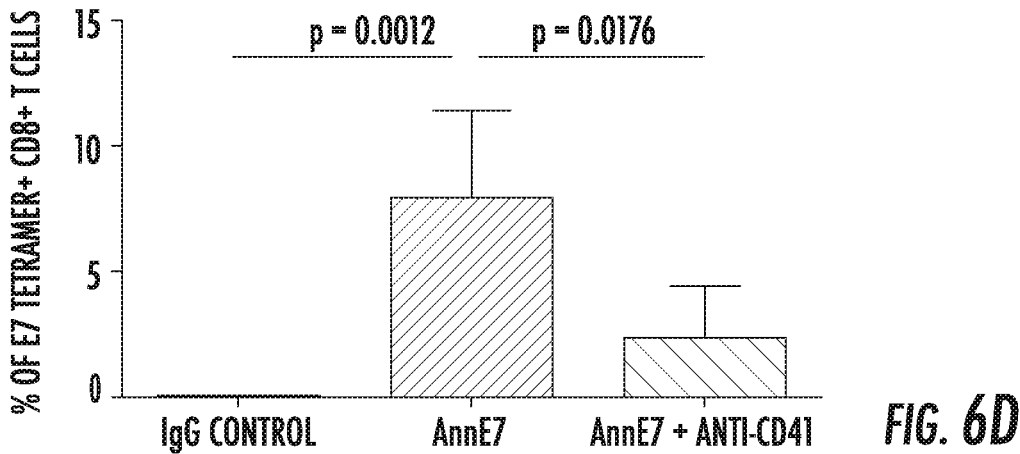
Figure 6E:
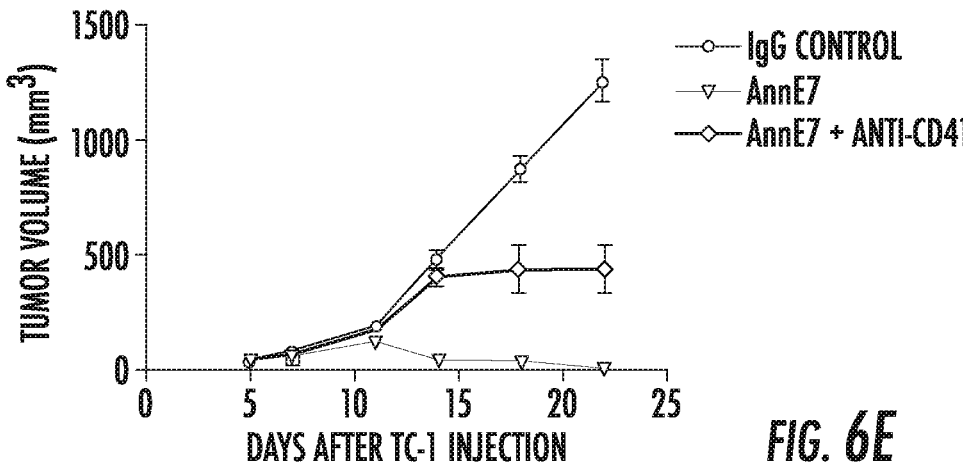
Figure 6F:
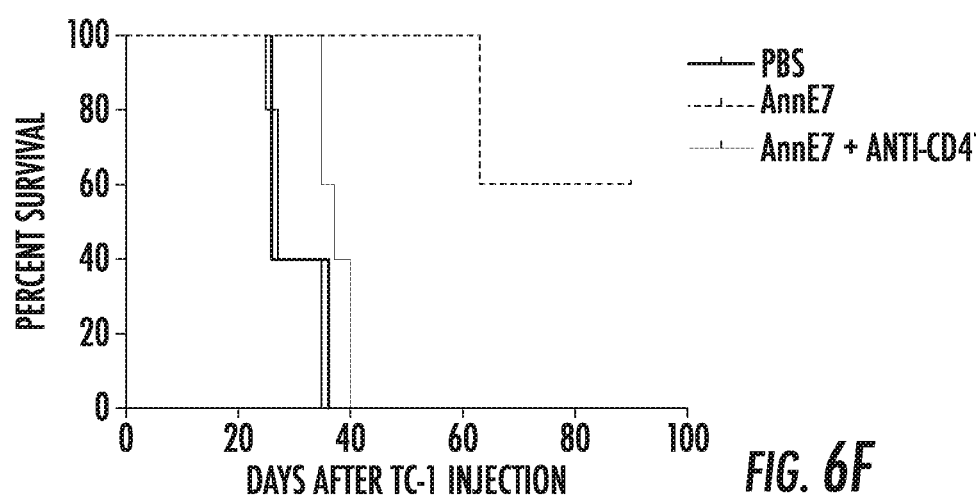

From our previous experiment, we have shown AnnE7 to successfully target tumors. Next, to determine whether AnnE7 could generate anti-tumor immunity (FIG. 5). As shown in FIG. 5A, we treated tumor-bearing mice with either E7, annexin V, or AnnE7 on days 5, 8, and 11 after TC-1 tumor inoculation, before collecting peripheral blood mononuclear cells (PBMCs) for E7 tetramer staining on day 14. From our results, only AnnE7-treated mice had a noticeable increase in CD8+ T cell populations compared to control mice (FIGS. 5B-C). In monitoring tumor volumes of TC-1, AnnE7-treated tumor-bearing mice seemingly suppressed tumor growth (FIG. 5D). Together, FIGS. 5B-D suggest that AnnE7 generates anti-tumor immunity. Additionally, AnnE7 was shown to increase the survival rate of tumor-bearing mice, compared to control, E7-treated, and annexin V-treated mice (FIG. 5E).

Next, we examined whether AnnE7's ability to generate anti-tumor immunity was platelet-dependent (FIG. 6). We administered either AnnE7 or annexin V alone with or without tumor-activated platelets to naive mice before collecting their PBMCs for E7 tetramer staining. We found that only mice injected with AnnE7 and tumor-activated platelets were able to generate an E7-specific CD8+ T cell population when compared to naive mice (FIGS. 6A-B). In addition, administering AnnE7 alone could not elicit an E7-specific CD8+ T cell response in naive mice, suggesting that AnnE7 anti-tumor immunity is tumor-activated and platelet-dependent. To verify this observation, we performed a platelet depletion experiment by administering anti-CD41 platelet antibodies to tumor-bearing mice compared to a control group administered with IgG isotype antibodies. Upon platelet depletion (FIG. 8), we observed a significant decrease in anti-tumor immunity in AnnE7-treated tumor-bearing mice compared to tumor-bearing mice without platelet depletion (FIG. 6C-D). We also observed an increase in tumor volume and decrease in survival rate of platelet-depleted tumor-bearing mice treated with AnnE7 compared to non-platelet-depleted tumor-bearing mice treated with IgG antibodies, suggesting AnnE7 anti-tumor immunity to not be as affective when platelets are depleted (FIG. 6E-F). From our platelet depletion experiment, we show that AnnE7 anti-tumor immunity is tumor-activated and platelet-dependent.

Example 5

AnnE7 anti-tumor immunity requires platelet-derived CD40L.

Figure 7A:
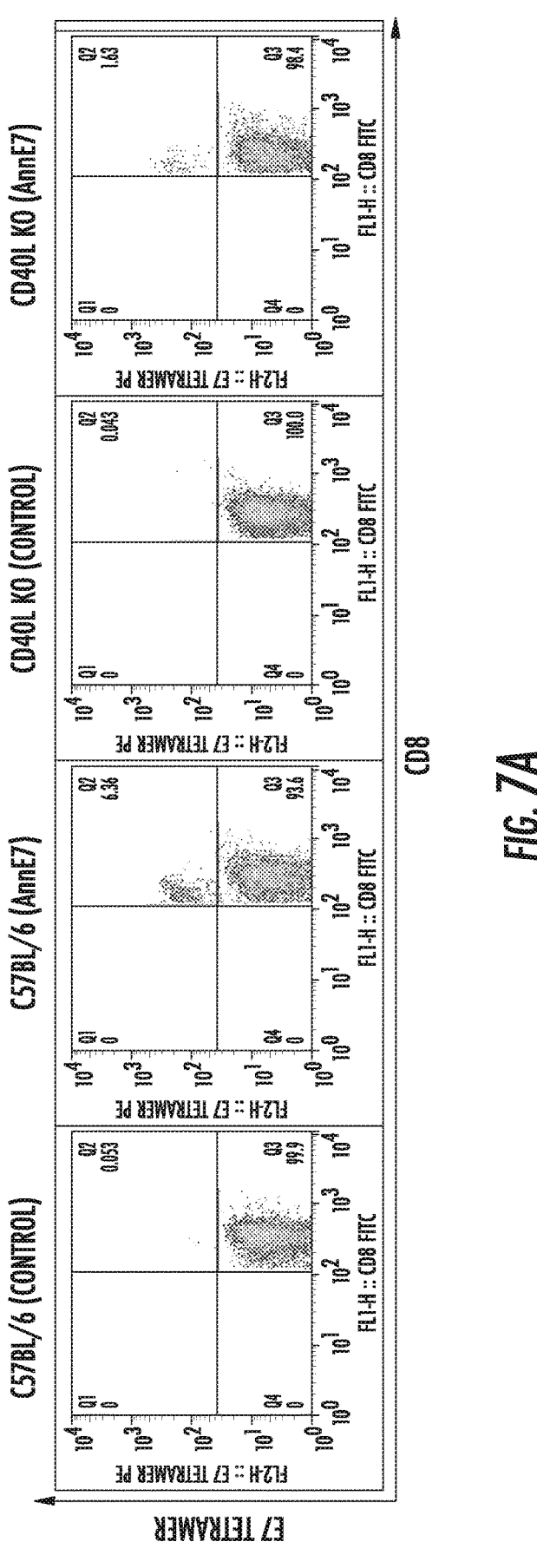
Figure 7B:
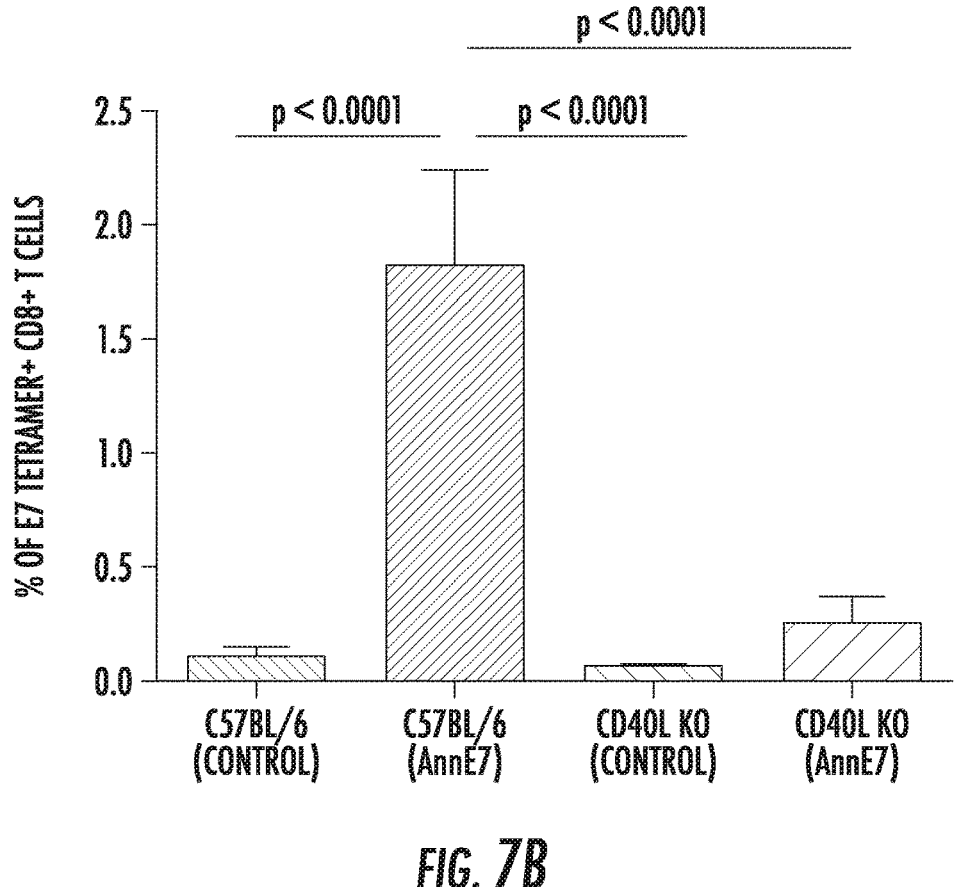
Figure 7C:
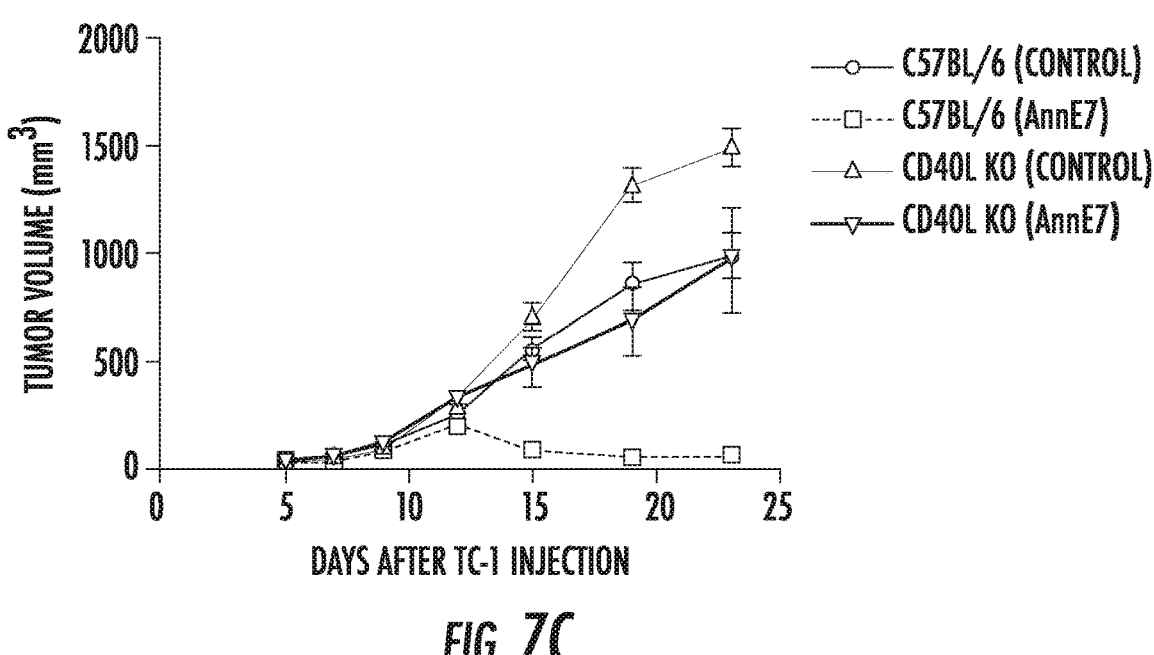
Figure 7D:
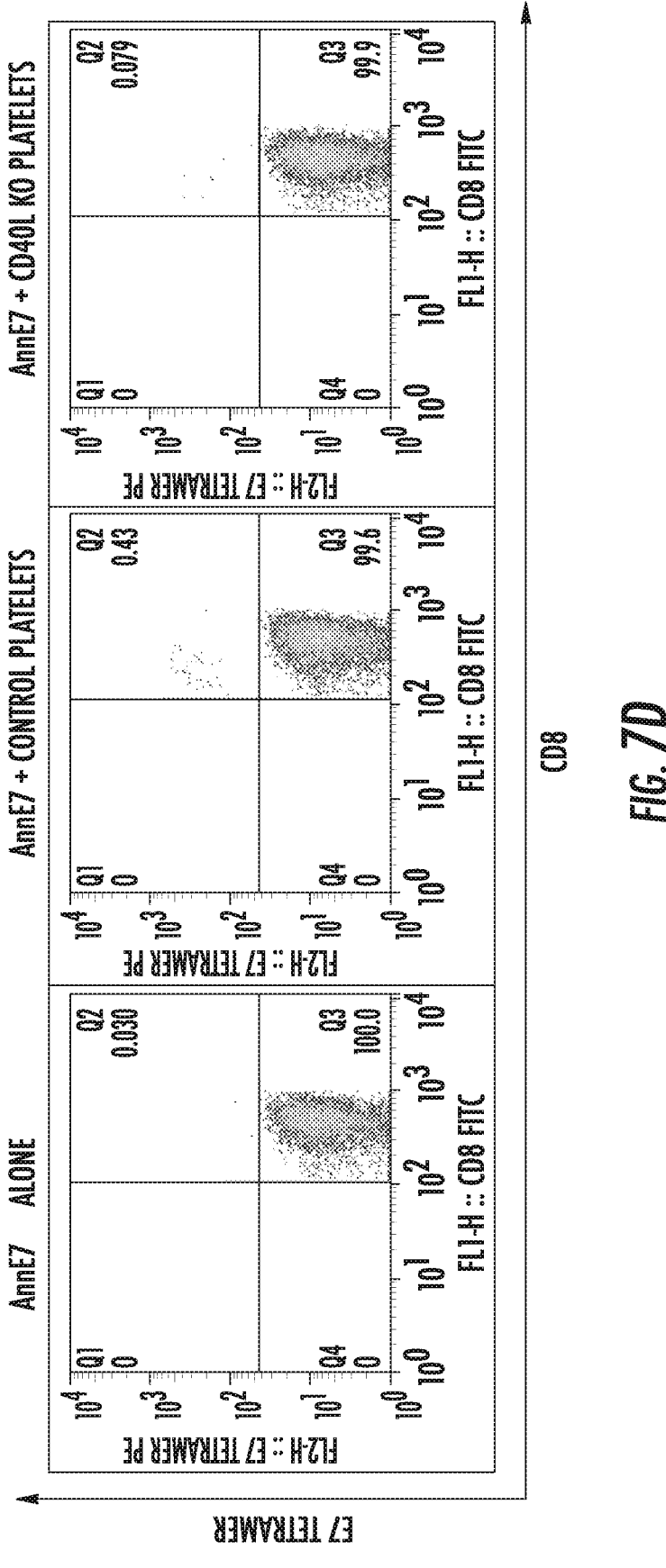
Figure 7E:
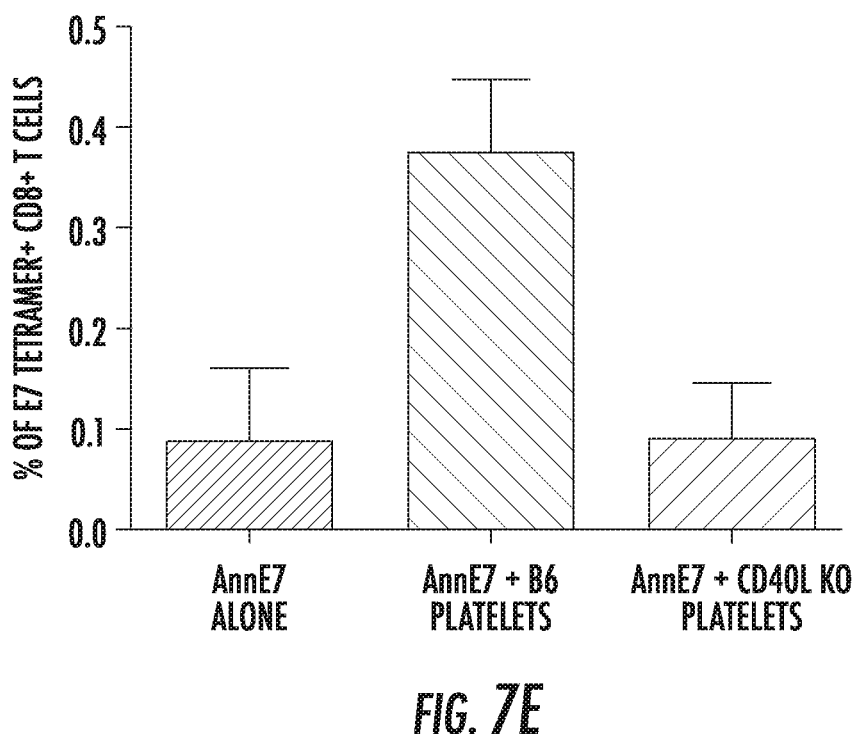
Figure 7F:
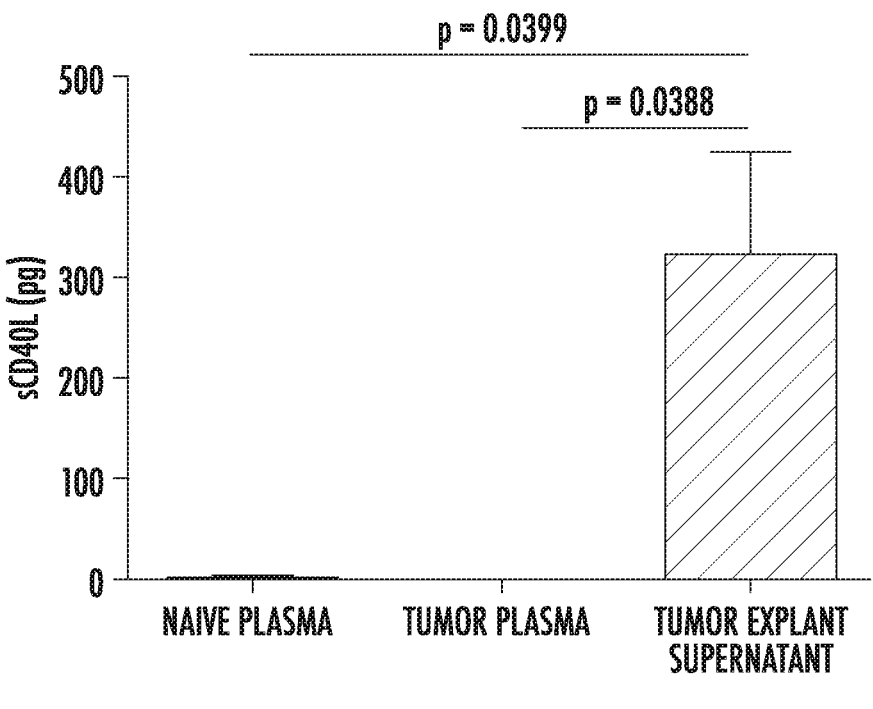

Identified as a co-stimulatory molecule expressed on T cells, CD40L has also been shown to play an important role in platelets; specifically, platelet CD40L modulates inflammatory pathways by activating leukocytes and DCs ((27, 28); for review, see (29)). As a result, we wanted to see whether CD40L plays an important role in generating anti-tumor immunity in tumor-bearing mice administered with AnnE7 (FIG. 7). When comparing the effects of AnnE7 in naive mice and CD40L knockout (KO) TC-1 tumor-bearing mice, we found that AnnE7 generated a noticeable weaker E7-specific CD8+ T cell response in CD40L KO mice compared to naive mice (FIGS. 7A-B). Additionally, AnnE7 was unable to suppress tumor growth in CD40L KO mice compared to the strong anti-tumor response observed in naive C57BL/6 mice (FIG. 7C). When we mixed AnnE7 with tumor-activated platelets isolated from naive C57BL/6 and CD40L KO mice ex vivo and reintroduced them to naive C57BL/6 mice, we found that a strong E7-specific CD8+ T cell response requires the presence of both platelet-derived CD40L and AnnE7 (FIGS. 7D-E). We also prepared tumor explant supernatants from the primary TC-1 tumors to verify that there are indeed more CD40L in the tumor microenvironment compared to the plasma of both tumor-bearing and naive mice (FIG. 7F). When examining the tumor-infiltrating lymphocyte (TIL) populations in the naive and CD40L KO mice, we noticed higher CD45+ TIL expressions in AnnE7-treated naive mice compared to naive mice without AnnE7 treatment (FIG. 7G). CD45+ TIL expression was also much weaker in CD40L KO treated with AnnE7 (FIG. 7G). Similarly, CD8+CD45+ TIL expression was highest in AnnE7-treated naive mice, with a noticeable decrease in expression of AnnE7-treated CD40L KO mice (FIG. 7H). Therefore, it would appear that CD40L is essential for generating AnnE7 anti-tumor immunity.

Example 6

Concomitant administration of Annexin V protein and antigenic peptide following cisplatin treatment generates potent therapeutic antitumor effects and antigen-specific CD8+ T cell responses.

Figure 9A:
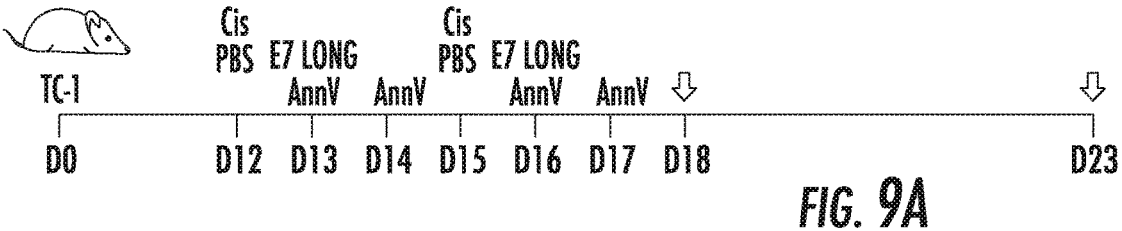
Figure 9B:
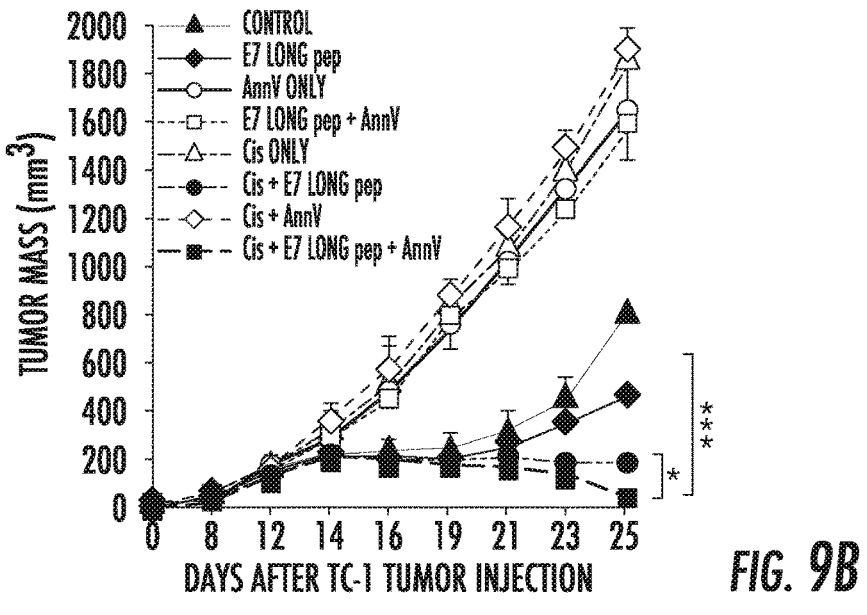
Figure 9C:
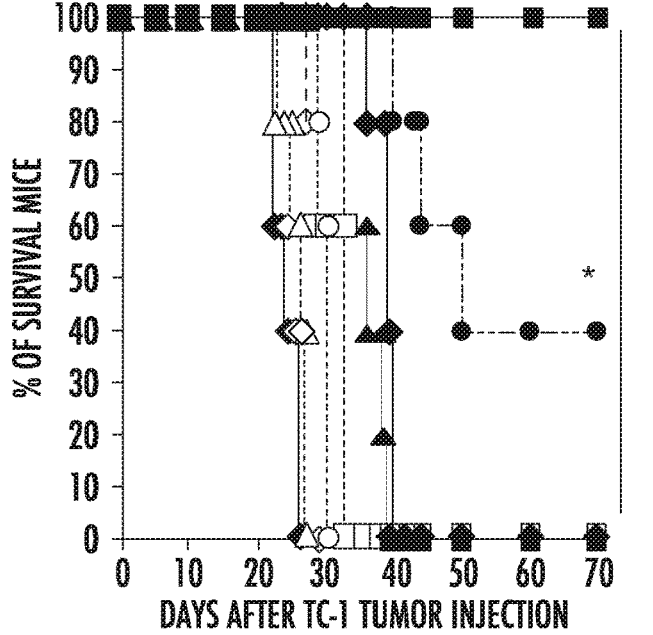
Figure 9D:
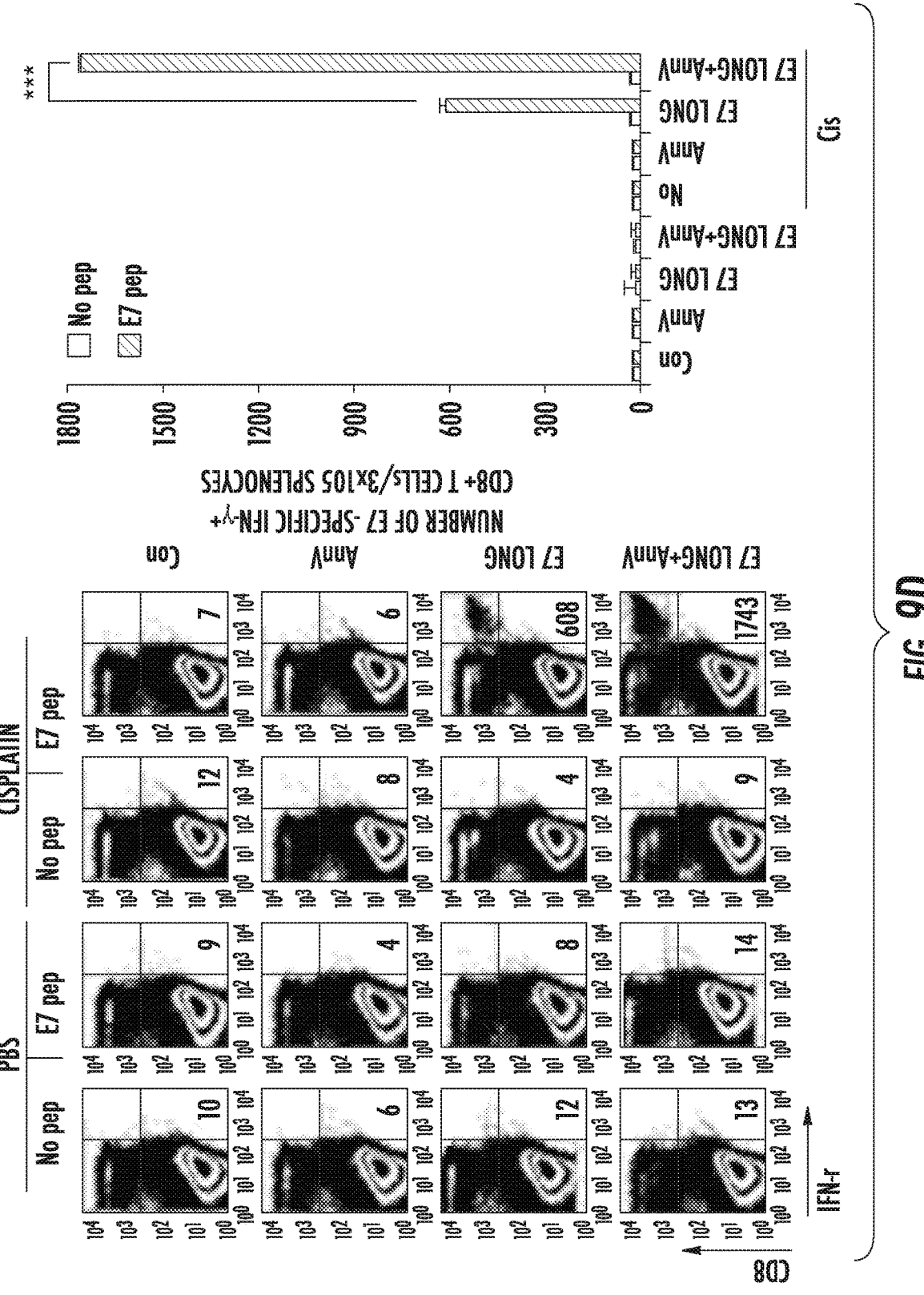
Figure 9E:
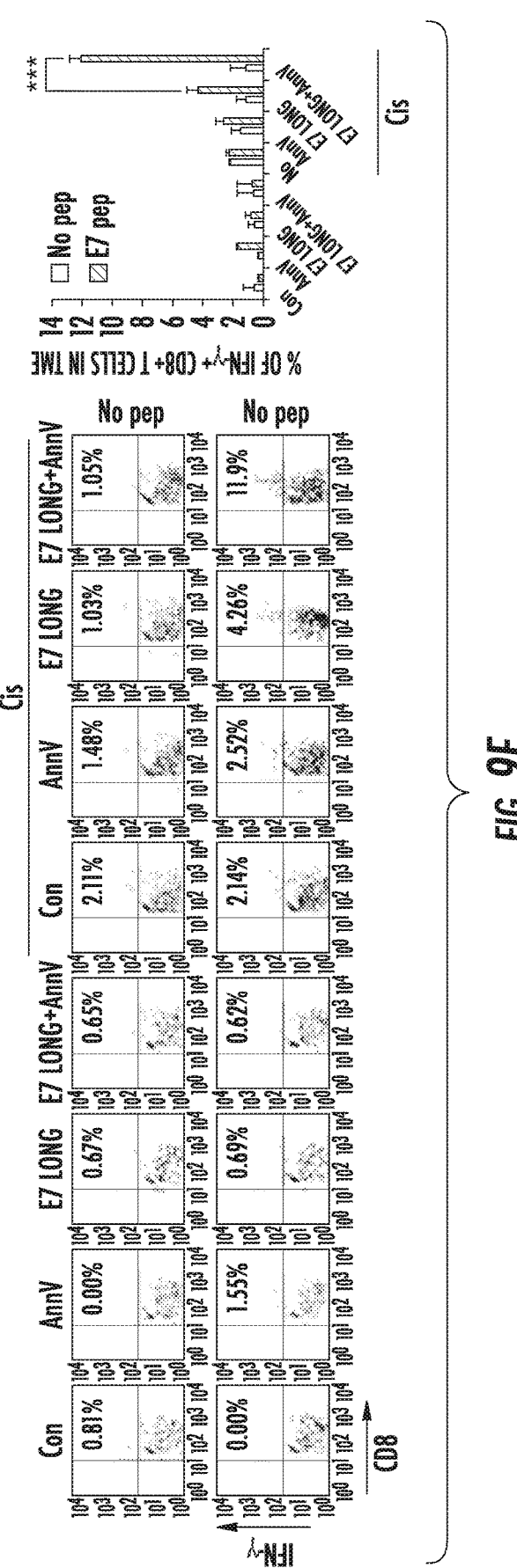

To evaluate the influence of AnnV administration on the therapeutic antitumor efficacy and immunogenicity of tumor-specific immunization following cisplatin treatment, we utilized the TC-1 tumor cells that express the E7 early protein of human papillomavirus type 16 (HPV16-E7). TC-1 tumor cells were inoculated subcutaneously into C57BL/6 mice to establish the preclinical tumors. The tumor bearing mice were then treated with intraperitoneal injection of cisplatin, intratumoral vaccination of HPV16-E7 long peptides, and/or intravenous administration of AnnV protein, with phosphate buffer saline (PBS) as negative controls (FIG. 9A). Tumor growth was monitored by palpation and inspection twice a week following tumor challenge. Administration of cisplatin, E7 long peptide, and AnnV combined resulted in the potent control TC-1 tumor growth compared to other treatments (FIG. 9B). Furthermore, all TC-1 tumor bearing mice treated with cisplatin, E7 long peptide, and AnnV survived at least 70 days after tumor challenge, while 60% of mice in cisplatin and E7 long peptide group died by 50 days after tumor challenge, and all mice in other treatment groups died by 40 days after tumor challenge (FIG. 9C). When assessing the resultant E7-specific immune response generated by the various treatment strategies, significantly stronger systemic and tumor-infiltrating E7-specific CD8+ T cell responses were detected in TC-1 tumor bearing mice treated with cisplatin, E7 long peptide, and AnnV, as compared to those in mice other treatment groups (FIGS. 9D-E). These data show that AnnV administration can enhance the antitumor immunogenicity of therapeutic cancer vaccines following cisplatin treatment.

Example 7

Annexin V treatment rescued the PS-mediated immune suppression in tumor microenvironment generated by cisplatin administration.

Figure 10A:
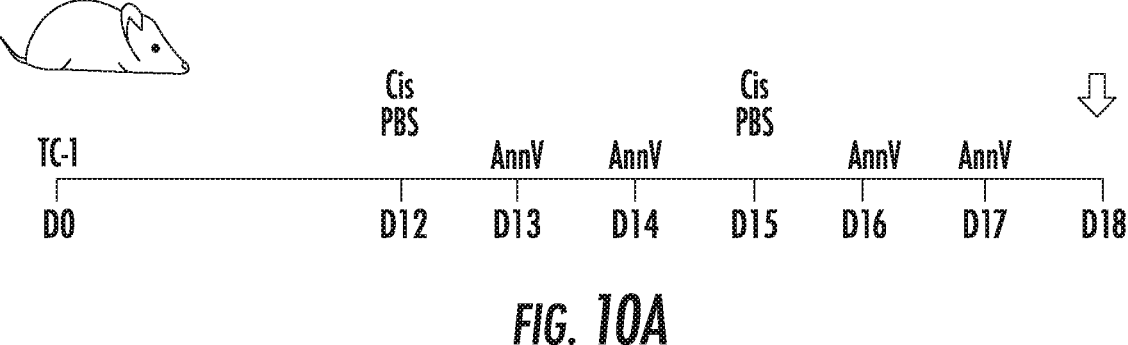
Figure 10B:
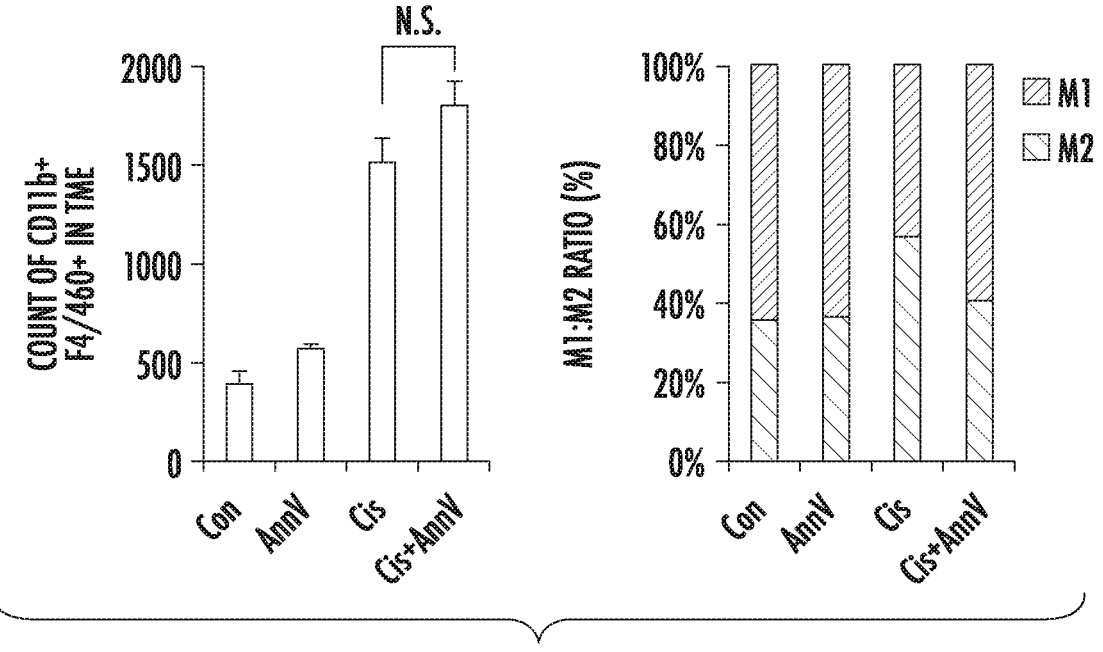
Figures 10C, 10D:
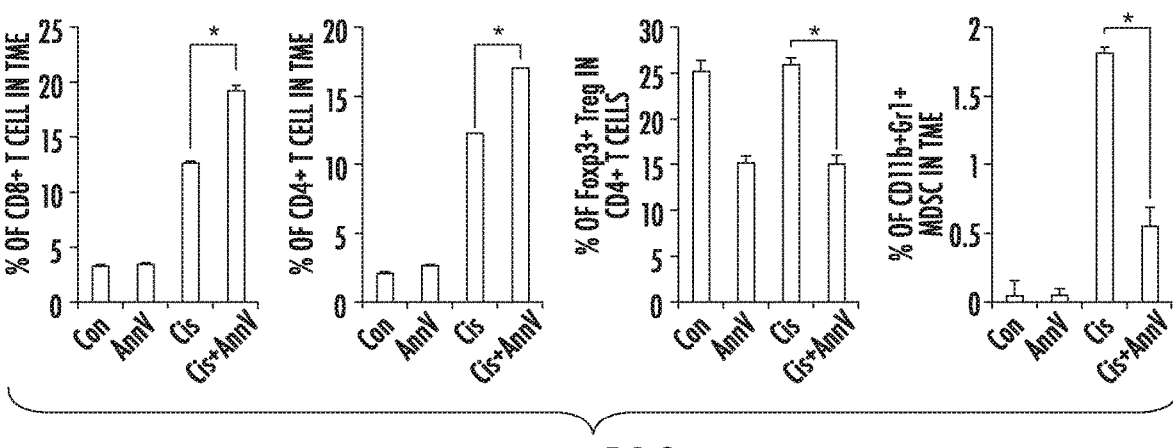

To decipher the mechanism of AnnV administration in enhancing the therapeutic antitumor effects and immunogenicity of antigen-specific immunization following cisplatin treatment, we sought to characterize the influence of AnnV administration on the TC-1 TME following cisplatin treatment. Following TC-1 tumor challenge, cisplatin treatment, and/or AnnV administration, we harvested the tumor tissues from tumor bearing mice and assessed the presence of various immune cell populations and cytokines within the TME (FIG. 10A). Compared to cisplatin treatment only, subsequent administration of AnnV did not increase the population of CD11b+F4/80+ macrophages in the TME. However, compared to no treatment control, cisplatin treatment skewed the M1:M2 ratio of macrophage population towards M2 phenotype, which was restored by subsequent AnnV treatment (FIG. 10B). AnnV administration following cisplatin treatment also led to greater infiltration of CD8+ T cells and CD4+ T cells into the TME, while reducing the populations of immune suppressive regulatory T cells (Tregs) and myeloid-derived suppressive cells (MDSCs), as well as the expression of PD-L1 within the TME (FIGS. 10C-D).

Figure 10E:
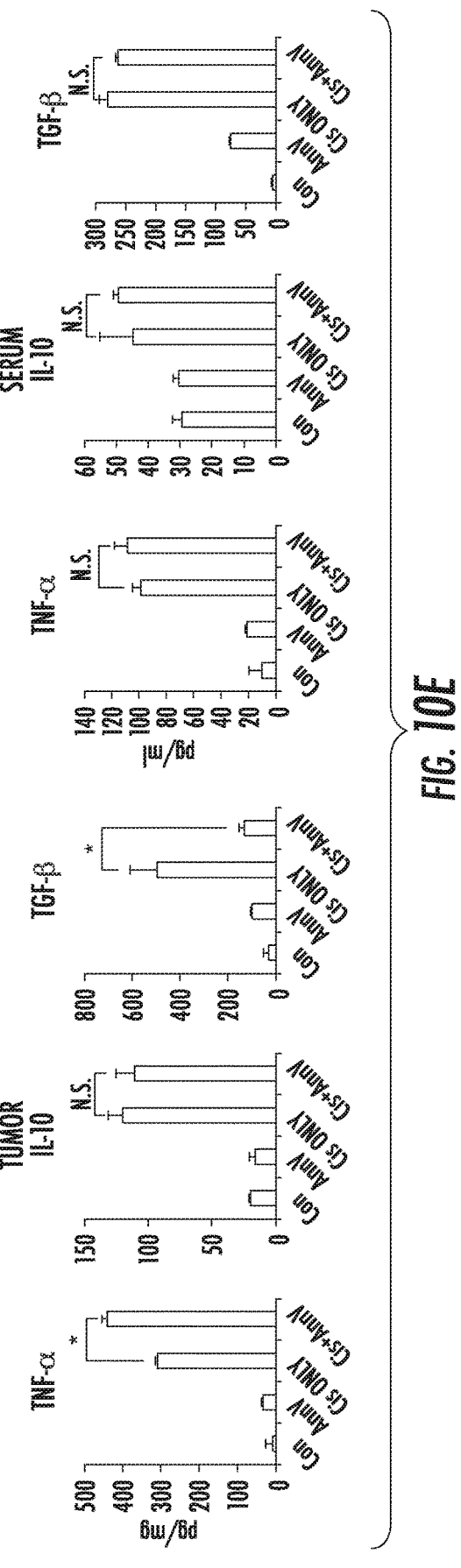

Since chemotherapy has been shown to enhance the expression of surface PS in the TME, particularly by stressed and apoptotic tumor cells, and that interaction between PS+ tumor cells with phagocytic innate immune cells help promote the immune suppressive state of TME, we hypothesize that AnnV, by binding to PS, can prevent the induction of immune suppression by PS+ tumor cells. As shown in FIG. 11, in vitro treatment with AnnV promotes the secretion of pro-inflammatory cytokine TNF-α and suppresses the production of anti-inflammatory, immune suppressive cytokine TGF-β by bone marrow-derived dendritic cells (BMDCs) and bone marrow-derived macrophages (BMDMs) co-cultured with cisplatin-treated apoptotic TC-1 tumor cells. Similarly, an increase in the TNF-α cytokine level and a decrease in TGF-β cytokine level were observed in the TME of TC-1 tumor-bearing mice treated with cisplatin and AnnV as compared to those treated with cisplatin only (FIG. 10E).

Figures 12A, 12B:
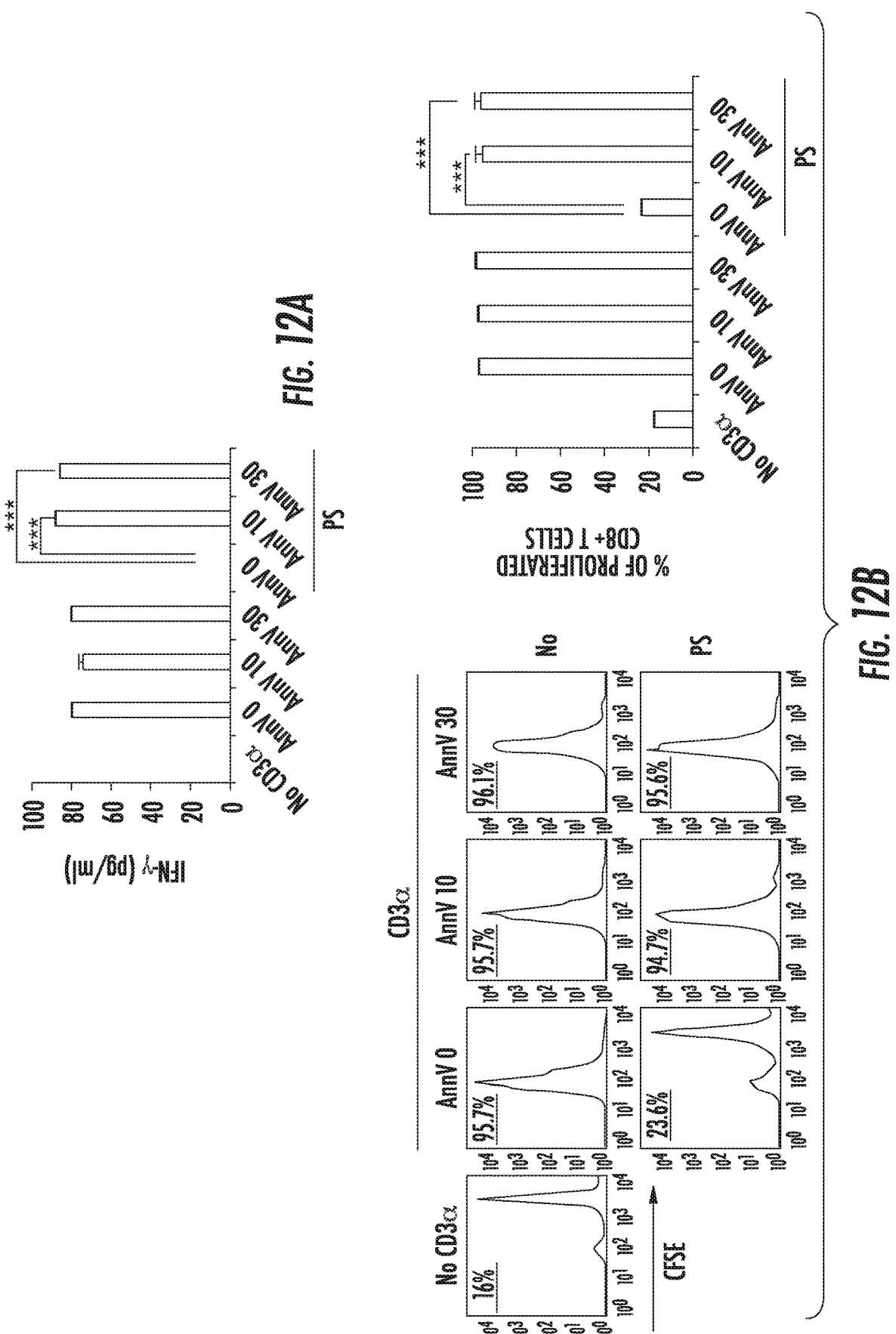

In addition to inducing the secretion of immune suppressive cytokines by phagocytes, PS+ apoptotic tumor cells can also exert inhibitory signals against tumor-specific CD8+ T cells via direct interaction. Indeed, in vitro incubation with soluble PS suppresses the activation and proliferation of CD8+ T cells stimulated with anti-CD3α antibody or PMA/I, which can be rescued by further treatment with AnnV (FIGS. 12A-D). Similarly, in vitro AnnV treatment enhances the activation and proliferation of OT-1 T cells incubated with OVA-expressing TC-1 cells that are pretreated with or without cisplatin (FIGS. 12E-F).

Together, these data support the notion that cisplatin treatment can induce an immunosuppressive TME by promoting the formation of PS-exposed apoptotic tumor bodies, and that AnnV administration help blocks the interaction of PS+ tumor cells with innate and immune cells, thereby rescue the immunosuppressive state of TME.

Example 8

Alteration of the therapeutic antitumor immunity generated by tumor antigenic peptide vaccination following cisplatin treatment by administration of anti-TGF-β or anti-TNF-α neutralizing antibodies.

Since we observed that AnnV administration following cisplatin treatment increased the level of TNF-α and decreased the level of TGF-β within the TME, we sought to characterize how the alteration of these cytokine levels affects the TME by treating TC-1 tumor bearing mice receiving cisplatin and/or E7 long peptide administration with anti-TNF-α or anti-TGF-β blocking antibody (FIG. 3A 13). Compared to those treated with cisplatin and E7 long peptide only, significantly better tumor control and prolonged survival were observed in TC-1 tumor bearing mice treated with cisplatin, E7 long peptide, and anti-TGF-0, while cisplatin, E7 long peptide, and anti-TNF-α treatments resulted in worse tumor control and mice survival (FIGS. 13B-C).

Figure 13A:
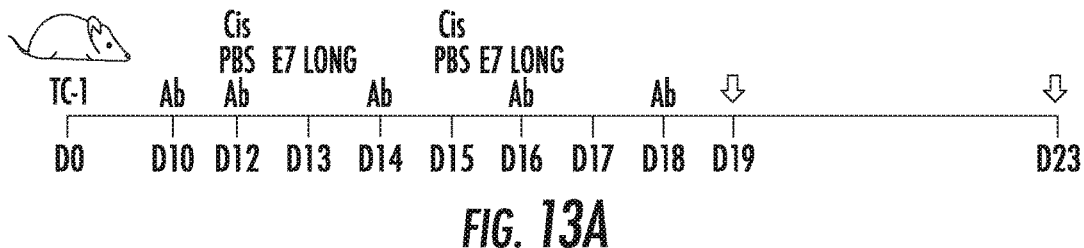
Figure 13B:
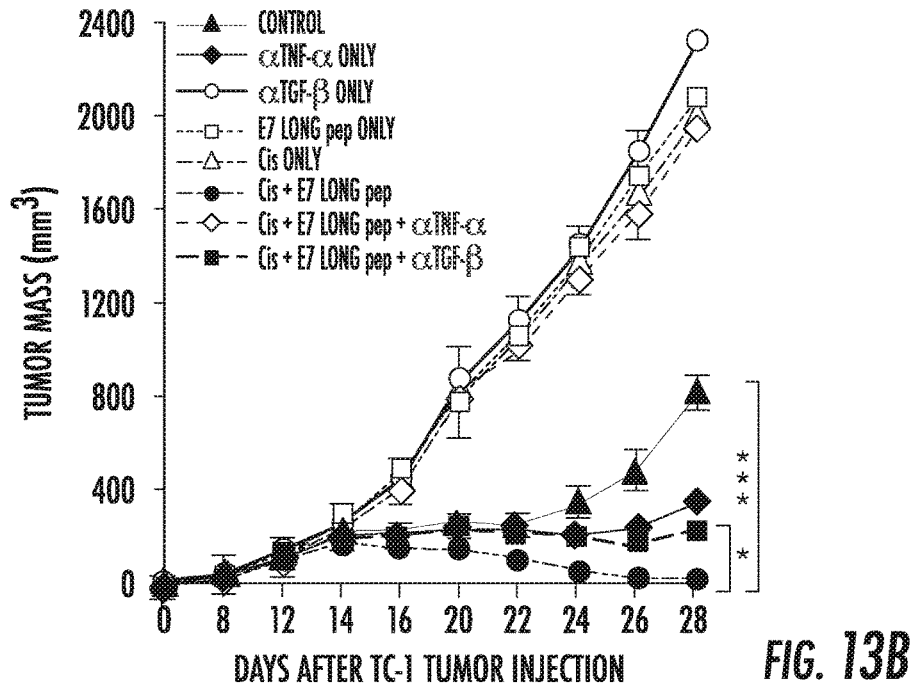
Figure 13C:
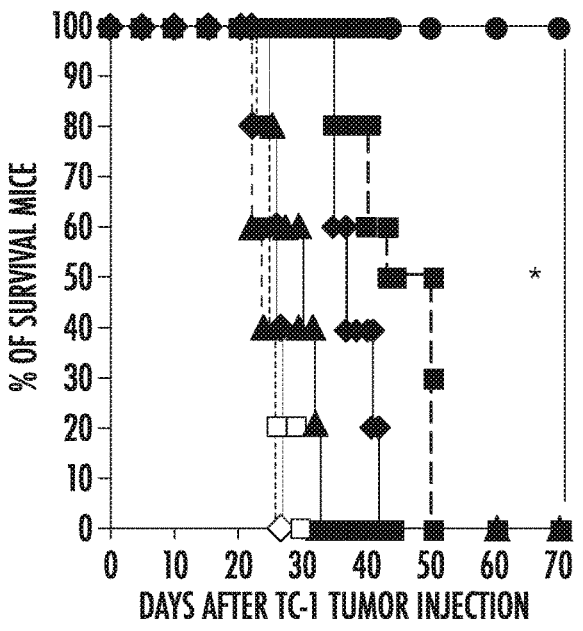
Figure 13D:
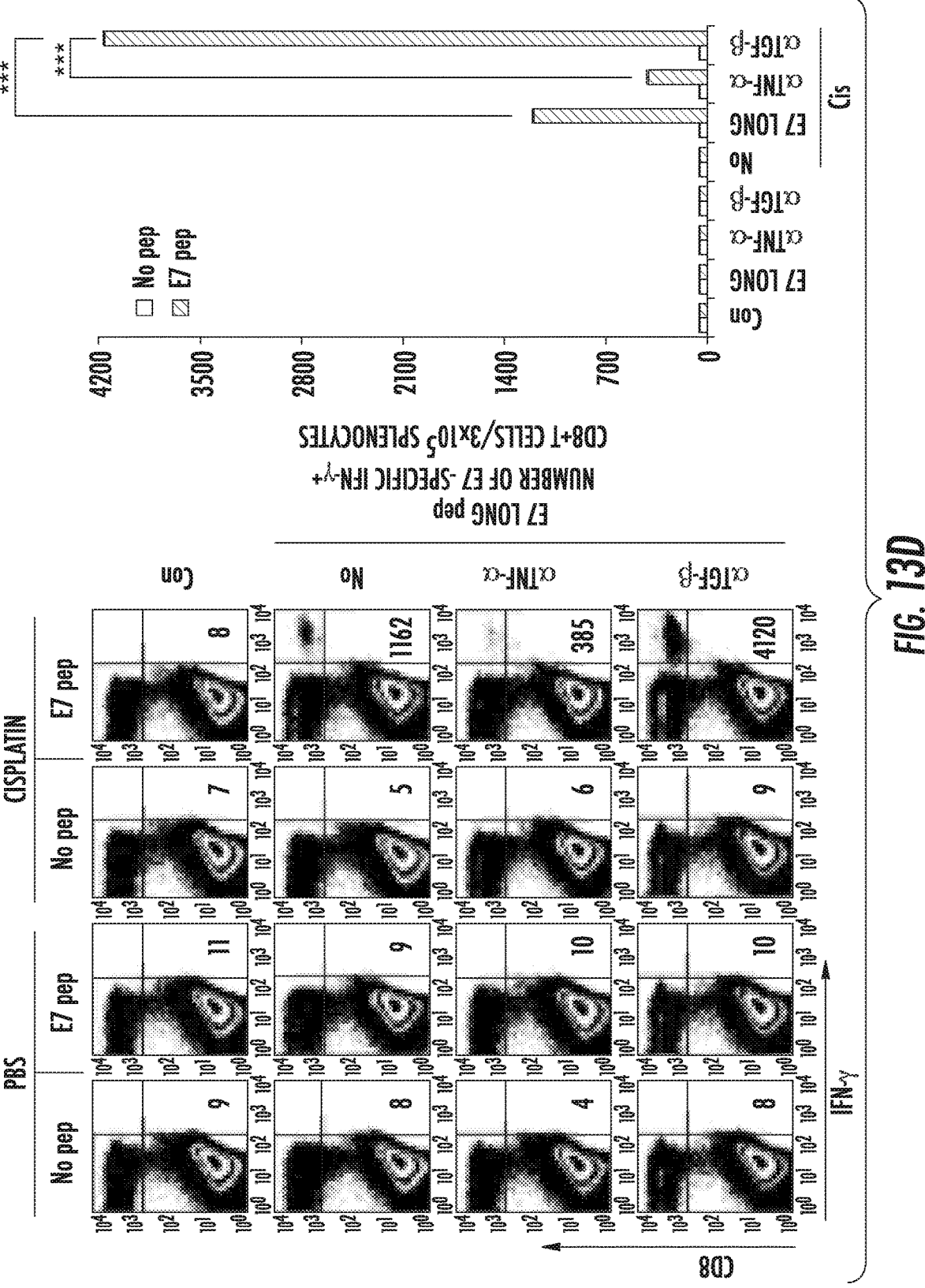
Figure 13E:
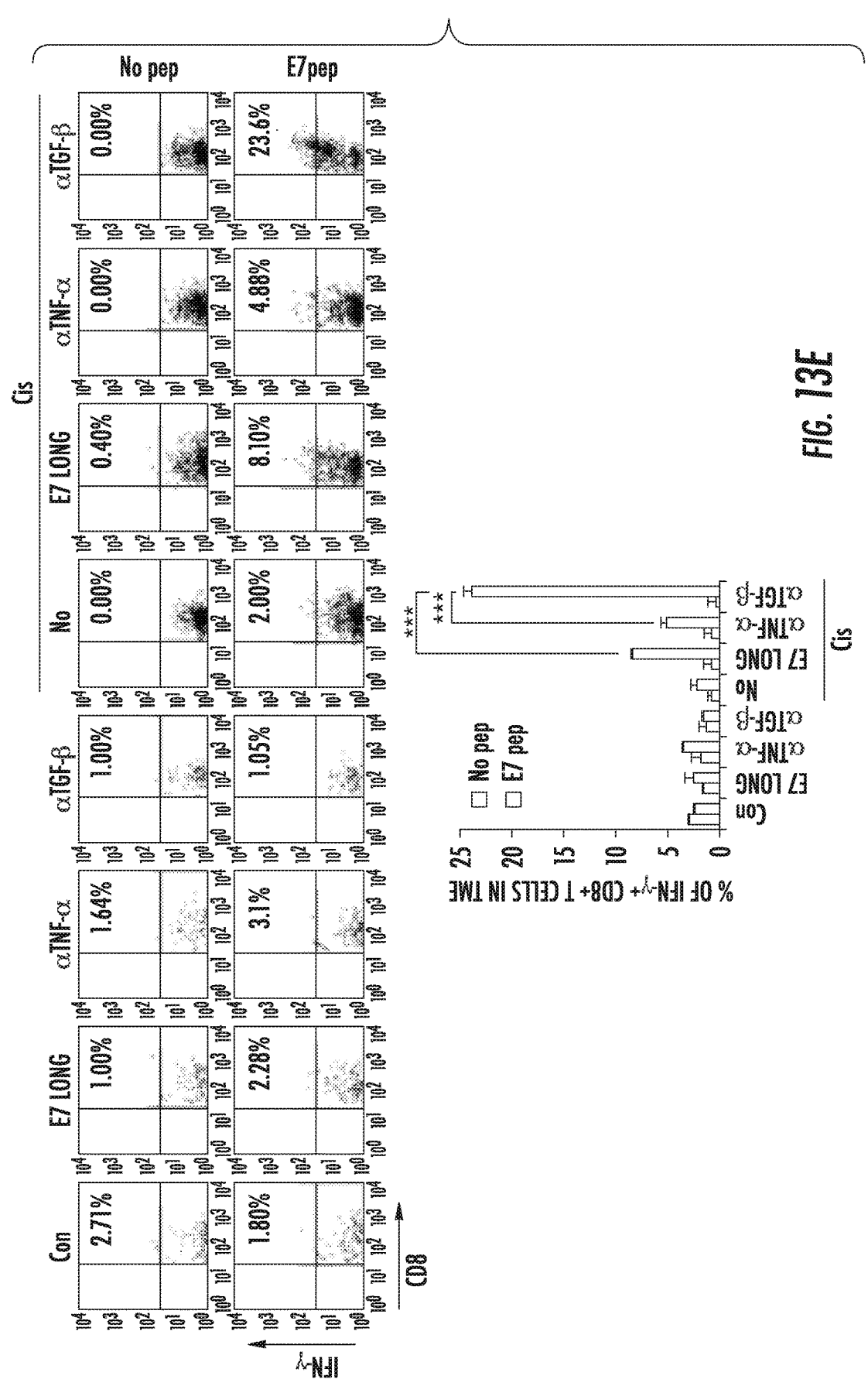

Administration of anti-TGF-β also enhanced both the systemic and tumor-infiltrating E7-specific CD8+ T cell response in mice treated with cisplatin and E7 long peptide, while administration of anti-TNF-α suppressed the generation of such immune responses (FIGS. 13D-E). When characterizing the tumor immune microenvironment following various treatments, increase in M1:M2 macrophage ratio and CD8+ T cell population and a decrease in MDSCs population were observed in mice treated with cisplatin, E7 long peptide, and anti-TGF-β as compared to those treated with cisplatin and E7 long peptide only, while the opposite trends were observed those treated with cisplatin, E7 long peptide, and anti-TNF-α (data not shown). Anti-TGF-β treatment following cisplatin and E7 long peptide administration also decreased the level of TGF-β both systemically and within the TME while increasing the level of TNF-α, while the opposite effects were observed for anti-TNF-α administration (data not shown). These data demonstrate that administration of anti-TGF-β, but not anti-TNF-α, can induce similar therapeutic effects as AnnV treatment following chemotherapy and tumor antigen-specific vaccination and alleviate the immune suppression within the TME.

Example 9

Therapeutic antitumor efficacy of annexin V administration is comparable to that of other immune checkpoint inhibitors.

Figure 14A:
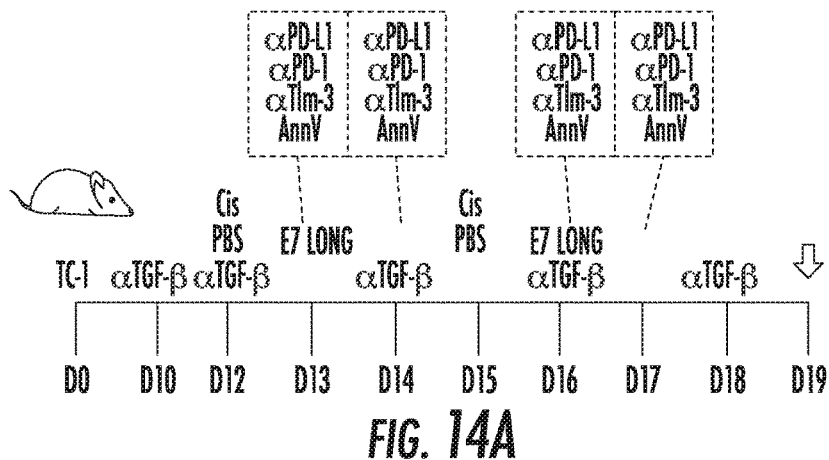
Figure 14B:
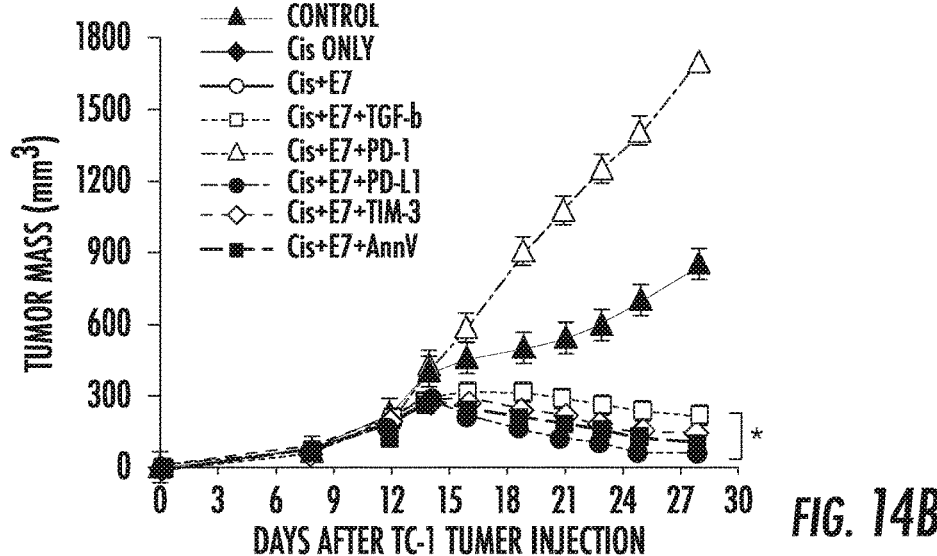
Figure 14C:
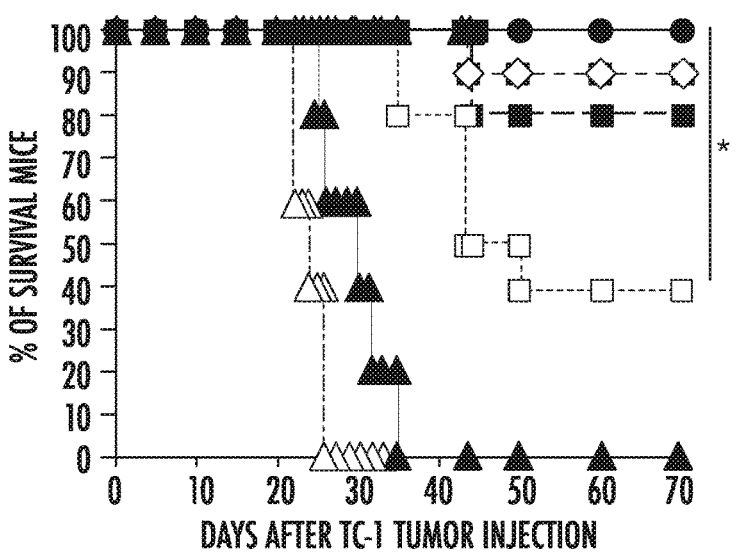
Figure 14D:
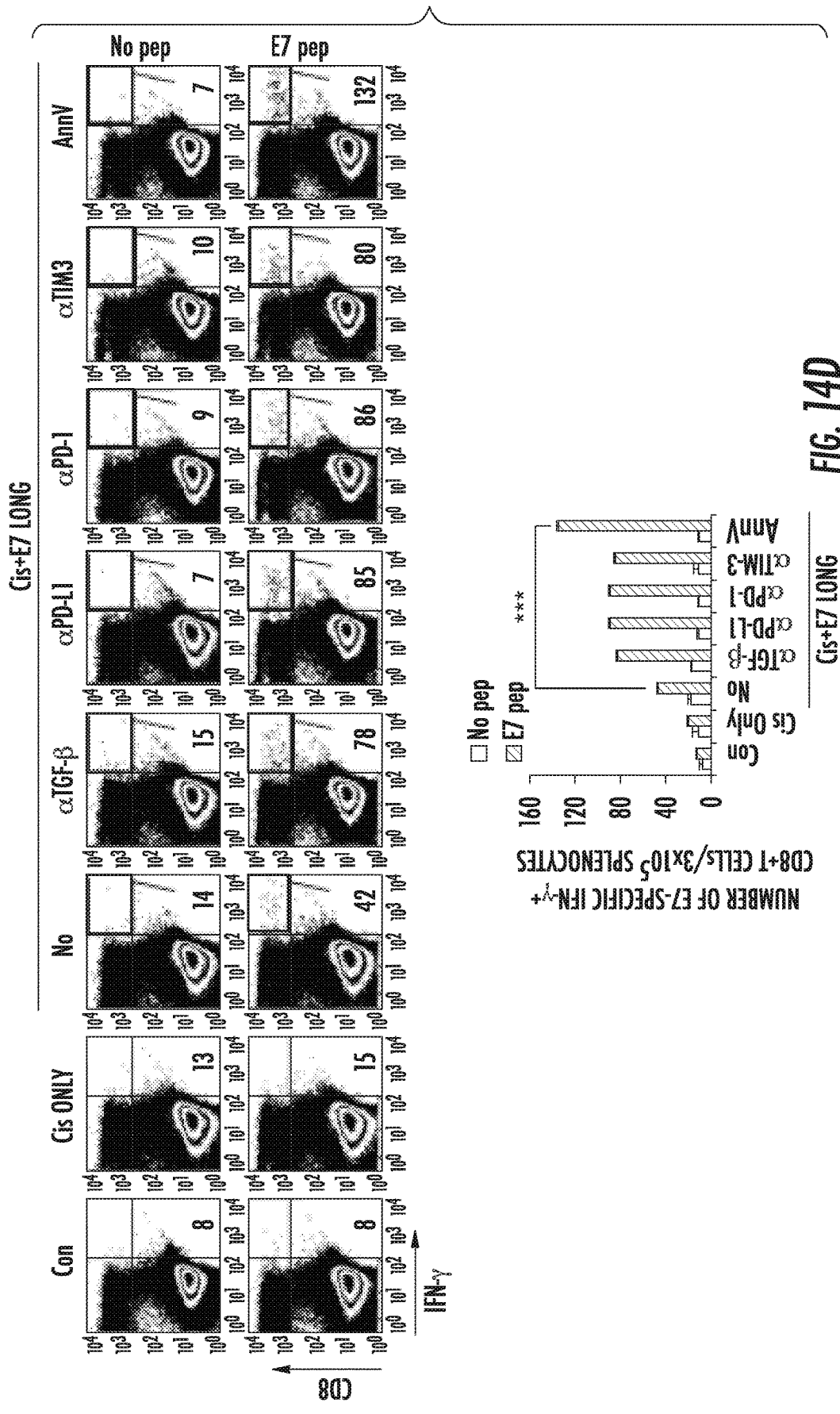
Figure 14E:
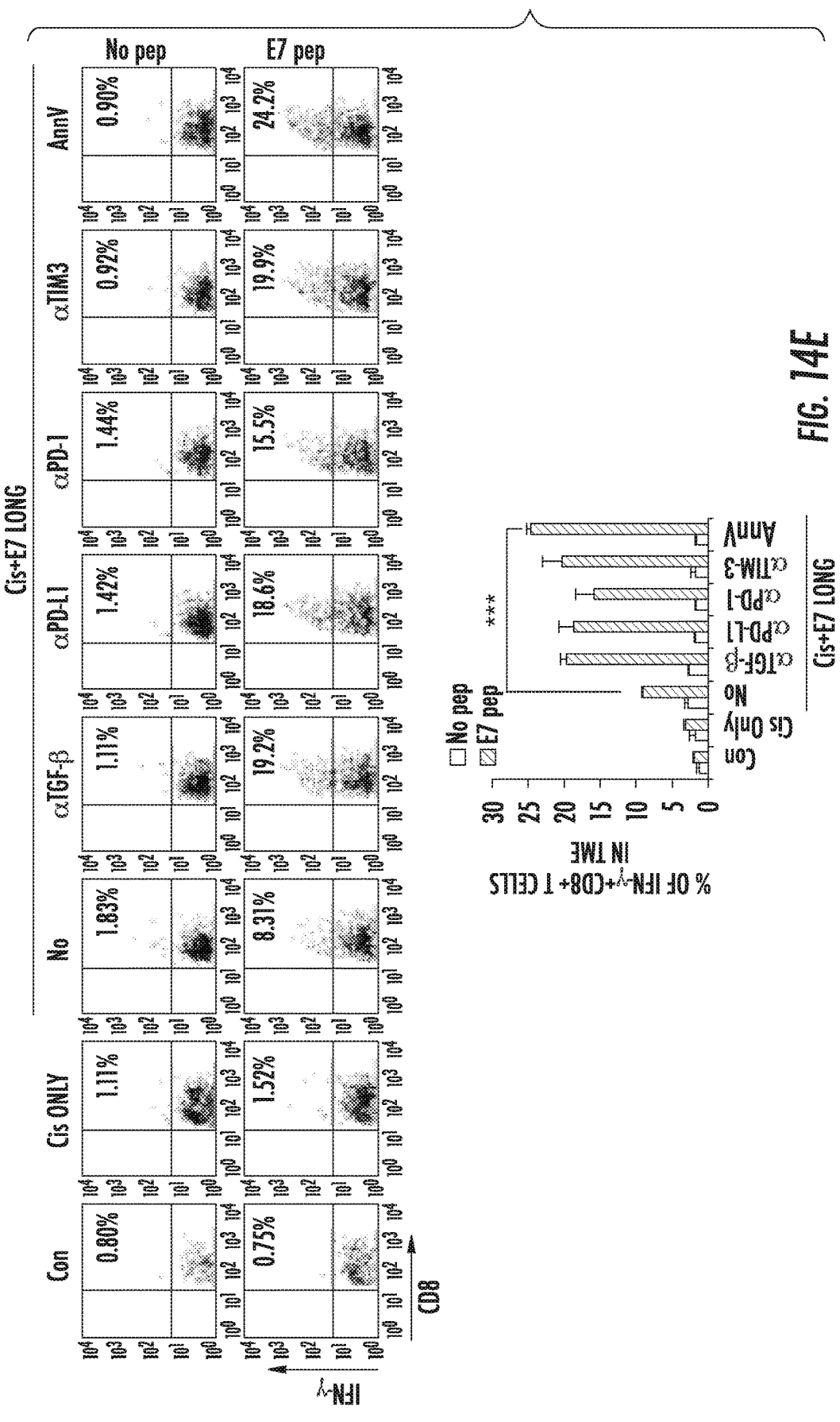

Combination treatment with antigen-specific immunotherapy and immune checkpoint inhibitors has been a promising emerging approach for enhancing the resultant immunogenicity and efficacy of immunotherapy. Due to the demonstrated potential of AnnV as an immune checkpoint inhibitor against PS-mediated immune suppression, we sought to assess the potency of AnnV administration as compared to the utilization of other reported immune checkpoint inhibitors by treating TC-1 tumor bearing C57BL/6 mice that have received cisplatin and/or E7 long peptide injection with further administration of AnnV, anti-TGF-0, anti-PD-1, anti-PD-L1, or anti-TIM-3 (FIG. 14A). Administration of various immune checkpoint inhibitor following cisplatin treatment and E7 long peptide vaccination resulted in comparable level of tumor control and prolonged mouse survival as compared to TC-1 tumor bearing mice treated with cisplatin and E7 long peptide only (FIGS. 14B-C). Tumor-bearing mice treated with cisplatin, E7 long peptide, and various immune checkpoint inhibitors also generated stronger systemic and tumor-infiltrating E7-specific CD8+ T cell responses compared to those treated with cisplatin and E7 long peptide only (FIGS. 14D-E). Together, these data demonstrate that AnnV treatment has comparable potency in enhancing the efficacy and immunogenicity of anti-tumor therapy as that of other immune checkpoint inhibitors.

Example 10

Administration of recombinant Annexin V-antigenic peptide fusion protein following chemotherapy generates potent therapeutic antitumor effects and antigen-specific CD8+ T cell responses.

Increasing evidence has highlighted the importance of infiltrating, local CD8+ T cell response in the treatment of cancer. Particularly, the presence of abundant and immunogenic tumor antigens within the TME is a crucial factor for the generation of effective, localized antitumor immune responses. We have thus far administered the E7 long peptide into TC-1 tumor bearing mice via the intratumoral route since we have previously demonstrated that intratumoral administration of a therapeutic cancer vaccine resulted in the generation of more potent antigen-specific antitumor immune responses compared to systemic vaccination. However, many intratumoral vaccinations are invasive in nature and less ideal for clinical application, thus warrants the need to explore alternative methods that can generate strong, local antitumor immune responses via systemic administration. Due to the high affinity binding between AnnV and PS exposed on the surface of apoptotic and tumor cells, AnnV has been shown to possess tumor homing capabilities, and has been utilized as guiding and labeling tools for imaging tumor cell apoptosis. We further confirmed the rapid and concentrated accumulation of Gaussia luciferase—AnnV fusion protein (AnnV-Gluc) within the TME in vivo when administered following chemotherapy (FIG. 15). We thus reasoned that AnnV can serve not only as an immune checkpoint inhibitor for tumor treatment, but also as a potent guiding molecule to home vaccine incorporated tumor antigens into the tumors.

To test our hypothesis, we fused the DNA sequence of murine H2-Db restricted epitope of HPV16-E7 (RAHYNIVTF) (SEQ ID NO: 12) to that of AnnV to generate AnnV-E7 fusion protein (data not shown) and assessed the therapeutic efficacy of systemic AnnV-E7 administration as compared to systemic administration of AnnV only or E7 peptide only in TC-1 tumor bearing mice treated with or without cisplatin (FIG. 16A). Tumor bearing mice treated with cisplatin and AnnV-E7 demonstrated significantly better tumor control and prolonged survival compare to those in other treatment groups (FIGS. 16B-C). Furthermore, mice treated with cisplatin and AnnV-E7 generated both strongest systemic and tumor infiltrating E7-specific CD8+ T cell responses (FIGS. 16D-E). The therapeutic antitumor effects generated by AnnV-E7 vaccination following cisplatin treatment is CD8+ T cell dependent, as the administration of anti-CD8 neutralizing antibody abolished the ability of cisplatin and AnnV-E7 treatment mice to control TC-1 tumor growth (FIG. 17).

Figure 18A:
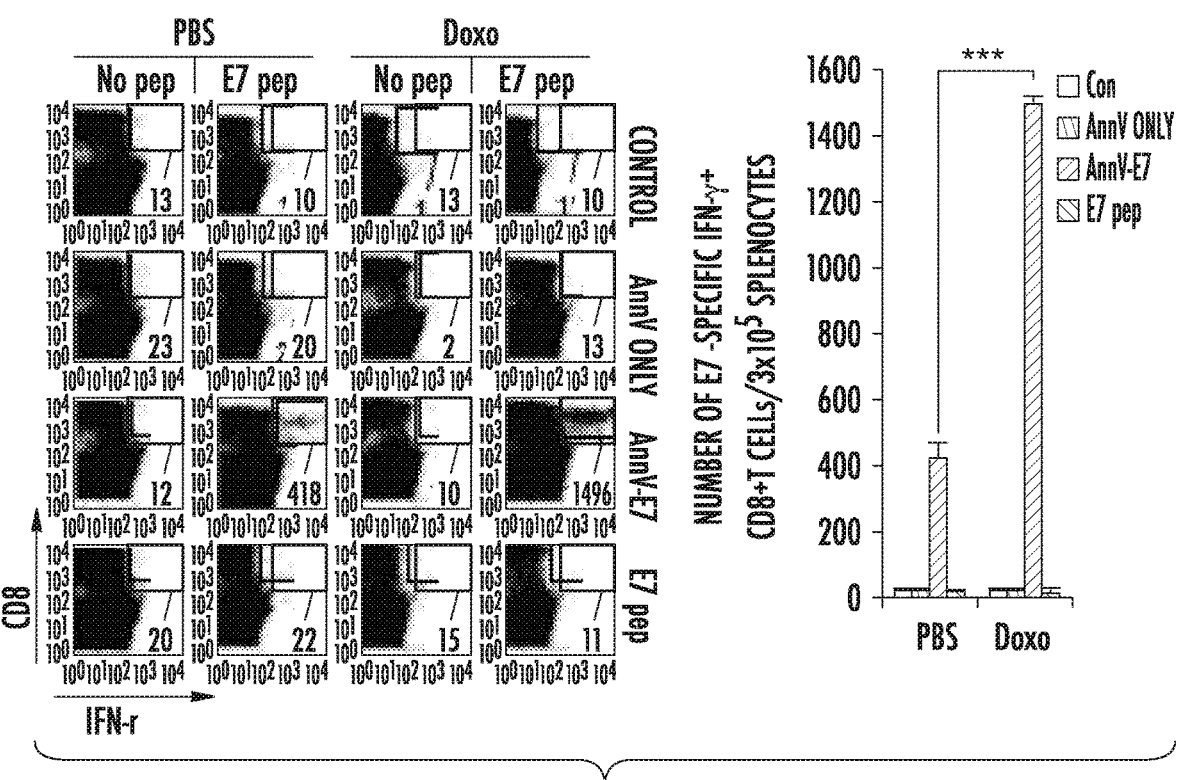
Figure 18B:
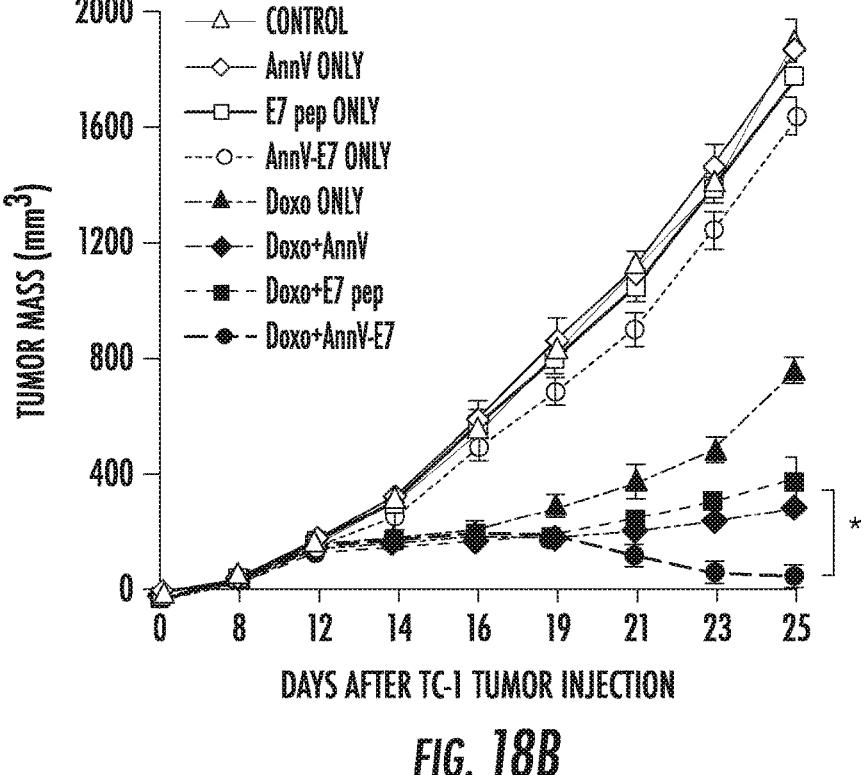
Figure 18C:
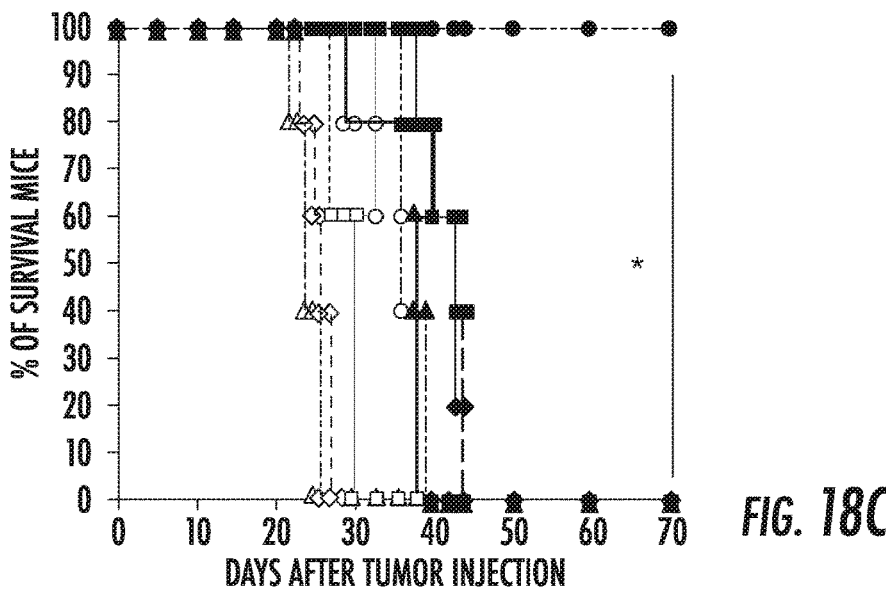
Figure 18D:
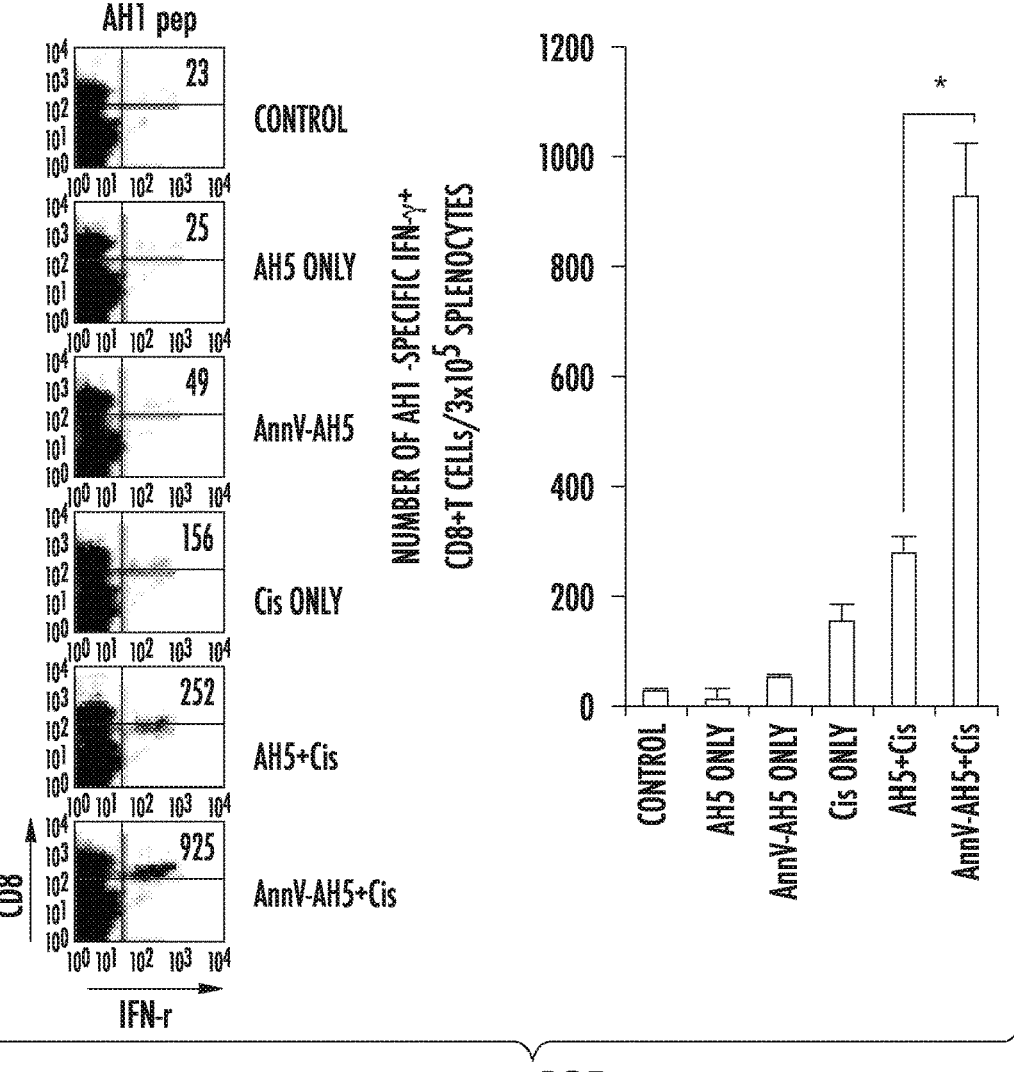
Figure 18E:
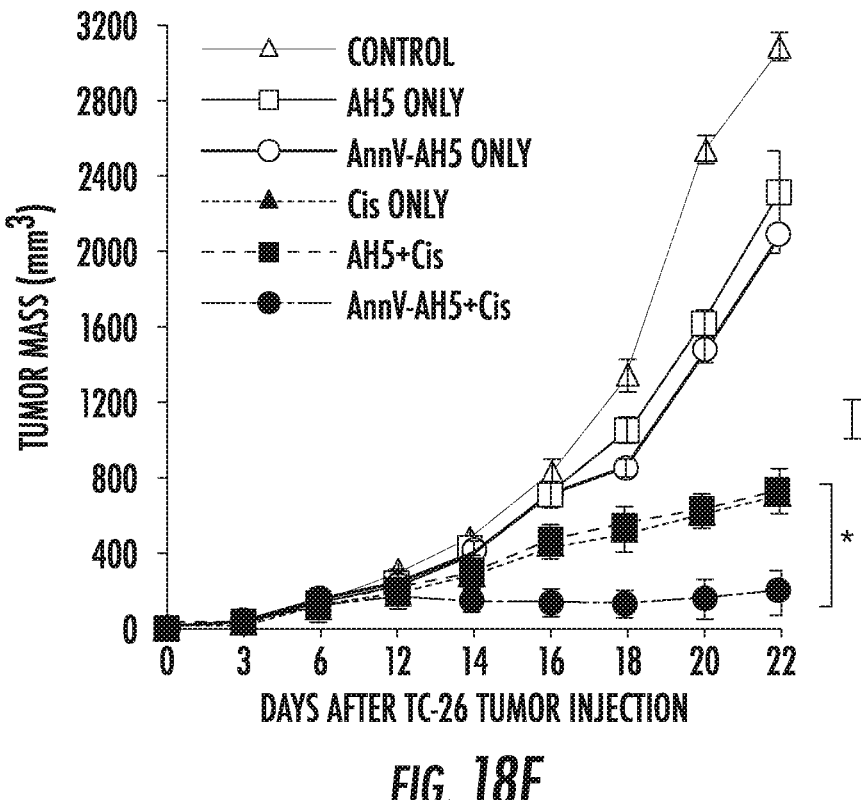
Figure 18F:
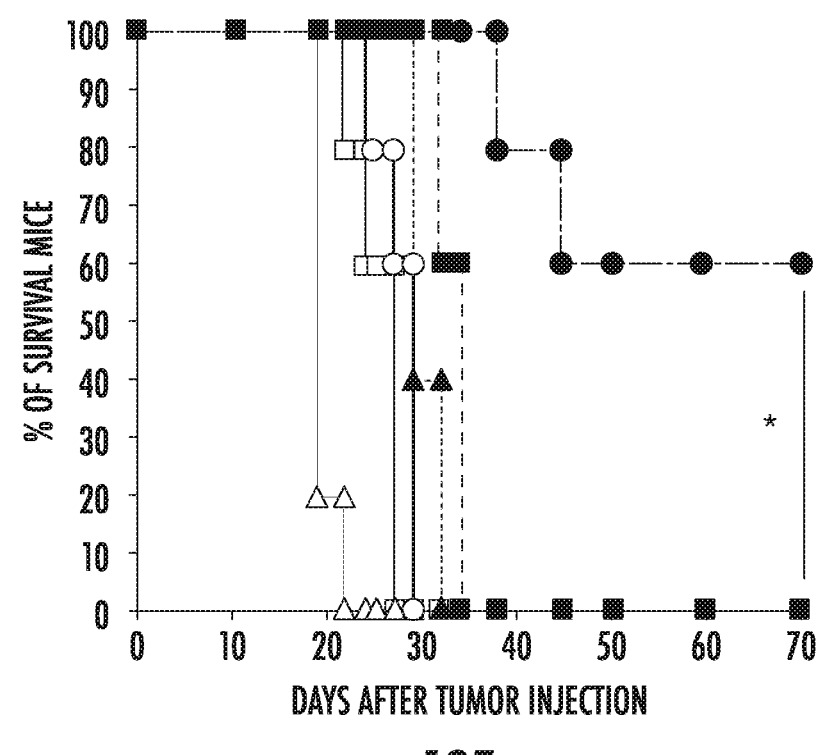

We further evaluated the therapeutic antitumor efficacy of AnnV—antigenic peptide fusion protein following the administration of a different chemotherapeutic agent, doxorubicin, and against a different tumor model. Similar to the experiments utilizing cisplatin chemotherapy, TC-1 tumor bearing mice treated with doxorubicin and AnnV-E7 generated strongest E7-specific CD8+ T cell response as well as potent tumor control and prolonged survival as compared to those in other treatment groups (FIGS. 18A-C). Similarly, in our experiment that utilized a murine colorectal cancer model, CT26 tumor cells, and AnnV fused with the peptide epitope (SPSYAYHQF) (SEQ ID NO: 13) of AH5, the reported tumor antigen of CT26 (AnnV-AH5), CT26 tumor bearing mice treated with cisplatin and AnnV-AH5 generated strongest AH5-specific CD8+ T cell response as well as potent tumor control and prolonged survival as compared to those that received other treatment regimens (FIGS. 18D-F).

Together, these data demonstrated that fusing antigenic peptides to AnnV is a viable strategy to enhance the therapeutic antitumor immune response following chemotherapy for the treatment of tumors.

Example 11

Combining Annexin V-antigenic peptide fusion protein treatment with the administration of other immune checkpoint inhibitors following chemotherapy generates enhanced therapeutic antitumor effect and potent antigen-specific immune response.

Figure 19A:
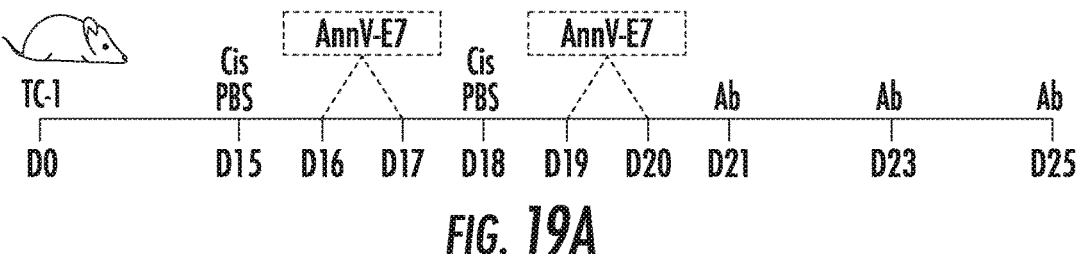
Figure 19B:
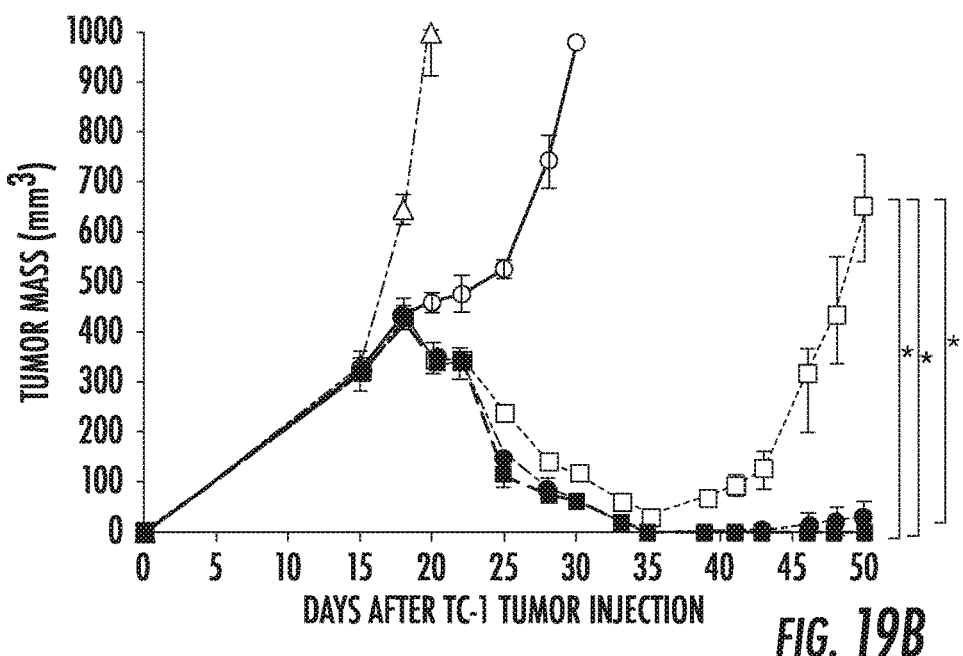
Figure 19C:
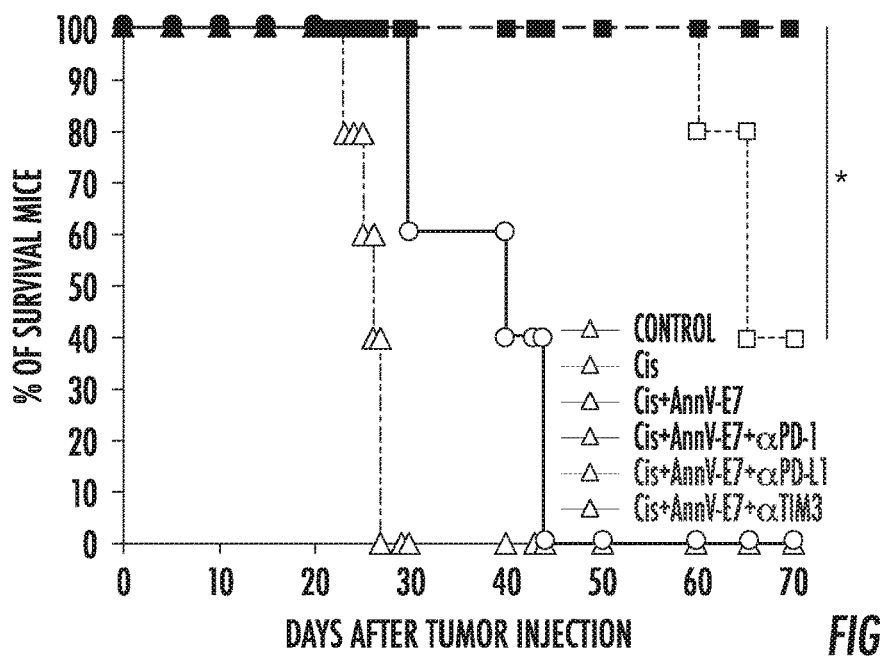

Recent studies have highlighted the therapeutic potential of rational combination of various immune checkpoint blockades for the generation of synergistic antitumor immunity. To assess whether the therapeutic efficacy of AnnV and tumor antigenic peptide fusion protein can be further enhanced by other immune checkpoint inhibitors, we treated TC-1 tumor bearing mice with cisplatin and/or AnnV-E7 with or without additional treatment with anti-PD-1, anti-PD-L1, or anti-TIM-3, using a delayed treatment schedule (FIG. 19A). While the initiation of cisplatin and AnnV-E7 treatment at 15 days after TC-1 tumor challenge could result in the initial control of TC-1 tumor, resurgence of tumor growth was observed at 35 days after tumor challenge, and only 40% of mice were still alive at 70 days after tumor challenge (FIGS. 19B-C). In comparison, no recurrence of TC-1 tumor growth were observed in mice treated with cisplatin, AnnV-E7, and anti-PD-1, anti-PD-L1, or anti-TIM-3 (FIG. 19B). In addition, all mice treated with cisplatin, AnnV-E7, and additional immune checkpoint inhibitors

Figure 19D:
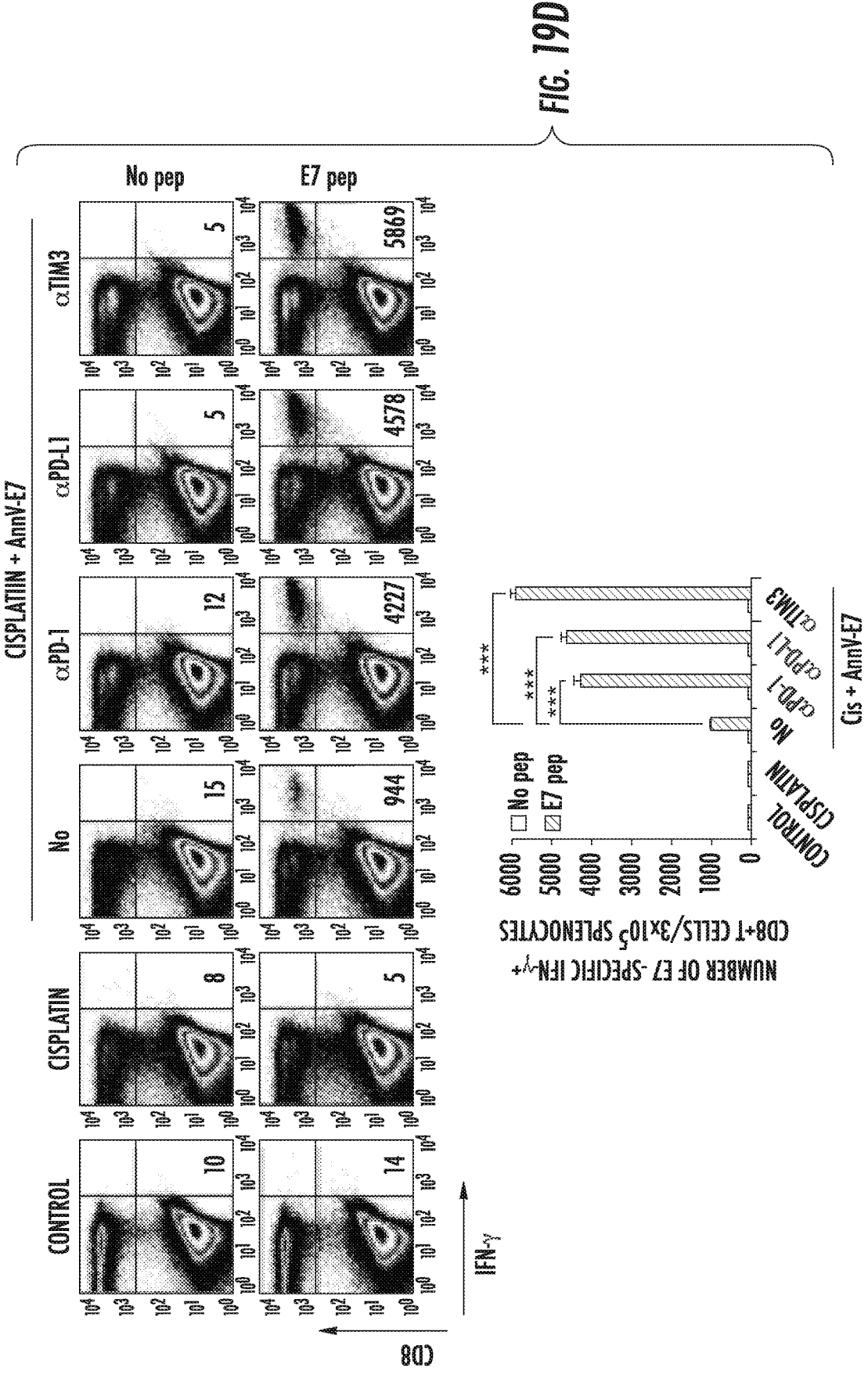

42 survived for at least 70 days after TC-1 tumor challenge (FIG. 19C). Furthermore, compared to those in TC-1 tumor-bearing, cisplatin and AnnV-E7 treated mice, combination treatment of cisplatin, AnnV-E7, and additional immune checkpoint inhibitor generated significantly stronger E7-specific CD8+ T cell response in TC-1 tumor bearing mice (FIG. 19D). These data support the rational combination of AnnV-E7 with additional immune checkpoint blockade therapy for the generation of enhanced therapeutic antitumor immunity following chemotherapy.

These findings demonstrate the ability of the inventive compositions to inhibit chemotherapy-induced immune suppression in the TME. Particularly, the inventors showed that systemic administration of AnnV compositions of the present invention following chemotherapy can enhance the immunogenicity of local tumor antigens and can further synergize with other immune checkpoint inhibitors for enhanced therapeutic potency.

The present invention focuses on the ability of the inventive constructs of AnnV to act as an immune checkpoint inhibitor against PS-induced tumor immune suppression. In addition, our findings also support the importance of potent, localized antigen-specific immune responses for effective cancer treatment. While AnnV administration alone following cisplatin treatment can rescue the immunosuppressive effects within the TME (FIG. 10), cisplatin and AnnV treatment is not effective at controlling the growth of tumor and prolonging mouse survival (FIGS. 9, 16, & 18). The correlation of strong, tumor infiltrating, local CD8+ T cell responses and the regression of cancer has been demonstrated in previous studies, and strategies to enhance the generation of tumor infiltrating lymphocytes have become an emerging focus of immunotherapeutic development. Here we showed that due to the concentrated PS expression within the TME, AnnV can serve not only as an immune checkpoint inhibitor to combat tumor immune suppression, but also as homing molecule to target fused antigenic peptides to TME and enhance the localized antigen-specific antitumor immunity (FIGS. 16-19).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

1. Klinger M H. Platelets and inflammation. Anat Embryol (Berl). 1997; 196(1):1-11. Epub 1997/07/01. PubMed PMID: 9242884.
2. Andre P, Prasad K S, Denis C V, He M, Papalia J M, Hynes R O, Phillips D R, Wagner D D. CD40L stabilizes arterial thrombi by a beta3 integrin-dependent mechanism. Nat Med. 2002; 8(3):247-52. Epub 2002/03/05. doi: 10.1038/nm0302-247. PubMed PMID: 11875495.
3. Bhogal R H, Weston C J, Curbishley S M, Adams D H, Afford S C. Activation of CD40 with platelet derived CD154 promotes reactive oxygen species dependent death of human hepatocytes during hypoxia and reoxygenation. PLoS One. 2012; 7(1):e30867. Epub 2012/02/02. doi: 10.1371/journal.pone.0030867. PubMed PMID: 22295117; PMCID: PMC3266283.
4. Elzey B D, Tian J, Jensen R J, Swanson A K, Lees J R, Lentz S R, Stein C S, Nieswandt B, Wang Y, Davidson B L, Ratliff T L. Platelet-mediated modulation of adaptive immunity. A communication link between innate and adaptive immune compartments. Immunity. 2003; 19(1): 9-19. Epub 2003/07/23. PubMed PMID: 12871635.
5. Sierko E, Wojtukiewicz M Z. Platelets and angiogenesis in malignancy. Semin Thromb Hemost. 2004; 30(1):95-108. Epub 2004/03/23. doi: 10.1055/s-2004-822974. PubMed PMID: 15034801.
6. Borsig L. The role of platelet activation in tumor metastasis. Expert Rev Anticancer Ther. 2008; 8(8):1247-55. Epub 2008/08/14. doi: 10.1586/14737140.8.8.1247. PubMed PMID: 18699763.
7. Gay L J, Felding-Habermann B. Contribution of platelets to tumour metastasis. Nat Rev Cancer. 2011; 11(2):123-34. Epub 2011/01/25. doi: 10.1038/nrc3004. PubMed PMID: 21258396.
8. Jurasz P, Alonso-Escolano D, Radomski M W. Platelet-cancer interactions: mechanisms and pharmacology of tumour cell-induced platelet aggregation. Br J Pharmacol. 2004; 143(7):819-26. Epub 2004/10/20. doi: 10.1038/sj.bjp.0706013. PubMed PMID: 15492016; PMCID: PMC1575943.
9. Francis J L, Biggerstaff J, Amirkhosravi A. Hemostasis and malignancy. Semin Thromb Hemost. 1998; 24(2):93-109. Epub 1998/05/14. doi: 10.1055/s-2007-995829. PubMed PMID: 9579631.
10. Karpatkin S, Pearlstein E. Role of platelets in tumor cell metastases. Ann Intern Med. 1981; 95(5):636-41. Epub 1981/11/01. PubMed PMID: 7027860.
11. Ho-Tin-Noe B, Goerge T, Cifuni S M, Duerschmied D, Wagner D D. Platelet granule secretion continuously prevents intratumor hemorrhage. Cancer Res. 2008;

68(16):6851-8. Epub 2008/08/15. doi: 10.1158/0008-5472.CAN-08-0718. PubMed PMID: 18701510; PMCID: PMC2547489.
12. Lou X L, Sun J, Gong S Q, Yu X F, Gong R, Deng H. Interaction between circulating cancer cells and platelets: clinical implication. Chin J Cancer Res. 2015; 27(5):450-60. Epub 2015/11/07. doi: 10.3978/j.issn.1000-9604.2015.04.10. PubMed PMID: 26543331; PMCID: PMC4626816.
13. Blankenberg F G. Imaging the molecular signatures of apoptosis and injury with radiolabeled annexin V. Proc Am Thorac Soc. 2009; 6(5):469-76. Epub 2009/08/19. doi: 10.1513/pats.200901-001A W. PubMed PMID: 19687221; PMCID: PMC2731806.
14. A1-Nedawi K, Meehan B, Kerbel R S, Allison A C, Rak J. Endothelial expression of autocrine VEGF upon the uptake of tumor-derived microvesicles containing oncogenic EGFR. Proc Natl Acad Sci USA. 2009; 106(10): 3794-9. Epub 2009/02/24. doi: 10.1073/pnas.0804543106. PubMed PMID: 19234131; PMCID: PMC2656159.
15. Zhang X, Huo L, Jin H, Han Y, Wang J, Zhang Y, Lai X, Le Z, Zhang J, Hua Z. Anti-cancer activity of Annexin V in murine melanoma model by suppressing tumor angiogenesis. Oncotarget. 2017; 8(26):42602-12. Epub 2017/04/14. doi: 10.18632/oncotarget.16645. PubMed PMID: 28402934; PMCID: PMC5522091.
16. Funakoshi T, Hendrickson L E, McMullen B A, Fujikawa K. Primary structure of human placental anticoagulant protein. Biochemistry. 1987; 26(25):8087-92. Epub 1987/12/15. PubMed PMID: 2964863.
17. Funakoshi T, Heimark R L, Hendrickson L E, McMullen B A, Fujikawa K. Human placental anticoagulant protein: isolation and characterization. Biochemistry. 1987; 26(17):5572-8. Epub 1987/08/25. PubMed PMID: 2960376.
18. Ramstrom S, O'Neill S, Dunne E, Kenny D. Annexin V binding to platelets is agonist, time and temperature dependent. Platelets. 2010; 21(4):289-96. Epub 2010/03/17. doi: 10.3109/09537101003660564. PubMed PMID: 20230207.
19. Thorpe P E. Targeting anionic phospholipids on tumor blood vessels and tumor cells. Thromb Res. 2010; 125 Suppl 2:S134-7. Epub 2010/05/15. doi: 10.1016/S0049-3848(10)70031-1. PubMed PMID: 20433993.
20. Wakeham K, Kavanagh K. The burden of HPV-associated anogenital cancers. Curr Oncol Rep. 2014; 16(9): 402. Epub 2014/08/15. doi: 10.1007/s11912-014-0402-4. PubMed PMID: 25118645.
21. Small W, Jr., Bacon M A, Bajaj A, Chuang L T, Fisher B J, Harkenrider M M, Jhingran A, Kitchener H C, Mileshkin L R, Viswanathan A N, Gaffney D K. Cervical cancer: A global health crisis. Cancer. 2017; 123(13): 2404-12. Epub 2017/05/04. doi: 10.1002/cncr.30667. PubMed PMID: 28464289.
22. Forman D, de Martel C, Lacey C J, Soerjomataram I, Lortet-Tieulent J, Bruni L, Vignat J, Ferlay J, Bray F, Plummer M, Franceschi S. Global burden of human papillomavirus and related diseases. Vaccine. 2012; 30 Suppl 5:F12-23. Epub 2012/12/05. doi: 10.1016/j.vaccine.2012.07.055. PubMed PMID: 23199955.
23. Huang B, Mao C P, Peng S, He L, Hung C F, Wu T C. Intradermal administration of DNA vaccines combining a strategy to bypass antigen processing with a strategy to prolong dendritic cell survival enhances DNA vaccine potency. Vaccine. 2007; 25(45):7824-31. Epub 2007/10/

13. doi: 10.1016/j.vaccine.2007.08.036. PubMed PMID: 17931752; PMCID: PMC2128728.

24. Munoz L E, Frey B, Pausch F, Baum W, Mueller R B, Brachvogel B, Poschl E, Rodel F, von der Mark K, Herrmann M, Gaipl U S. The role of annexin A5 in the modulation of the immune response against dying and dead cells. Curr Med Chem. 2007; 14(3):271-7. Epub 2007/02/20. PubMed PMID: 17305532.

25. Placke T, Orgel M, Schaller M, Jung G, Rammensee H G, Kopp H G, Salih H R. Platelet-derived MHC class I confers a pseudonormal phenotype to cancer cells that subverts the antitumor reactivity of natural killer immune cells. Cancer Res. 2012; 72(2):440-8. Epub 2011/12/01. doi: 10.1158/0008-5472.CAN-11-1872. PubMed PMID: 22127925.

26. Meikle C K, Kelly C A, Garg P, Wuescher L M, Ali R A, Worth R G. Cancer and Thrombosis: The Platelet Perspective. Front Cell Dev Biol. 2016; 4:147. Epub 2017/01/21. doi: 10.3389/fcell.2016.00147. PubMed PMID: 28105409; PMCID: PMC5214375.

27. Lievens D, Zernecke A, Seijkens T, Soehnlein O, Beckers L, Munnix I C, Wijnands E, Goossens P, van Kruchten R, Thevissen L, Boon L, Flavell R A, Noelle R J, Gerdes N, Biessen E A, Daemen M J, Heemskerk J W, Weber C, Lutgens E. Platelet CD40L mediates thrombotic and inflammatory processes in atherosclerosis. Blood. 2010; 116(20):4317-27. Epub 2010/08/14. doi: 10.1182/blood-2010-01-261206. PubMed PMID: 20705757; PMCID: PMC2993630.

28. Elzey B D, Ratliff T L, Sowa J M, Crist S A. Platelet CD40L at the interface of adaptive immunity. Thromb Res. 2011; 127(3):180-3. Epub 2010/11/16. doi: 10.1016/j.thromres.2010.10.011. PubMed PMID: 21075431; PMCID: PMC3073541.

29. Michel N A, Zirlik A, Wolf D. CD40L and Its Receptors in Atherothrombosis—An Update. Front Cardiovasc Med. 2017; 4:40. Epub 2017/07/06. doi: 10.3389/fcvm.2017.00040. PubMed PMID: 28676852; PMCID: PMC5477003.

30. Goubran H A, Kotb R R, Stakiw J, Emara M E, Burnouf T. Regulation of tumor growth and metastasis: the role of tumor microenvironment. Cancer Growth Metastasis. 2014; 7:9-18. Epub 2014/06/14. doi: 10.4137/CGM.S11285. PubMed PMID: 24926201; PMCID: PMC4051818.

31. Hailemichael Y, Overwijk W W. Cancer vaccines: Trafficking of tumor-specific T cells to tumor after therapeutic vaccination. Int J Biochem Cell Biol. 2014; 53:46-50. Epub 2014/05/07. doi: 10.1016/j.biocel.2014.04.019. PubMed PMID: 24796845; PMCID: PMC4111967.

32. Frey A B. Suppression of T cell responses in the tumor microenvironment. Vaccine. 2015; 33(51):7393-400. Epub 2015/09/26. doi: 10.1016/j.vaccine.2015.08.096. PubMed PMID: 26403368.

33. Fridman W H, Galon J, Pages F, Tartour E, Sautes-Fridman C, Kroemer G. Prognostic and predictive impact of intra- and peritumoral immune infiltrates. Cancer Res. 2011; 71(17):5601-5. Epub 2011/08/19. doi: 10.1158/0008-5472.CAN-11-1316. PubMed PMID: 21846822.

34. Sun Y, Peng S, Qiu J, Miao J, Yang B, Jeang J, Hung C F, Wu T C. Intravaginal HPV DNA vaccination with electroporation induces local CD8+ T-cell immune responses and antitumor effects against cervicovaginal tumors. Gene Ther. 2015; 22(7):528-35. Epub 2015/03/20. doi: 10.1038/gt.2015.17. PubMed PMID: 25786869; PMCID: PMC4490060.

35. Maldonado L, Teague J E, Morrow M P, Jotova I, Wu T C, Wang C, Desmarais C, Boyer J D, Tycko B, Robins H S, Clark R A, Trimble C L. Intramuscular therapeutic vaccination targeting HPV16 induces T cell responses that localize in mucosal lesions. Sci Transl Med. 2014; 6(221): 221ra13. Epub 2014/01/31. doi: 10.1126/scitranslmed.3007323. PubMed PMID: 24477000; PMCID: PMC4086631.

36. Lee S Y, Kang T H, Knoff J, Huang Z, Soong R S, Alvarez R D, Hung C F, Wu T C. Intratumoral injection of therapeutic HPV vaccinia vaccine following cisplatin enhances HPV-specific antitumor effects. Cancer Immunol Immunother. 2013; 62(7):1175-85. Epub 2013/04/26. doi: 10.1007/s00262-013-1421-y. PubMed PMID: 23615841; PMCID: PMC3690484.

37. Pialoux G, Hocini H, Perusat S, Silberman B, Salmon-Ceron D, Slama L, Journot V, Mathieu E, Gaillard C, Petitprez K, Launay O, Chene G, Group AVS. Phase I study of a candidate vaccine based on recombinant HIV-1 gp160 (MN/LAI) administered by the mucosal route to HIV-seronegative volunteers: the ANRS VAC14 study. Vaccine. 2008; 26(21):2657-66. Epub 2007/12/11. doi: 10.1016/j.vaccine.2007.11.002. PubMed PMID: 18068876.

38. Meque I, Dube K, Bierhuizen L, Zango A, Veldhuijzen N, Cumbe F, Feldblum P J, van de Wijgert J. Willingness to participate in future HIV prevention trials in Beira, Mozambique. Afr J AIDS Res. 2014; 13(4):393-8. Epub 2015/01/03. doi: 10.2989/16085906.2014.985239. PubMed PMID: 25555105.

39. Erves J C, Mayo-Gamble T L, Hull P C, Duke L, Miller S T. Adolescent Participation in HPV Vaccine Clinical Trials: Are Parents Willing? J Community Health. 2017; 42(5):894-901. Epub 2017/03/23. doi: 10.1007/s10900-017-0331-x. PubMed PMID: 28321649; PMCID: PMC5594038.

40. T. H. Kang, B. Ma, C. Wang, T. C. Wu, C. F. Hung, Targeted coating with antigenic peptide renders tumor cells susceptible to CD8(+) T cell-mediated killing. Mol Ther 21, 542-553 (2013).

41. T. H. Kang, C. P. Mao, S. Y. Lee, A. Chen, J. H. Lee, T. W. Kim, R. D. Alvarez, R. B. Roden, D. Pardoll, C. F. Hung, T. C. Wu, Chemotherapy acts as an adjuvant to convert the tumor microenvironment into a highly permissive state for vaccination-induced antitumor immunity. Cancer Res 73, 2493-2504 (2013).

42. R. B. Birge, D. S. Ucker, Innate apoptotic immunity: the calming touch of death. Cell Death Differ 15, 1096-1102 (2008).

43. D. Marguet, M. F. Luciani, A. Moynault, P. Williamson, G. Chimini, Engulfment of apoptotic cells involves the redistribution of membrane phosphatidylserine on phagocyte and prey. Nat Cell Biol 1, 454-456 (1999).

44. M. O. Li, M. R. Sarkisian, W. Z. Mehal, P. Rakic, R. A. Flavell, Phosphatidylserine receptor is required for clearance of apoptotic cells. Science 302, 1560-1563 (2003).

45. V. A. Fadok, D. L. Bratton, D. M. Rose, A. Pearson, R. A. Ezekewitz, P. M. Henson, A receptor for phosphatidylserine-specific clearance of apoptotic cells. Nature 405, 85-90 (2000).

46. R. B. Birge, S. Boeltz, S. Kumar, J. Carlson, J. Wanderley, D. Calianese, M. Barcinski, R. A. Brekken, X. Huang, J. T. Hutchins, B. Freimark, C. Empig, J. Mercer, A. J. Schroit, G. Schett, M. Herrmann, Phosphatidylserine is a global immunosuppressive signal in efferocytosis, infectious disease, and cancer. Cell Death Differ 23, 962-978 (2016).

47. S. Ran, A. Downes, P. E. Thorpe, Increased exposure of anionic phospholipids on the surface of tumor blood vessels. Cancer Res 62, 6132-6140 (2002).

48. G. P. Dunn, A. T. Bruce, H. Ikeda, L. J. Old, R. D. Schreiber, Cancer immunoediting: from immunosurveillance to tumor escape. Nat Immunol 3, 991-998 (2002).

49. W. Zou, Immunosuppressive networks in the tumour environment and their therapeutic relevance. Nat Rev Cancer 5, 263-274 (2005).

50. T. L. Whiteside, Immune suppression in cancer: effects on immune cells, mechanisms and future therapeutic intervention. Semin Cancer Biol 16, 3-15 (2006).

51. X. Huang, M. Bennett, P. E. Thorpe, A monoclonal antibody that binds anionic phospholipids on tumor blood vessels enhances the antitumor effect of docetaxel on human breast tumors in mice. Cancer Res 65, 4408-4416 (2005).

52. P. DeRose, P. E. Thorpe, D. E. Gerber, Development of bavituximab, a vascular targeting agent with immune-modulating properties, for lung cancer treatment. Immunotherapy 3, 933-944 (2011).

53. M. J. Gray, J. Gong, M. M. Hatch, V. Nguyen, C. C. Hughes, J. T. Hutchins, B. D. Freimark, Phosphatidylserine-targeting antibodies augment the anti-tumorigenic activity of anti-PD-1 therapy by enhancing immune activation and downregulating pro-oncogenic factors induced by T-cell checkpoint inhibition in murine triple-negative breast cancers. Breast Cancer Res 18, 50 (2016).

54. Y. Sun, S. Peng, J. Qiu, J. Miao, B. Yang, J. Jeang, C. F. Hung, T. C. Wu, Intravaginal HPV DNA vaccination with electroporation induces local CD8+ T-cell immune responses and antitumor effects against cervicovaginal tumors. Gene Ther 22, 528-535 (2015).

55. L. Wassen, K. Schon, J. Holmgren, M. Jertbom, N. Lycke, Local intravaginal vaccination of the female genital tract. Scand J Immunol 44, 408-414 (1996).

56. P. A. Kozlowski, S. Cu-Uvin, M. R. Neutra, T. P. Flanigan, Mucosal vaccination strategies for women. J Infect Dis 179 Suppl 3, S493-498 (1999).

57. E. T. Rudy, P. A. Newman, N. Duan, E. M. Kelly, K. J. Roberts, D. S. Seiden, HIV vaccine acceptability among women at risk: perceived barriers and facilitators to future HIV vaccine uptake. AIDS Educ Prev 17, 253-267 (2005).

58. E. Mills, S. Nixon, S. Singh, S. Dolma, A. Nayyar, S. Kapoor, Enrolling women into HIV preventive vaccine trials: an ethical imperative but a logistical challenge. PLoS Med 3, e94 (2006).

59. G. Pialoux, H. Hocini, S. Perusat, B. Silberman, D. Salmon-Ceron, L. Slama, V. Journot, E. Mathieu, C. Gaillard, K. Petitprez, O. Launay, G. Chene, A. V. S. Group, Phase I study of a candidate vaccine based on recombinant HIV-1 gp160 (MN/LAI) administered by the mucosal route to HIV-seronegative volunteers: the ANRS VAC14 study. Vaccine 26, 2657-2666 (2008).

60. I. Meque, K. Dube, L. Bierhuizen, A. Zango, N. Veldhuijzen, F. Cumbe, P. J. Feldblum, J. van de Wijgert, Willingness to participate in future HIV prevention trials in Beira, Mozambique. Afr J AIDS Res 13, 393-398 (2014).

61. D. R. Collingridge, M. Glaser, S. Osman, H. Barthel, O. C. Hutchinson, S. K. Luthra, F. Brady, L. Bouchier-Hayes, S. J. Martin, P. Workman, P. Price, E. O. Aboagye, In vitro selectivity, in vivo biodistribution and tumour uptake of annexin V radiolabelled with a positron emitting radioisotope. Br J Cancer 89, 1327-1333 (2003).

62. Y. K. Chae, A. Arya, W. lams, M. R. Cruz, S. Chandra, J. Choi, F. Giles, Current landscape and future of dual anti-CTLA4 and PD-1/PD-L1 blockade immunotherapy in cancer; lessons learned from clinical trials with melanoma and non-small cell lung cancer (NSCLC). J Immunother Cancer 6, 39 (2018).

63. H. Tsukamoto, K. Fujieda, A. Miyashita, S. Fukushima, T. Ikeda, Y. Kubo, S. Senju, H. Ihn, Y. Nishimura, H. Oshiumi, Combined blockade of IL-6 and PD-1/PD-L1 signaling abrogates mutual regulation of their immunosuppressive effects in the tumor microenvironment. Cancer Res, (2018).

The invention claimed is:

1. A synthetic polypeptide consisting essentially of an annexin V protein, or a functional portion or fragment thereof, conjugated to an antigen, or a functional portion or fragment thereof.

2. The synthetic polypeptide of claim 1, wherein the antigen is a tumor associated antigen.

3. The synthetic polypeptide of claim 1, wherein the tumor associated antigen is a human papilloma virus (HPV) tumor antigen, or a functional portion or fragment or variant thereof.

4. The synthetic polypeptide of claim 1, wherein the tumor associated antigen is AH5 (SPSYAYHQF) (SEQ ID NO: 13).

5. The synthetic polypeptide of claim 3, wherein the HPV tumor antigen is derived from HPV having a subtype selected from the group consisting of: 16, 18, 31, 33, 35, 39, 45, 51, 52, and 58.

6. The synthetic polypeptide of claim 1, wherein the HPV tumor antigen comprises the HPV oncoproteins E6 and/or E7.

7. The synthetic polypeptide of claim 1, wherein the polypeptide comprises a N-terminal end and a C-terminal end, wherein the N-terminal portion of the fusion protein comprises an annexin V protein, or a functional portion or fragment or variant thereof, conjugated to an antigen, or a functional portion or fragment or variant thereof, at the C-terminal portion of the fusion protein.

8. The synthetic polypeptide of claim 1, wherein the polypeptide comprises a N-terminal end and a C-terminal end, wherein the N-terminal portion of the fusion protein comprises an antigen, or a functional portion or fragment or variant thereof, conjugated to an annexin V protein, or a functional portion or fragment or variant thereof, at the C-terminal portion of the fusion protein.

9. The synthetic polypeptide of claim 1, wherein the HPV tumor antigen is derived from HPV 16 or HPV 18.

10. The synthetic polypeptide of claim 1, wherein the HPV tumor antigen comprises the HPV oncoprotein E6 or the HPV oncoprotein E7.

11. A pharmaceutical composition comprising the synthetic polypeptide of claim 1, and a pharmaceutically acceptable carrier.

12. A method for treating a subject suffering from or susceptible a hyperproliferative disease, comprising:

administering an effective amount of a synthetic polypeptide of claim 1 to the subject.

13. A method for treating a subject suffering from or susceptible to cancer, comprising:

administering an effective amount of a synthetic polypeptide of claim 1 to the subject.

14. A method for treating a subject suffering from or susceptible to a tumor, comprising:

administering an effective amount of a synthetic polypeptide of claim 1 to the subject.

15. A method for treating a subject suffering from or susceptible a hyperproliferative disease, comprising:

administering one or more doses of a chemotherapeutic agent to the subject; and thereafter administering an effective amount of a synthetic polypeptide of claim 1 to the subject.

16. A method for treating a subject suffering from or susceptible to cancer, comprising:

administering one or more doses of a chemotherapeutic agent to the subject; and thereafter administering an effective amount of a synthetic polypeptide of claim 1 to the subject.

17. A method for treating a subject suffering from or susceptible to a tumor, comprising:

administering one or more doses of a chemotherapeutic agent to the subject; and thereafter administering an effective amount of a synthetic polypeptide of claim 1 to the subject.

18. A synthetic polypeptide consisting of an annexin V protein, or a functional portion or fragment thereof, conjugated to an antigen, or a functional portion or fragment thereof.

19. The synthetic polypeptide of claim 18, wherein the tumor associated antigen is AH5 (SPSYAYHQF) (SEQ ID NO: 13).

20. The synthetic polypeptide of claim 18, wherein the tumor associated antigen is a human papilloma virus (HPV) tumor antigen, or a functional portion or fragment or variant thereof.

21. The synthetic polypeptide of claim 20, wherein the HPV tumor antigen is derived from HPV having a subtype selected from the group consisting of: 16, 18, 31, 33, 35, 39, 45, 51, 52, and 58.

* * * * *

SEQUENCE LISTING

```
<160> NUMBER OF SEQ ID NOS: 16

<210> SEQ ID NO 1
<211> LENGTH: 320
<212> TYPE: PRT
<213> ORGANISM: Homo sapiens

<400> SEQUENCE: 1

Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
            20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
    50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110
```

-continued

```
Ile Ile Ala Ser Arg Thr Pro Glu Glu Leu Arg Ala Ile Lys Gln Val
        115                 120                 125

Tyr Glu Glu Glu Tyr Gly Ser Ser Leu Glu Asp Asp Val Val Gly Asp
    130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
                180                 185                 190

Lys Phe Ile Thr Ile Phe Gly Thr Arg Ser Val Ser His Leu Arg Lys
                195                 200                 205

Val Phe Asp Lys Tyr Met Thr Ile Ser Gly Phe Gln Ile Glu Glu Thr
    210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
                260                 265                 270

Met Val Ser Arg Ser Glu Ile Asp Leu Phe Asn Ile Arg Lys Glu Phe
                275                 280                 285

Arg Lys Asn Phe Ala Thr Ser Leu Tyr Ser Met Ile Lys Gly Asp Thr
    290                 295                 300

Ser Gly Asp Tyr Lys Lys Ala Leu Leu Leu Leu Cys Gly Glu Asp Asp
305                 310                 315                 320

<210> SEQ ID NO 2
<211> LENGTH: 158
<212> TYPE: PRT
<213> ORGANISM: Alphapapillomavirus 9

<400> SEQUENCE: 2

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
                35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
                100                 105                 110

Cys Gln Lys Pro Leu Cys Pro Glu Glu Lys Gln Arg His Leu Asp Lys
                115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155
```

-continued

<210> SEQ ID NO 3
<211> LENGTH: 158
<212> TYPE: PRT
<213> ORGANISM: Alphapapillomavirus 7

<400> SEQUENCE: 3

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
                35                  40                  45

Phe Lys Asp Leu Phe Val Val Tyr Arg Asp Ser Ile Pro His Ala Ala
            50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu Gln Arg Arg Arg Glu Thr Gln Val
145                 150                 155
```

<210> SEQ ID NO 4
<211> LENGTH: 98
<212> TYPE: PRT
<213> ORGANISM: Alphapapillomavirus 9

<400> SEQUENCE: 4

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro
```

<210> SEQ ID NO 5
<211> LENGTH: 105
<212> TYPE: PRT
<213> ORGANISM: Alphapapillomavirus 7

<400> SEQUENCE: 5

```
Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30
```

-continued

```
Asp Ser Glu Glu Glu Asn Asp Glu Ile Asp Gly Val Asn His Gln His
        35                  40                  45

Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105
```

<210> SEQ ID NO 6
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ala Gln Val Leu Arg Gly Thr Val Thr Asp Phe Pro Gly Phe Asp
1               5                   10                  15

Glu Arg Ala Asp Ala Glu Thr Leu Arg Lys Ala Met Lys Gly Leu Gly
                20                  25                  30

Thr Asp Glu Glu Ser Ile Leu Thr Leu Leu Thr Ser Arg Ser Asn Ala
        35                  40                  45

Gln Arg Gln Glu Ile Ser Ala Ala Phe Lys Thr Leu Phe Gly Arg Asp
        50                  55                  60

Leu Leu Asp Asp Leu Lys Ser Glu Leu Thr Gly Lys Phe Glu Lys Leu
65                  70                  75                  80

Ile Val Ala Leu Met Lys Pro Ser Arg Leu Tyr Asp Ala Tyr Glu Leu
                85                  90                  95

Lys His Ala Leu Lys Gly Ala Gly Thr Asn Glu Lys Val Leu Thr Glu
            100                 105                 110

Ile Ile Ala Ser Arg Thr Pro Glu Glu Leu Arg Ala Ile Lys Gln Val
            115                 120                 125

Tyr Glu Glu Glu Tyr Gly Ser Ser Leu Glu Asp Asp Val Val Gly Asp
        130                 135                 140

Thr Ser Gly Tyr Tyr Gln Arg Met Leu Val Val Leu Leu Gln Ala Asn
145                 150                 155                 160

Arg Asp Pro Asp Ala Gly Ile Asp Glu Ala Gln Val Glu Gln Asp Ala
                165                 170                 175

Gln Ala Leu Phe Gln Ala Gly Glu Leu Lys Trp Gly Thr Asp Glu Glu
            180                 185                 190

Lys Phe Ile Thr Ile Phe Gly Thr Arg Ser Val Ser His Leu Arg Lys
            195                 200                 205

Val Phe Asp Lys Tyr Met Thr Ile Ser Gly Phe Gln Ile Glu Glu Thr
        210                 215                 220

Ile Asp Arg Glu Thr Ser Gly Asn Leu Glu Gln Leu Leu Leu Ala Val
225                 230                 235                 240

Val Lys Ser Ile Arg Ser Ile Pro Ala Tyr Leu Ala Glu Thr Leu Tyr
                245                 250                 255

Tyr Ala Met Lys Gly Ala Gly Thr Asp Asp His Thr Leu Ile Arg Val
            260                 265                 270

Met Val Ser Arg Ser Glu Ile Asp Leu Phe Asn Ile Arg Lys Glu Phe
        275                 280                 285
```

```
Arg Lys Asn Phe Ala Thr Ser Leu Tyr Ser Met Ile Lys Gly Asp Thr
    290                 295             300

Ser Gly Asp Tyr Lys Lys Ala Leu Leu Leu Leu Cys Gly Glu Asp Asp
305             310             315             320

Glu Phe Met His Gly Asp Thr Pro Thr Leu His Glu Tyr Met Leu Asp
            325             330             335

Leu Gln Pro Glu Thr Thr Asp Leu Tyr Cys Tyr Glu Gln Leu Asn Asp
        340             345             350

Ser Ser Glu Glu Glu Asp Glu Ile Asp Gly Pro Ala Gly Gln Ala Glu
    355             360             365

Pro Asp Arg Ala His Tyr Asn Ile Val Thr Phe Cys Cys Lys Cys Asp
    370             375             380

Ser Thr Leu Arg Leu Cys Val Gln Ser Thr His Val Asp Ile Arg Thr
385             390             395             400

Leu Glu Asp Leu Leu Met Gly Thr Leu Gly Ile Val Cys Pro Ile Cys
            405             410             415

Ser Gln Lys Pro
            420

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttggatcca tggcacaggt tctcagagg                                    29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaagaattcg tcatcttctc cacagagca                                    29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaagaattca tgcatggaga tacacctaca                                   30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tttctcgagt ggtttctgag aacagatggg gc                                32
```

-continued

```
<210> SEQ ID NO 11
<211> LENGTH: 22
<212> TYPE: PRT
<213> ORGANISM: Homo sapiens

<400> SEQUENCE: 11

Ala Gly Gln Ala Glu Pro Asp Arg Ala His Tyr Asn Ile Val Thr Phe
1               5                   10                  15

Cys Cys Lys Cys Asp Ser
            20

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala His Tyr Asn Ile Val Thr Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Pro Ser Tyr Ala Tyr His Gln Phe
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ile Ile Asn Phe Glu Lys Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Pro Ser Tyr Val Tyr His Gln Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

-continued

```
<400> SEQUENCE: 16

His His His His His His
1               5
```